(12) United States Patent
Horseman

(10) Patent No.: US 10,108,783 B2
(45) Date of Patent: Oct. 23, 2018

(54) SYSTEMS, COMPUTER MEDIUM AND COMPUTER-IMPLEMENTED METHODS FOR MONITORING HEALTH OF EMPLOYEES USING MOBILE DEVICES

(75) Inventor: Samantha J. Horseman, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 858 days.

(21) Appl. No.: 13/540,300

(22) Filed: Jul. 2, 2012

(65) Prior Publication Data

US 2013/0013331 A1 Jan. 10, 2013

Related U.S. Application Data

(60) Provisional application No. 61/504,638, filed on Jul. 5, 2011, provisional application No. 61/659,831, filed
(Continued)

(51) Int. Cl.
*G06Q 50/22* (2018.01)
*G06F 19/00* (2018.01)
(Continued)

(52) U.S. Cl.
CPC ........ *G06F 19/3418* (2013.01); *A61B 5/0002* (2013.01); *A61B 5/0022* (2013.01); *A61B 5/1038* (2013.01)

(58) Field of Classification Search
None
See application file for complete search history.

(56) References Cited

U.S. PATENT DOCUMENTS 4,951,963 A 8/1990 Behr et al.
4,998,534 A 3/1991 Claxton, III et al.
(Continued)

FOREIGN PATENT DOCUMENTS

AU 767533 11/2003
CN 101065752 A 10/2007
(Continued)

OTHER PUBLICATIONS

Bed-Check Co., Bed-Check Monitoring Systems, 2006.
(Continued)

*Primary Examiner* — Elaine Gort
*Assistant Examiner* — Rajiv J Raj
(74) *Attorney, Agent, or Firm* — Bracewell LLP; Constance G. Rhebergen; Christopher L. Drymalla

(57) ABSTRACT

Provided are embodiments of systems, computer medium and computer-implemented methods for monitoring the health of an employee. The method including collecting health data from a set of one or more health sensors provided, on or near the employee while the employee is engaged in their work duties. The one or more health sensors configured to output health data corresponding to characteristics sensed by the sensor, the one or more health sensors comprising at least one or more biometric and biomechanic sensors configured to sense biometric and biomechanic characteristics of the employee with at least one of the one or more health sensors integrated within a mobile communications device. The health data collected being used to determine a health profile for the employee. The method including displaying, via the mobile communications device, a health report that includes the health profile for the employee.

24 Claims, 14 Drawing Sheets

Related U.S. Application Data on Jun. 14, 2012, provisional application No. 61/659,790, filed on Jun. 14, 2012, provisional application No. 61/659,796, filed on Jun. 14, 2012, provisional application No. 61/659,800, filed on Jun. 14, 2012, provisional application No. 61/659,807, filed on Jun. 14, 2012, provisional application No. 61/659,810, filed on Jun. 14, 2012, provisional application No. 61/659,818, filed on Jun. 14, 2012, provisional application No. 61/659,824, filed on Jun. 14, 2012, provisional application No. 61/664,387, filed on Jun. 26, 2012, provisional application No. 61/664,399, filed on Jun. 26, 2012, provisional application No. 61/664,414, filed on Jun. 26, 2012.

(51) Int. Cl.
*A61B 5/103* (2006.01)
*A61B 5/00* (2006.01)

(56) References Cited

U.S. PATENT DOCUMENTS

| | | |
|---|---|---|
| 5,000,188 A | 3/1991 | Kojima |
| 5,111,539 A | 5/1992 | Hiruta et al. |
| 5,304,112 A | 4/1994 | Mrklas et al. |
| 5,305,238 A | 4/1994 | Starr, III |
| 5,323,650 A | 6/1994 | Fullen et al. |
| 5,441,047 A | 8/1995 | David |
| 5,542,420 A | 8/1996 | Goldman et al. |
| 5,570,301 A | 10/1996 | Barrus |
| 5,573,269 A | 11/1996 | Gentry et al. |
| 5,673,691 A | 10/1997 | Abrams et al. |
| 5,792,047 A | 8/1998 | Coggins |
| 5,926,806 A | 7/1999 | Marshall et al. |
| 5,937,387 A | 8/1999 | Summerell et al. |
| 6,033,344 A | 3/2000 | Trulaske et al. |
| 6,049,281 A | 4/2000 | Osterweil |
| 6,080,106 A | 6/2000 | Lloyd et al. |
| 6,083,156 A | 7/2000 | Lisiecki |
| 6,104,296 A | 8/2000 | Yasuchi et al. |
| 6,149,586 A | 11/2000 | Elkind |
| 6,190,314 B1 | 2/2001 | Ark et al. |
| 6,198,394 B1 | 3/2001 | Jacobsen et al. |
| 6,269,339 B1 | 7/2001 | Silver |
| 6,281,594 B1 | 8/2001 | Sarich |
| 6,291,900 B1 | 9/2001 | Tiemann et al. |
| 6,293,771 B1 | 9/2001 | Haney et al. |
| 6,307,476 B1 | 10/2001 | Smith et al. |
| 6,309,342 B1 | 10/2001 | Blazey et al. |
| 6,334,837 B1 | 1/2002 | Hein et al. |
| 6,345,839 B1 | 2/2002 | Kuboki et al. |
| 6,353,764 B1 | 3/2002 | Imagawa et al. |
| 6,369,337 B1 | 4/2002 | Machiyama |
| 6,381,577 B1 | 4/2002 | Brown |
| 6,383,136 B1 | 5/2002 | Jordan |
| 6,408,263 B1 | 6/2002 | Summers |
| 6,425,862 B1 | 7/2002 | Brown |
| 6,452,862 B1 | 9/2002 | Tomotani |
| 6,546,286 B2 | 4/2003 | Olson |
| 6,572,558 B2 | 6/2003 | Masakov et al. |
| 6,585,645 B2 | 7/2003 | Hutchinson |
| 6,594,607 B2 | 7/2003 | Lavery |
| 6,646,556 B1 | 11/2003 | Smith et al. |
| 6,648,820 B1 | 11/2003 | Sarel |
| 6,673,027 B2 | 1/2004 | Fischer |
| 6,692,258 B1 | 2/2004 | Kurzweil |
| 6,705,990 B1 | 3/2004 | Gallant et al. |
| 6,736,642 B2 | 5/2004 | Bajer |
| 6,767,330 B2 | 7/2004 | Lavery et al. |
| 6,768,246 B2 | 7/2004 | Pelrine et al. |
| 6,828,908 B2 | 12/2004 | Clark |
| 6,832,987 B2 | 12/2004 | David et al. |
| 6,850,798 B2 | 2/2005 | Morgan |
| 6,918,769 B2 | 7/2005 | Rink |
| 6,982,497 B2 | 1/2006 | Rome |
| 7,005,757 B2 | 2/2006 | Pandian |
| 7,027,621 B1 | 4/2006 | Prokoski |
| 7,063,665 B2 | 6/2006 | Hasegawa et al. |
| 7,074,198 B2 | 7/2006 | Krullaards |
| 7,104,965 B1 | 9/2006 | Jiang et al. |
| 7,109,872 B2 | 9/2006 | Balaban et al. |
| 7,128,577 B2 | 10/2006 | Renaud |
| 7,152,024 B2 | 12/2006 | Marschner |
| 7,155,158 B1 | 12/2006 | Iuppa |
| 7,163,489 B1 | 1/2007 | Nelson |
| 7,188,151 B2 | 3/2007 | Kumar et al. |
| 7,233,312 B2 | 6/2007 | Stern et al. |
| 7,273,453 B2 | 9/2007 | Shallenberger |
| 7,304,580 B2 | 12/2007 | Sullivan et al. |
| 7,315,249 B2 | 1/2008 | Littell |
| 7,351,206 B2 | 4/2008 | Suzuki |
| 7,407,484 B2 | 8/2008 | Korman |
| 7,481,779 B2 | 1/2009 | Large |
| 7,598,881 B2 | 10/2009 | Morgan |
| 7,624,037 B2 | 11/2009 | Bost |
| 7,652,582 B2 | 1/2010 | Littell et al. |
| 7,689,271 B1 | 3/2010 | Sullivan |
| 7,717,866 B2 | 5/2010 | Damen |
| 7,771,318 B2 | 8/2010 | Narayanaswami |
| 7,844,347 B2 | 11/2010 | Brabec |
| 7,849,115 B2 | 12/2010 | Reiner |
| 7,958,002 B2 | 6/2011 | Bost |
| 7,972,266 B2 | 7/2011 | Gobeyn et al. |
| 7,988,627 B2 | 8/2011 | Bagan |
| 8,015,022 B2 | 9/2011 | Gore |
| 8,018,346 B2 | 9/2011 | Gottlieb et al. |
| 8,019,121 B2 | 9/2011 | Marks |
| 8,021,298 B2 | 9/2011 | Baird |
| 8,024,202 B2 | 9/2011 | Carroll |
| 8,030,786 B2 | 10/2011 | Jackson et al. |
| 8,038,615 B2 | 10/2011 | Gobeyn |
| 8,081,083 B2 | 12/2011 | Hinterlong |
| 8,083,676 B2 | 12/2011 | Halliday |
| 8,092,226 B2 | 1/2012 | Findlay |
| 8,095,641 B2 | 1/2012 | Aggarwal et al. |
| 8,103,333 B2 | 1/2012 | Tran |
| 8,179,269 B2 | 5/2012 | Yanagi et al. |
| 8,180,457 B2 | 5/2012 | Matos |
| 8,200,323 B2 | 6/2012 | Dibenedetto et al. |
| 8,203,454 B2 | 6/2012 | Knight et al. |
| 8,219,184 B2 | 7/2012 | Stelzer et al. |
| 8,235,895 B2 | 8/2012 | David |
| 8,308,562 B2 | 11/2012 | Patton |
| 8,359,231 B2 | 1/2013 | Fitzpatrick et al. |
| 8,428,962 B1 | 4/2013 | Brinkley et al. |
| 8,477,039 B2 | 7/2013 | Gleckler et al. |
| 8,487,456 B2 | 7/2013 | Donelan et al. |
| 8,597,121 B2 | 12/2013 | Andres Del Valle |
| 8,597,142 B2 | 12/2013 | Mayles et al. |
| 8,612,247 B2 | 12/2013 | Sawano |
| 8,636,670 B2 | 1/2014 | Ferren et al. |
| 8,704,110 B2 | 4/2014 | Forshaw et al. |
| 8,738,129 B2 | 5/2014 | Packer |
| 9,043,217 B2 | 5/2015 | Cashman et al. |
| 9,044,172 B2 | 6/2015 | Baxi et al. |
| 9,364,714 B2 | 6/2016 | Koduri et al. |
| 2001/0039372 A1 | 11/2001 | Yasushi et al. |
| 2001/0040591 A1 | 11/2001 | Abbott et al. |
| 2001/0041845 A1 | 11/2001 | Kim |
| 2001/0042004 A1 | 11/2001 | Taub |
| 2002/0050924 A1 | 5/2002 | Mahbub |
| 2002/0062069 A1 | 5/2002 | Mault |
| 2002/0077534 A1 | 6/2002 | Durousseau |
| 2002/0095099 A1 | 7/2002 | Quyen et al. |
| 2002/0108576 A1 | 8/2002 | Lely et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2002/0197591 A1 | 12/2002 | Ebersole et al. |
| 2003/0010345 A1 | 1/2003 | Koblasz et al. |
| 2003/0058111 A1 | 3/2003 | Lee et al. |

(56) References Cited

U.S. PATENT DOCUMENTS

| | | |
|---|---|---|
| 2003/0060957 A1 | 3/2003 | Okamura et al. |
| 2003/0073552 A1 | 4/2003 | Knight |
| 2003/0109322 A1 | 6/2003 | Funk et al. |
| 2003/0113698 A1 | 6/2003 | Von Der Geest et al. |
| 2003/0149379 A1 | 8/2003 | Krullaards |
| 2003/0154107 A1 | 8/2003 | Medvedeff |
| 2003/0173120 A1 | 9/2003 | Desrochers et al. |
| 2003/0181830 A1 | 9/2003 | Guimond et al. |
| 2003/0201978 A1 | 10/2003 | Lee et al. |
| 2003/0209113 A1 | 11/2003 | Brooks et al. |
| 2003/0212579 A1 | 11/2003 | Brown et al. |
| 2003/0214408 A1* | 11/2003 | Grajales ............... A61B 5/0002 340/573.1 |
| 2003/0222440 A1 | 12/2003 | Basir |
| 2003/0226695 A1 | 12/2003 | Mault |
| 2004/0002634 A1 | 1/2004 | Nihtila |
| 2004/0015191 A1 | 1/2004 | Otman |
| 2004/0095378 A1 | 5/2004 | Vigue |
| 2004/0100283 A1 | 5/2004 | Meyer et al. |
| 2004/0152956 A1* | 8/2004 | Korman ........................ 600/300 |
| 2004/0162466 A1* | 8/2004 | Quy .............................. 600/300 |
| 2004/0167381 A1 | 8/2004 | Lighter et al. |
| 2004/0193068 A1 | 9/2004 | Burton et al. |
| 2004/0195876 A1 | 10/2004 | Huiban |
| 2004/0222892 A1 | 11/2004 | Balaban |
| 2004/0242976 A1* | 12/2004 | Abreu .................. A61B 5/0008 600/315 |
| 2004/0260156 A1 | 12/2004 | David |
| 2004/0263633 A1 | 12/2004 | Shinohara et al. |
| 2005/0075542 A1 | 4/2005 | Goldreich |
| 2005/0101845 A1 | 5/2005 | Nihtila |
| 2005/0108086 A1 | 5/2005 | Kosman |
| 2005/0113650 A1 | 5/2005 | Pacione et al. |
| 2005/0164833 A1 | 7/2005 | Florio |
| 2005/0165284 A1 | 7/2005 | Gefen |
| 2005/0181347 A1 | 8/2005 | Barnes |
| 2005/0237385 A1 | 10/2005 | Kosaka et al. |
| 2005/0260548 A1 | 11/2005 | Nava |
| 2005/0268401 A1 | 12/2005 | Dixon et al. |
| 2005/0270163 A1 | 12/2005 | Littell |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0047188 A1 | 3/2006 | Bohan |
| 2006/0074708 A1 | 4/2006 | Woods |
| 2006/0090135 A1 | 4/2006 | Fukuda |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0267747 A1 | 11/2006 | Kondo |
| 2007/0011273 A1 | 1/2007 | Greenstein et al. |
| 2007/0017531 A1 | 1/2007 | Large |
| 2007/0038153 A1 | 2/2007 | Basson et al. |
| 2007/0050715 A1 | 3/2007 | Behar |
| 2007/0055549 A1 | 3/2007 | Moore et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0149360 A1 | 6/2007 | Narayanaswami |
| 2007/0169364 A1 | 7/2007 | Townsend et al. |
| 2007/0179360 A1 | 8/2007 | Mikat |
| 2007/0191727 A1 | 8/2007 | Fadem |
| 2007/0225118 A1 | 9/2007 | Giorno |
| 2007/0225585 A1 | 9/2007 | Washbon et al. |
| 2007/0256494 A1 | 11/2007 | Nakamura et al. |
| 2007/0270909 A1 | 11/2007 | Saketkhou |
| 2007/0276202 A1 | 11/2007 | Raisanen et al. |
| 2007/0296556 A1 | 12/2007 | Wang et al. |
| 2007/0299325 A1 | 12/2007 | Farrell et al. |
| 2008/0001736 A1 | 1/2008 | Steadman et al. |
| 2008/0015422 A1 | 1/2008 | Wessel |
| 2008/0052837 A1 | 3/2008 | Blumberg |
| 2008/0077620 A1 | 3/2008 | Gilley et al. |
| 2008/0081963 A1 | 4/2008 | Naghavi et al. |
| 2008/0083416 A1 | 4/2008 | Xia et al. |
| 2008/0140140 A1 | 6/2008 | Grimley |
| 2008/0146892 A1 | 6/2008 | LeBoeuf et al. |
| 2008/0150889 A1 | 6/2008 | Stern |
| 2008/0161654 A1 | 7/2008 | Teller et al. |
| 2008/0171914 A1 | 7/2008 | Ouwerkerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0218331 A1 | 9/2008 | Baillot |
| 2008/0242521 A1 | 10/2008 | Einav |
| 2008/0242951 A1 | 10/2008 | Jung et al. |
| 2008/0242952 A1 | 10/2008 | Jung et al. |
| 2008/0258921 A1* | 10/2008 | Woo ..................... A61B 5/0002 340/573.1 |
| 2008/0292151 A1 | 11/2008 | Kurtz et al. |
| 2008/0294018 A1 | 11/2008 | Kurtz et al. |
| 2008/0306357 A1 | 12/2008 | Korman |
| 2008/0306762 A1 | 12/2008 | James |
| 2009/0002178 A1 | 1/2009 | Guday et al. |
| 2009/0030767 A1 | 1/2009 | Morris et al. |
| 2009/0040196 A1 | 2/2009 | Duckstein |
| 2009/0047644 A1 | 2/2009 | Mensah |
| 2009/0047645 A1 | 2/2009 | Dibenedetto et al. |
| 2009/0055204 A1 | 2/2009 | Pennington et al. |
| 2009/0058661 A1 | 3/2009 | Gleckler et al. |
| 2009/0137882 A1 | 5/2009 | Baudino et al. |
| 2009/0160640 A1 | 6/2009 | Leung et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0241177 A1 | 9/2009 | Bluth |
| 2009/0287101 A1 | 11/2009 | Ferren et al. |
| 2009/0287191 A1 | 11/2009 | Ferren |
| 2009/0298025 A1 | 12/2009 | Raber |
| 2009/0319297 A1 | 12/2009 | Hernandez et al. |
| 2009/0324024 A1 | 12/2009 | Worthington |
| 2010/0014711 A1 | 1/2010 | Camhi et al. |
| 2010/0049004 A1 | 2/2010 | Edman |
| 2010/0049541 A1 | 2/2010 | Pollard et al. |
| 2010/0063837 A1 | 3/2010 | Bellante et al. |
| 2010/0130808 A1 | 5/2010 | Hattori |
| 2010/0169118 A1 | 7/2010 | Rottsolk et al. |
| 2010/0169219 A1 | 7/2010 | Sellers et al. |
| 2010/0205541 A1 | 8/2010 | Rapaport et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0283265 A1 | 11/2010 | Rastegar et al. |
| 2010/0292545 A1 | 11/2010 | Berka et al. |
| 2010/0305480 A1 | 12/2010 | Fu et al. |
| 2010/0332250 A1 | 12/2010 | Simpson |
| 2011/0033830 A1 | 2/2011 | Cherian |
| 2011/0035231 A1 | 2/2011 | Firminger et al. |
| 2011/0046688 A1 | 2/2011 | Schwibner |
| 2011/0080290 A1 | 4/2011 | Baxi et al. |
| 2011/0098056 A1 | 4/2011 | Rhoads et al. |
| 2011/0125662 A1 | 5/2011 | Perry et al. |
| 2011/0137211 A1 | 6/2011 | Weisberg |
| 2011/0137669 A1 | 6/2011 | Bennett |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0269601 A1 | 11/2011 | Nelson et al. |
| 2011/0285146 A1 | 11/2011 | Kozinsky et al. |
| 2011/0295466 A1 | 12/2011 | Ostu et al. |
| 2011/0295656 A1 | 12/2011 | Venkatasubramanian et al. |
| 2012/0007367 A1 | 1/2012 | Chang |

(56) References Cited

U.S. PATENT DOCUMENTS

| | | | |
|---|---|---|---|
| 2012/0010488 A1 | 1/2012 | Henry et al. | |
| 2012/0035433 A1 | 2/2012 | Chance | |
| 2012/0040799 A1 | 2/2012 | Jaquish et al. | |
| 2012/0052971 A1 | 3/2012 | Bentley | |
| 2012/0071731 A1 | 3/2012 | Gottesman | |
| 2012/0075483 A1 | 3/2012 | Paoletti | |
| 2012/0086249 A1 | 4/2012 | Hotary et al. | |
| 2012/0127157 A1 | 5/2012 | Adler | |
| 2012/0130196 A1 | 5/2012 | Jain et al. | |
| 2012/0139731 A1* | 6/2012 | Razoumov | A61B 5/0022 340/573.1 |
| 2012/0143031 A1 | 6/2012 | Belalcazar et al. | |
| 2012/0143374 A1 | 6/2012 | Mistry et al. | |
| 2012/0146795 A1 | 6/2012 | Margon et al. | |
| 2012/0154277 A1 | 6/2012 | Bar-Zeev et al. | |
| 2012/0203491 A1 | 8/2012 | Sun et al. | |
| 2012/0209563 A1 | 8/2012 | Takeda et al. | |
| 2012/0215076 A1 | 8/2012 | Yang et al. | |
| 2012/0271121 A1 | 10/2012 | Della Torre et al. | |
| 2012/0283929 A1 | 11/2012 | Wakita et al. | |
| 2012/0289793 A1 | 11/2012 | Jain et al. | |
| 2012/0290215 A1 | 11/2012 | Adler | |
| 2012/0302910 A1 | 11/2012 | Freeman et al. | |
| 2013/0009761 A1 | 1/2013 | Horseman | |
| 2013/0009993 A1 | 1/2013 | Horseman | |
| 2013/0011819 A1 | 1/2013 | Horseman | |
| 2013/0012786 A1 | 1/2013 | Horseman | |
| 2013/0012787 A1 | 1/2013 | Horseman | |
| 2013/0012788 A1 | 1/2013 | Horseman | |
| 2013/0012789 A1 | 1/2013 | Horseman | |
| 2013/0012790 A1 | 1/2013 | Horseman | |
| 2013/0012802 A1 | 1/2013 | Horseman | |
| 2013/0013327 A1 | 1/2013 | Horseman | |
| 2013/0013331 A1 | 1/2013 | Horseman | |
| 2013/0056981 A1 | 3/2013 | Mullins et al. | |
| 2013/0097093 A1 | 4/2013 | Kolber et al. | |
| 2013/0158423 A1 | 6/2013 | Kapoor | |
| 2013/0178960 A1 | 7/2013 | Sheehan et al. | |
| 2013/0226413 A1 | 8/2013 | Cuddihy et al. | |
| 2013/0234826 A1 | 9/2013 | Sekiguchi et al. | |
| 2013/0243208 A1 | 9/2013 | Fawer | |
| 2013/0281798 A1 | 10/2013 | Rau et al. | |
| 2013/0289889 A1* | 10/2013 | Yuen | G06F 19/3418 702/19 |
| 2013/0297344 A1 | 11/2013 | Cosentino et al. | |
| 2013/0308099 A1 | 11/2013 | Stack | |
| 2013/0331993 A1 | 12/2013 | Detsch et al. | |
| 2013/0334851 A1 | 12/2013 | Hoell et al. | |
| 2014/0067001 A1 | 3/2014 | Schwibner et al. | |
| 2014/0100464 A1 | 4/2014 | Kaleal et al. | |
| 2014/0107718 A1 | 4/2014 | Foote | |
| 2014/0129401 A1 | 5/2014 | Kruz et al. | |
| 2014/0156259 A1 | 6/2014 | Dolan et al. | |
| 2014/0172461 A1 | 6/2014 | Rogers | |
| 2014/0222095 A1 | 8/2014 | Einy | |
| 2014/0317914 A1 | 10/2014 | Shaker | |
| 2015/0025928 A1 | 1/2015 | Kang et al. | |
| 2015/0050623 A1 | 2/2015 | Falash et al. | |
| 2015/0199494 A1 | 7/2015 | Koduri et al. | |
| 2015/0222096 A1 | 8/2015 | Nakayama | |
| 2015/0375028 A1 | 12/2015 | Oteman et al. | |

FOREIGN PATENT DOCUMENTS

| | | |
|---|---|---|
| CN | 101115438 A | 1/2008 |
| CN | 201127606 Y | 10/2008 |
| DE | 102005048496 A1 | 4/2007 |
| EP | 1407713 | 9/2008 |
| EP | 2151355 | 2/2010 |
| EP | 2248461 A2 | 11/2010 |
| EP | 2924674 A1 | 9/2015 |
| JP | 05-049603 A | 3/1993 |
| JP | 2000037357 A | 2/2000 |
| JP | 2001187030 A | 7/2001 |
| JP | 2001209717 A | 8/2001 |
| JP | 2001236141 A | 8/2001 |
| JP | 2001356849 A | 12/2001 |
| JP | 2002065630 A | 3/2002 |
| JP | 2002159052 A | 5/2002 |
| JP | 2002183647 A | 6/2002 |
| JP | 2002215880 A | 8/2002 |
| JP | 2002259120 A | 9/2002 |
| JP | 2003521972 A | 7/2003 |
| JP | 2003235813 A | 8/2003 |
| JP | 2003247991 A | 9/2003 |
| JP | 2003256578 A | 9/2003 |
| JP | 2005287688 A | 10/2005 |
| JP | 2006085262 A | 3/2006 |
| JP | 2006239157 A | 9/2006 |
| JP | 2008099834 A | 1/2008 |
| JP | 2008110032 A | 5/2008 |
| JP | 2009171544 A | 7/2009 |
| JP | 2009301360 A | 12/2009 |
| JP | 2010181324 A | 8/2010 |
| JP | 2011120787 A | 6/2011 |
| WO | 9601585 A1 | 1/1996 |
| WO | 2001028416 | 4/2001 |
| WO | 2001086403 | 11/2001 |
| WO | 03077110 A2 | 9/2003 |
| WO | 2005064447 | 7/2005 |
| WO | 2006022465 A1 | 3/2006 |
| WO | 2007016056 A2 | 2/2007 |
| WO | 2007130591 A2 | 11/2007 |
| WO | 2010048145 | 4/2010 |
| WO | 2010051037 A1 | 5/2010 |
| WO | 2011020299 | 2/2011 |
| WO | WO2014023422 A1 | 2/2014 |

OTHER PUBLICATIONS

Final Office Action for co-pending U.S. Appl. No. 13/540,067 dated Jun. 3, 2014.
Office Action for co-pending U.S. Appl. No. 13/540,095 dated May 22, 2014.
Office Action for co-pending U.S. Appl. No. 13/540,124 dated Jul. 3, 2014.
Office Action for co-pending U.S. Appl. No. 13/540,208 dated Jun. 20, 2014.
The American Heritage Dictionary of the English Language, definition of planar, 2000.
"www.mydailyhealth.com" retrieved from the "wayback machine" (pp. 1-20).
Health/Medical Writers eHealthcareWorld 2000. (May 1). MyDailyHealth.com (pp. 1-3).
Murray Hill, Well Med Team to Offer Next Generation Online Preventive Health Services. (Nov. 3). PR Newswire, 1. (pp. 1-3).
Copending U.S. Appl. No. 14/035,670 titled "Computer Mouse for Monitoring and Improving Health and Productivity of Employees", filed Sep. 24, 2013.
Copending U.S. Appl. No. 14/035,717 titled "Computer Mouse System and Associated Computer Medium for Monitoring and Improving Health and Productivity of Employees", filed Sep. 24, 2013.
Copending U.S. Appl. No. 14/035,732 titled "Methods for Monitoring and Improving Health and Productivity of Employees Using a Computer Mouse System", filed Sep. 24, 2013.
Copending U.S. Appl. No. 14/043,898 titled "Systems, Computer Medium and Computer-Implemented Methods for Quantifying and Employing Impacts of Workplace Wellness Programs", filed Oct. 2, 2013.
USPTO Communicaiton for U.S. Appl. No. 13/540,067 dated Oct. 17, 2013. (pp. 1-39).
"Making a Difference", World Health Organisation, Geneva: WHO, 1999, pp. 1-136.
"National health expenditure data", Centers for Medicare & Medicaid Services, available at: <http://www.cms.gov/Research-Statistics-Data-and-Systems/Statistics-Trends-and-Reports>, accessed Nov. 18, 2013, pp. 1-2.

(56) References Cited

OTHER PUBLICATIONS

"Piezo Electric Energy Harvester", Midé Technology Corporation, retrieved Nov. 18, 2013. pp. 1-2.

"Signal Conditioning Piezoelectric Sensors", (PDF) Texas Instruments, Application Report SLOA033A, Sep. 2000, pp. 1-6.

The constitution of the World Health Organization, World Health Organization, WHO Chronicle, 1947, pp. 1-202.

Aldana, S., "Financial Impact of health promotion programs: a comprehensive review of the literature", American Journal of Health Promotion,155, 2001, pp. 296-320.

Aldana, S., Merrill, R., Price, K., Hardy, A., and Hager, R., "Financial impact of a comprehensive multi-site worksite health promotion program", Preventive Medicine, 40, Jul. 2004, pp. 131-137.

Alfredo Vázquez Carazo, "Novel Piezoelectric Transducers for High Voltage Measurements", Jan. 2000 , pp. 1-277.

Baiker, K., Cutler, D., Song, Z., "Worksite wellness programs can generate savings", Health Affairs 29(2), Jan. 2010, pp. 1-8.

Berry, L.L., Mirabito, A.M., Baun, W.B., "What's the Hard Return on Employee Wellness Programs?", Harvard Business Review, Dec. 2010, pp. 1-10.

Chapman, L., "Expert opinions on 'best practice' in worksite health promotion (WHP)", Jul./Aug. 2004, pp. 1-13.

Chapman, L.. "Meta-evaluation of worksite health promotion economic return studies: 2012 Update", Mar./Apr. 2012, pp. 1-13.

Edington, D. W., "Emerging research: a view from one research centre", American Journal of Health Promotion, 15(5), May/Jun. 2001, pp. 341-349.

Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.

Hemp, P., "Presenteeism: At Work—But Out of It", Harvard Business Review, Oct. 2004, pp. 49-58.

Horseman, S. J ., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.

Horseman, S. J., "ErgoWELL : An Integrative Strategy", SPE Paper #: SPE-152629. Society of Petroleum Engineers, MEHSSE. Paper and Workshop, Abu Dhabi, 2012, pp. 1-17.

Johns, G., "Presenteeism in the Workplace: A review and research agenda", Journal of Organizational Behavior, Jul. 31, 2009, pp. 519-542.

Priya, S., "Advances in Energy Harvesting Using Low Profile Piezoelectric Transducers", Materials Science & Engineering, Springer, Mar. 2007, pp. 165-182.

Reidel, J.E., Baase, C., "The effect of disease prevention & health promotion on worksite productivity: a literature review", American Journal of Health Promotion, 15:3, Jan./Feb. 2001, pp. 167-191, 243.

Roberts, R.O.,Bergstralh, E.J., Schmidt, L., Jacobsoen,S.J., "Comparison of Self Reported and Medical Record Health Care Utilization Measures", Journal of Clinical Epidemiology, 49:9, Feb. 1996, pp. 989-995.

Copending U.S. Appl. No. 14/102,619 titled "Systems, Computer Medium and Computer-Implemented Methods for Harvesting Human Energy in the Workplace", filed Dec. 11, 2013.

Copending U.S. Appl. No. 14/180,529 titled "Chair Pad System and Associated, Computer Medium and Computer-Implemented Methods for Monitoring and Improving Health and Productivity of Employees" filed Feb. 14, 2014.

Copending U.S. Appl. No. 14/180,533 titled "Chair Pad System and Associated, Computer Medium and Computer-Implemented Methods for Monitoring and Improving Health and Productivity of Employees" filed Feb. 14, 2014.

Copending U.S. Appl. No. 14/180,536 titled "Floor Mat System and Associated, Computer Medium and Computer-Implemented Methods for Monitoring and Improving Health and Productivity of Employees" filed Feb. 14, 2014.

Copending U.S. Appl. No. 14/180,471 titled "Floor Mat System and Associated, Computer Medium and Computer-Implemented Methods for Monitoring and Improving Health and Productivity of Employees" filed Feb. 14, 2014.

Copending U.S. Appl. No. 14/180,993 titled "Systems, Computer Medium and Computer-Implemented Methods for Monitoring and Improving Biometric Health of Employees" filed Feb. 14, 2014.

Copending U.S. Appl. No. 14/181,006 titled "Systems, Computer Medium and Computer-Implemented Methods for Monitoring and Improving Biomechanical Health of Employees" filed Feb. 14, 2014.

Copending U.S. Appl. No. 14/180,978 titled "Systems, Computer Medium and Computer-Implemented Methods for Monitoring and Improving Health and Productivity of Employees" filed Feb. 14, 2014.

International Preliminary Report on Patentability for International Application No. PCT/US2012/045395, dated Jan. 7, 2014. (pp. 1-12).

International Preliminary Report on Patentability for International Application No. PCT/US2012/045401, dated Jan. 7, 2014. (pp. 1-9).

International Preliminary Report on Patentability for International Application No. PCT/US2012/045407, dated Jan. 7, 2014. (pp. 1-8).

International Preliminary Report on Patentability for International Application No. PCT/US2012/045410, dated Jan. 7, 2014. (pp. 1-8).

International Preliminary Report on Patentability for International Application No. PCT/US2012/045414, dated Jan. 7, 2014. (pp. 1-8).

International Preliminary Report on Patentability for International Application No. PCT/US2012/045419, dated Jan. 7, 2014. (pp. 1-11).

International Preliminary Report on Patentability for International Application No. PCT/US2012/045427, dated Jan. 7, 2014. (pp. 1-10).

International Preliminary Report on Patentability for International Application No. PCT/US2012/045435, dated Jan. 7, 2014. (pp. 1-10).

International Preliminary Report on Patentability for International Application No. PCT/US2012/045452, dated Jan. 7, 2014. (pp. 1-9).

International Preliminary Report on Patentability for International Application No. PCT/US2012/045447, dated Jan. 7, 2014. (pp. 1-8).

International Preliminary Report on Patentability for International Application No. PCT/US2012/045442, dated Jan. 7, 2014. (pp. 1-10).

Centers for Disease Control and Prevention, 2011, "Chronic diseases and health promotion", [online] Availableat: http://www.cdc.gov/chronicdisease/ overview, [Accessed Feb. 2, 2011].

International Search Report and Written Opinion for International Application No. PCT/US2012/045427, dated Dec. 3, 2012, pp. 1-14.

International Search Report and Written Opinion for International Application No. PCT/US2012/045419, dated Dec. 6, 2012, pp. 1-16.

International Search Report and Written Opinion for International Application No. PCT/US2012/045395, dated Dec. 3, 2012, pp. 1-16.

International Search Report and Written Opinion for International Application No. PCT/US2004/045442, dated Nov. 7, 2012, pp. 1-14.

International Search Report and Written Opinion for International Application No. PCT/US2012/045452, dated Dec. 3, 2012, pp. 1-14.

"Research programs—Philips Research", retrieved from <http://www.research.philips.com/programs/index.html>, May 7, 2012. (pp. 1-2).

"Speedy Assessment | Chiropractic Assessment and Patient Education", retrieved from <http://speedyassessment.com/>, May 7, 2012. (pp. 1-3).

"Stress Thermometer", retrieved from <http://www.biof.com/onlinestore/stressthermometer.asp?redirect=yes>, May 7, 2012. (pp. 1-4).

"Biofeedback—MayoClinic.com", retrieved from <http://www.mayoclinic.com/health/biofeedback/MY01072>, May 7, 2012. (pp. 1-2).

(56) References Cited

OTHER PUBLICATIONS

Abstract for "Psychosocial job factors and symptoms from the locomotor system—a multicausal analysis", retrieved from <http://www.ncbi.nlm.nih.gov/pubmed/1962160>, May 7, 2012. (p. 1).

Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).

Index for "Micro-NanoMechatronics and Human Science (MHS), 2010 International Symposium Nov. 2010", retrieved from <http://ieeexplore.ieee.org/xpl/mostRecentIssue.jsp?punumber=5658189>Ma 7, 2012. (pp. 1-5).

"Wireless measurement devices—Philips", retreved from <http://www.healthcare.philips.com/us_en/products/telehealth/Products/devices.wpd>, May 7, 2012. (pp. 1-2).

"Philips Research Technology Backgrounder—MyHeart project", retrieved from <http://www.research.philips.com/technologies/heartcycle/myheart-gen.html>, May 7, 2012. (pp. 1-3).

"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).

"Philips Research—Download Pictures", retrieved from <http://www.research.philips.com/downloads/pictures/healthcare-personal.html>, May 7, 2012. (pp. 1-2).

"RJL Systems, Products", retrieved from <http://www.rjlsystems.com/products.shtml>, May 7, 2012. (p. 1).

"MomToBe: The Pregnancy Assistant 3.0", retreved from <http://3d2f.com/programs/4-230-momtobe-the-pregnancy-assistant-download.shtml>, Jun. 11, 2012. (pp. 1-2).

"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).

"WorkPace : RSI Injury Prevention Software, Stretch Break Exercise Reminder Software", retrieved from <http://www.workpace.com/>, Sep. 14, 2012. (p. 1).

"Workrave", retrieved from <http://www.workrave.org/>, Sep. 14, 2012. (p. 1).

"Office Athlete Software Prevents Common Repetitive Stress Injuries", retrieved from <http://www.officeathlete.com/>, Sep. 14, 2012. (pp. 1-2).

"Cardinus Risk Management | Ergonomic & DSE Risk Assessments", retrieved from <http://www.cardinus.com/>, Sep. 12, 2012. (pp. 1-2).

"Kinect—Xbox.com", retrieved from <http://www.xbox.com/en-US/kinect>, Jun. 11, 2012. (pp. 1-3).

"Augmented Reality", retrieved from <http://en.wikipedia.org/wiki/Augmented_reality>, May 30, 2012. pp. (1-18).

"Electroencephalography (EEG)", retieved from <http://www.emedicinehealth.com/script/main/art.asp?articlekey-59319&pf=3&page=1>, Jun. 11, 2012. (pp. 1-4).

"Emotiv|EEG System|Electroencephalography", retrieved from <www.emotiv.com/index.asp>, Jun. 11, 2012. (pp. 1-2).

"EmotivEPOC Software Devlopment Kit", retrieved from <www.emotiv.com/store/hardware/epoc-bci-eeg/developer-neuroheadset/>, Jun. 11, 2012. (pp. 1-2).

Chapman, Larry S. MPH, "Meta-evaluation of Worksite Health Promotion Economic Return Studies: 2005 Update", Jul./Aug. 2005. (pp. 1-11).

"OSHA Ergonomic Solutions: Computer Workstations eTool—Checklists", retrieved from <www.osha.gov/SLTC/etools/computerworkstations/checklist.html>, Jun. 11, 2012. (pp. 1-5).

"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).

"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).

"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).

"OSHA Ergonomic Solutions: Computer Workstations eTool—Workstations eTool", retrieved from <www.osha.gov/SLTC/etools/computerworkstations/index.html>, Jun. 11, 2012. (p. 1).

"The Wellness Imperative, Creating More Effective Organizations", World Economic Forum, 2010. (pp. 1-20).

Berry, Leonard et al., "What's the Hard Return on Employee Wellness Programs?", Harvard Business Review, Dec. 2010. (pp. 1-10).

"Pulse Oximetry" SparkFun Electronics, Oct. 7, 2005. (p. 1).

International Search Report & Written Opinion for International Application No. PCT/US2012/045447, dated Jan. 18, 2013. (pp. 1-12).

International Search Report & Written Opinion for International Application No. PCT/US2012/045407, dated Jan. 23, 2013. (pp. 1-15).

International Search Report & Written Opinion for International Application No. PCT/US2012/045401, dated Feb. 5, 2013. (pp. 1-13).

International Search Report & Written Opinion for International Application No. PCT/US2012/045435, dated Jan. 25, 2013. (pp. 1-14).

International Search Report & Written Opinion for International Application No. PCT/US2012/045410, dated Jan. 31, 2013. (pp. 1-13).

International Search Report & Written Opinion for International Application No. PCT/US2012/045414, dated Mar. 25, 2013. (pp. 1-13).

Copending U.S. Appl. No. 13/540,028 titled "Systems, Computer Medium and Computer-Implemented Methods for Monitoring and Improving Cognitive and Emotive Health of Employees", filed Jul. 2, 2012.

Copending U.S. Appl. No. 13/540,067 titled "Computer Mouse System and Associated, Computer Medium and Computer-Implemented Methods for Monitoring and Improving Health and Productivity of Employees", filed Jul. 2, 2012.

Copending U.S. Appl. No. 13/540,095 titled "Chair Pad System and Associated, Computer Medium and Computer-Implemented Methods for Monitoring and Improving Health and Productivity of Employees", filed Jul. 2, 2012.

Copending U.S. Appl. No. 13/540,124 titled "Floor Mat System and Associated, Computer Medium and Computer-Implemented Methods for Monitoring and Improving Health and Productivity of Employees", filed Jul. 2, 2012.

Copending U.S. Appl. No. 13/540,153 titled "Systems, Computer Medium and Computer-Implemented Methods for Monitoring and Improving Biometric Health of Employees", filed Jul. 2, 2012.

Copending U.S. Appl. No. 13/540,180 titled "Systems, Computer Medium and Computer-Implemented Methods for Monitoring and Improving Biomechanical Health of Employees", filed Jul. 2, 2012.

Copending U.S. Appl. No. 13/540,208 titled "Systems, Computer Medium and Computer-Implemented Methods for Coaching Employees Based Upon Monitored Health Conditions Using an Avatar", filed Jul. 2, 2012.

Copending U.S. Appl. No. 13/540,335 titled "Systems, Computer Medium and Computer-Implemented Methods for Providing Health Information to Employees Via Augmented Reality Display", filed Jul. 2, 2012.

Copending U.S. Appl. No. 13/540,374 titled "Systems, Computer Medium and Computer-Implemented Methods for Monitoring Health and Ergonomic Status of Drivers of Vehicles", filed Jul. 2, 2012.

Copending U.S. Appl. No. 13/540,262 titled "Systems, Computer Medium and Computer-Implemented Methods for Monitoring and Improving Health and Productivity of Employees", filed Jul. 2, 2012.

Final Office Action for co-pending U.S. Appl. No. 13/540,335 dated Nov. 6, 2014.

"Footrests—Adjustable Footrest Solutions for the Office", Ergo in Demand, Aug. 20, 2009, pp. 1-4, Ergo in Demand Inc., www.ergoindemand.com/footrest.html.

(56) References Cited

OTHER PUBLICATIONS

Berger et al., "Investing in Healthy Human Capital", Journal of Occupational Environmental Medicine vol. 45, No. 12, dated Dec. 2003; pp. 1213-1225.
Brown et al., "Prowess Proactive Wellness Environment Support System", Dec. 10, 2009, pp. 1-19, www.hsi.gatech.edu/onsitecenter/index.php/PROWESS.
Campbell et al., "The Rise of People-Centric Sensing", IEEE Computer Society, 2008, pp. 12-21, IEEE.
Georgia Tech, "Prowess Proactive Wellness Environment Support System", Dec. 12, 2009, pp. 1-27, www.hsi.gatech.edu/onsitecenter/index.php/PROWESS.
Goetzel et al., "Estimating the Return-on-Investment From Changes in Employee Health Risks on The Dow Chemical Company's Health Care Costs", Journal of Occupational Environmental Medicine vol. 47, No. 8, dated Aug. 2005; pp. 759-768.
Goetzel et al., "Health, Absence, Disability, and Presenteeism Cost Estimates of Certain Physical and Mental Health Conditions Affecting U.S. Employers", Journal of Occupational Environmental Medicine vol. 46, No. 4, dated Apr. 2004; pp. 398-412.
Goetzel et al., "Second-Year Results of an Obesity Prevention Program at The Dow Chemical Company", Journal of Occupational Environmental Medicine vol. 52, No. 3, dated Mar. 2010; pp. 291-302.
Goetzel et al., "The Health and Productivity Cost Burden of the "Top 10" Physical and Mental Health Conditions Affecting Six Large U.S. Employers in 1999", Journal of Occupational Environmental Medicine vol. 45, No. 1, dated Jan. 2003; pp. 5-14.
Goetzel et al., "The Long-Term Impact of Johnson & Johnson's Health & Wellness Program on Employee Health Risks", Journal of Occupational Environmental Medicine vol. 44, No. 5, dated May 2002; pp. 417-424.
Goetzel et al., "The Relationship Between Modifiable Health Risks and Health Care Expenditures: An Analysis of the Multi-Employer HERO Health Risk and Cost Database", Journal of Occupational Environmental Medicine, vol. 40, No. 10; pp. 1-30.
Goetzel et al., "The Workforce Wellness Index", Journal of Occupational Environmental Medicine vol. 55, No. 3, dated Mar. 2013; pp. 272-279.
Goetzel et al., "The Predictive Validity of the HERO Scorecard in Determining Future Health Care Cost and Risk Trends", Journal of Occupational Environmental Medicine vol. 56, No. 2, dated Feb. 2014; pp. 136-144.
Kelly et al., "The Novartis Health Index: A Method for Valuing the Economic Impact of Risk Reduction in a Workforce" Journal of Occupational Environmental Medicine vol. 52, No. 5, dated May 2010; pp. 528-535.
Prochaska et al., "The Well-Being Assessment for Productivity", Journal of Occupational Environmental Medicine vol. 53, No. 7, dated Jul. 2011; pp. 735-768.
Slater et al., "Taking Steps: The Influence of a Walking Technique on Presence in Virtual Reality", ACM Transactions on Computer-Human Interaction, Sep. 1995, pp. 201-219, vol. 2 No. 3.
Sullivan, "Making the Business Case for Health and Productivity Management", Journal of Occupational Environmental Medicine vol. 46, No. 6 suppl, dated Jun. 2004; pp. S56-S61.
World Economic Forum, "The Workplace Wellness Alliance-Making the Right Investment: Employee Health and the Power of Metrics" dated Jan. 2013; pp. 1-36.
USPTO Communication for U.S. Appl. No. 13/540,262, dated Apr. 9, 2014. (pp. 1-56).
USPTO Communication for U.S. Appl. No. 13/540,153, dated Apr. 9, 2014. (pp. 1-50).
USPTO Communication for U.S. Appl. No. 13/540,180, dated Apr. 9, 2014. (pp. 1-49).
USPTO Communication for U.S. Appl. No. 13/540,335, dated Apr. 25, 2014. (pp. 1-48).
Final Office Action for co-pending U.S. Appl. No. 13/540,095 dated Jan. 16, 2015.
Final Office Action for co-pending U.S. Appl. No. 13/540,153 dated Jan. 23, 2015.
Final Office Action for co-pending U.S. Appl. No. 13/540,180 dated Jan. 23, 2015.
Final Office Action for co-pending U.S. Appl. No. 13/540,262 dated Jan. 22, 2015.
Office Action for co-pending U.S. Appl. No. 13/540,028 dated Mar. 5, 2015.
"Statement in accordance with the Notice from the European Patent Office dated Oct. 1, 2007 concerning business methods" Nov. 1, 2007, 1 page, XP002456414.
EPO: "Notice from the European Patent Office dated Oct. 1, 2007 concerning business methods" Official Journal EPO, vol. 30, No. 11, Nov. 1, 2007, pp. 592-593, XP007905525.
International Search Report and Written Opinion for PCT/US2014/056427 dated Apr. 22, 2015.
International Search Report and Written Opinion for PCT/US2014/069498 dated Apr. 1, 2015.
Kymissis et al. "Parasitic Power Harvesting in Shoes" Digest of Papers, Second International Symposium on Wearable Computers, Pittsburgh, PA, Oct. 19-20, 1998, pp. 132-139, XP032385438.
Nintendo Wii Fit, https://www.youtube.com/watch?v=-Taruqvk30E, May 11, 2008.
Anonymous: "Automated analyser"—Wikipedia, Jan. 16, 2015; https: ex.php?title=Automated_analyser&oldid=642687889 retrieved on Feb. 8, 2017; XP055343828 (pp. 1-4).
Hacker, et al. "Representation and visualization of variability in a 3D anatomical atlas using the kidney as an example." Medical Imaging. International Society for Optics and Photonics, 2006. XP055342027 (pp. 1-7).
International Search Report and Written Opinion for International Application No. PCT/US2016/064518; International Filing Date Dec. 2, 2016; Report dated Feb. 17, 2017; (pp. 1-16).
International Search Report and Written Opinion for International Application No. PCT/US2016/065042; International Filing Date Dec. 6, 2016; Report dated Mar. 17, 2017; pp. 1-15.
International Search Report and Written Opinion for International PCT application PCT/US2016/064520; International Filing Date Dec. 2, 2016; Report dated Mar. 27, 2017; (SA5352/PCT); pp. 1-10.
International Search Report and Written Opinion for International PCT application PCT/US2016/064521; International Filing Date Dec. 2, 2016; Report dated Mar. 20, 2017; pp. 1-17.
Stephens: "I am 38. My heart is only 33, but my lungs are aged 52. Why?" Mail Online; http://www. dailymail.co.uk/health/article-1249009/I-38-My-heart-only33-lungs-aged-52-Why.html; retrieved on Feb. 3, 2017; XP055342045 (pp. 1-7).
"40 Best Companies for Leaders—2014" Chief Executive, available as of Dec. 13, 2015 at the website: http://chiefexecutive.net/40-best-companies-for-leaders-2014/; pp. 1-3.
Amato, Neil, "Top 20 companies for leadership development" CGMA Magazine, Sep. 23, 2013; available as of Dec. 13, 2015 at the website: http://www.cgma.org/magazine/news/pages/20138765.aspx?TestCookiesEnabled=redirect; pp. 1-5.
Asplund, Christopher L, et al. "A central role for the lateral prefrontal cortex in goal-directed and stimulus-driven attention." Nature neuroscience 13.4 (2010): 507-512.
Asplund, Christopher L., et al. "The attentional blink reveals the probabilistic nature of discrete conscious perception." Psychological science 253 (2014): 824-831.
Borah, J. "Conceptual modeling-The missing link of simulation development." Proceedings of the 2002 Spring Simulation Conference. 2002. AEgis Technologies Group; pp. 1-7.
Burkus, David, "For Leaders, Looking Healthy Matters More than Looking Smart" Harvard Business Review, Jan. 2, 2015; available as of Dec. 13, 2015 at the website: https://hbr.org/2015/01/for-leaders-looking-healthy-matters-more-than-looking-smart.
Duke, Sean, "A 'smartphone' based defibrillator" Science Spin, Jan. 11, 2011: pp. 1-2.
Dux, Paul E, and René Marois. "The attentional blink: A review of data and theory." Attention, Perception, & Psychophysics 71.8 (2009): 1683-1700.

(56) References Cited

OTHER PUBLICATIONS

Dux, Paul E, et al. "Training improves multitasking performance by increasing the speed of information processing in human prefrontal cortex." Neuron 63.1 (2009): 127-138.

Electric double-layer capacitor Wikipedia; available at the website: http://en.wikipedia.org/wiki/electric_double-layer_capacitor as of Dec. 5, 2014; pp. 1-8.

Elliott, Stephen N., et al. "Cognitive load theory: Instruction-based research with applications for designing tests." Proceedings of the National Association of School Psychologists' Annual Convention, Boston, MA, February vol. 24. 2009.

Fadel, Charles, et al. "Multimodal Learning Through Media: What the Research Says" Cisco Systems, Inc. (2008) pp. 1-24.

Fadjo, Cameron L., et al. "Pedagogy and Curriculum for Video Game Programming Using Scratch." Institute for Learning Technologies, Teachers College, Columbia University, New York, NY, presented at the Scratch Conference, Aug. 13, 2010; pp. 1-2.

Filmer, Hannah L., et al. "Disrupting prefrontal cortex prevents performance gains from sensory-motor training." The Journal of Neuroscience 33.47 (2013): 18654-18660.

Fougnie, Daryl, and René Marais. "What limits working memory capacity? Evidence for modality-specific sources to the simultaneous storage of visual and auditory arrays." Journal of Experimental Psychology: Learning, Memory, and Cognition 37.6 (2011): 132.

Hill, Jr., Randall W.; "How Virtual Humans Can Build Better Leaders" Harvard Business Review Jul. 25, 2014; pp. 1-4.

Horseman, Samantha, et al.; "Gamefication of Health, Safety and the Environment {HSE): An Avatarial Solution" American Society of Safety Engineers 11th Professional Development Conference & Exhibition, Bahrain, Mar. 2014;pp. 1-10.

Ivanoff, Jason, Philip Branning, and René Marois. "fMRI evidence for a dual process account of the speed-accuracy tradeoff in decision-making." PLoS one 3.7 (2008): e2635. pp. 1-14.

Jamison, Dean T., et al.; "The World Health Report 1999" World Health Organization, WHO Library Cataloguing in Publication Data, 1999; pp. 1-136.

Knikou, Maria. "The H-reflex as a probe: pathways and pitfalls." Journal of neuroscience methods 171.1 (2008): 1-12.

Lamkin, Paul; "The best VR headsets: Oculust Rift, PlayStation VR, Gear VR, HTC Vive . . . virtual reality is back baby" 10 Sep. 16, 2015; available as of Dec. 21, 2015 at the website: http://www.wearable.com/headgear/the-best-ar-and-vrheadsets;pp. 1-1.

Marois, René, and Jason Ivanoff. "Capacity limits of information processing in the brain." Trends in cognitive sciences 9.6 (2005): 296-305.

Moreno, Roxana, and Alfred Valdez. "Cognitive load and learning effects of having students organize pictures and words in multimedia environments: The role of student interactivity and feedback." Educational Technology Research and Development 53.3 (2005.

Moreno, Roxana, and Richard Mayer. "Interactive multimodal learning environments." Educational Psychology Review 193 (2007): 309-326.

Moreno, Roxana. "Learning in high-tech and multimedia environments." Current directions in psychological science 15.2 (2006): 63-67.

Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp.

Nintendo of America Inc., Wii Balance Board Operations Manual, 2008, pp. 1-10.

Nintendo of America Inc., Wii Fit Instruction Booklet, 2008, pp. 1-28.

Ovans, Andrea; "What Resilience Means, and Why it Matters" Harvard Business Review Jan. 5, 2015; pp. 1-6.

Qlik Technology Partners available as of Oct. 21, 2015 at the website: http://www.qlik.com/us/partners/technologypartners;pp. 1-21.

Quick, James Campbell, et al. "Executive health: Building strength, managing risks"Academy of Management Executive, May 2000, vol. 14, No. 2, pp. 33-45.

Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-entures-and-eric-schmidt-urban.

Raybourn, Elaine M., et al. "Adaptive thinking & leadership simulation game training for special forces officers." ITSEC 2005 Proceedings, Interservice/Industry Training, Simulation and Education Conference Proceedings, Nov. 2005.

Ready, Douglas A., et al.; "Are You a High Potential?" Harvard Business Review Jun. 2010; pp. 1-13.

Rimor, Rikki, Yigal Rosen, and Kefaya Naser. "Complexity of social interactions in collaborative learning: The case of online database environment." Interdisciplinary Journal of E-Learning and Learning Objects 6.1 (2010): 355-365.

Rosen, Yigal. "The effects of an animation-based on-line learning environment on transfer of knowledge and on motivation for science and technology learning." Journal of Educational Computing Research 40.4 (2009): 451-467.

Seligman, Martin E.P., "Building Resilience" Harvard Business Review from the Apr. 2011 issue; available as of Dec. 13, 2015 at the website: https://hbr.org/2011/04/building-resilience; pp. 1-15.

Simmonds, Bethany, et al. "Objectively assessed physical activity and subsequent health service use of UK adults aged 70 and over: A four to five year follow up study." PLoS one 9.5 (2014): e97676.

Spisak, Brian R., et al., "A face for all seasons: Searching for context-specific leadership traits and discovering a general preference for perceived health" Frontiers in Human Neuroscience; Nov. 5, 2014; available as of Dec. 13, 2015 at the web.

Veeva Systems and Zinc Ahead Join Forces available as of Oct. 2, 2015 at the website: http://www.veeva.com; pp. 1-6.

Wang, Xiaoning. "An Empirical Study of Optimizing Cognitive Load in Multimedia Integrated English Teaching." Studies in Literature and Language 93 (2014): 70.

Agarabi, Mina, et al., "A sEMG-based Method for Assessing the Design of Computer Mice" 26th Annual International Conference of the IEEE EMBS, Sep. 1-5, 2004; pp. 2450-2453.

Robertini, Nadia, et al., "Capture of Arm-Muscle Deformations using a Depth-Camera" 10 European Conference on Visual Media Production, London, UK, Nov. 6-7, 2013; pp. 1-10.

\* cited by examiner

SYSTEMS, COMPUTER MEDIUM AND COMPUTER-IMPLEMENTED METHODS FOR MONITORING HEALTH OF EMPLOYEES USING MOBILE DEVICES

RELATED APPLICATIONS

This application claims the benefit of U.S. Provisional Patent Application No. 61/664,387 filed on Jun. 26, 2012 and titled "SYSTEMS, COMPUTER MEDIUM AND COMPUTER-IMPLEMENTED METHODS FOR MONITORING HEALTH OF EMPLOYEES USING MOBILE DEVICES", U.S. Provisional Patent Application No. 61/504,638 filed on Jul. 5, 2011 and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831 filed on Jun. 14, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790 filed on Jun. 14, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796 filed on Jun. 14, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800 filed on Jun. 14, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807 filed on Jun. 14, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810 filed on Jun. 14, 2012 and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818 filed on Jun. 14, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. Provisional Patent Application No. 61/659,824 filed on Jun. 14, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. Provisional Patent Application No. 61/664,399 filed on Jun. 26, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", and U.S. Provisional Patent Application No. 61/664,414 filed on Jun. 26, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES", the disclosures of which are each hereby incorporated by reference in their entireties.

FIELD OF INVENTION

The present invention relates generally to health monitoring and more particularly to systems, machines, non-transitory computer medium having computer program instructions stored thereon, and computer-implemented methods for monitoring the health of employees.

BACKGROUND OF THE INVENTION

A major concern among employers is the issue of presenteeism, or the phenomena that, while employees may be at work, health problems such as, lower back pain, fatigue, high blood pressure and obesity, keep them from working optimally, and cause a rapid rise in employee healthcare costs. Many human resource ("HR") executives consider presenteeism a problem in their companies, estimating an annual cost to companies of over $180 billion/year, and a per employee cost between $22 and $157 annually. Moreover, presenteeism appears to be a problem at over 50% of workplaces. In 2006, 56% of HR executives viewed it as a problem, while only 39% of HR managers found it to be a problem in 2004. Because such health problems may be caused by a combination of employee lifestyle and work practices, workplace health programs have been employed to make employees aware of sound health and ergonomic practices in an effort to promote employee health and help lower employer costs.

Unfortunately, even if employees are made aware of sound health and ergonomic practices, employees often slip back into poor health and ergonomic practices while engrossed in their day-to-day work activities. The current state of the art solution to address these issues includes health programs that rely on periodic tests to assess employee health and ergonomics. Such tests typically require employees to expend a great deal of effort to participate in the health programs. For example, health programs may monitor the employee's health via test conducted in test facilities at discrete testing times (e.g., quarterly or annual health tests). Traditional testing systems may not be suitable for these environments due to their size and complexity. Thus, existing health programs may require the employee to take time out of their day to attend a health test, existing health programs may not assess the employee in their day-to-day work environment (e.g., while the employee is situated in their day-to-day work environment, such as on a worksite, at their desk working on their computer or traveling there between), and existing health programs may not provide continuous feedback that can be used to dynamically adjust the employee's day-to-day activities and/or may not be able to rapidly identify and predict health issues based on ongoing changes in the employee's health.

SUMMARY OF THE INVENTION

Applicant has recognized several shortcomings of existing health programs, and, in view of these shortcomings, has recognized the need for a health monitoring system that continuously monitors the employees' health in their day-to-day work environments. Applicant has recognized that, although existing health programs provide some level of health monitoring, the complexities associated with employees having to proactively take part in health tests may reduce employee involvement in the health programs. For example, employees may decide to forgo a health program in view of the time and effort required to engage in health tests at a testing facility. Moreover, Applicant has recognized that the infrequent nature of the health tests may inhibit the ability of existing health programs to promptly identify and predict health issues (e.g., health risks such as injury or disease). For example, semi-annual tests may not be able to identify changes in the employee's health that can occur over days or weeks, such as illness, short term injuries, and diseases that manifest themselves over a short period of time. Thus, existing health programs fail to provide a framework for continuously acquiring health data that can be used to rapidly identify changes in the employee's health. Applicant has recognized that such shortcomings have failed to be addressed by others, and has recognized that such shortcomings may be addressed by a system that can continuously collect employee health data while employees are situated in their day-to-day work environment (e.g., at a remote worksite, at their desks or traveling there between), that can process the health data to assess the employees' current health and predict health issues, and that can provide feedback indicative of the employees' current health conditions and predicted health issues. Such a system may help to reduce the effort required by employees to take part in a health program while also enabling employees to take proactive measures to address their current health conditions and prevent the predicted health issues based on feedback that includes current health conditions and predicted health issues. In view of the foregoing, various embodiments of the present invention advantageously provide systems, machines, non-transitory computer medium having computer program instructions stored thereon, and computer-implemented methods for monitoring the health of employees in their work environments using mobile devices, such as portable computers, tablet computers, mobile telephones phones (e.g., cellular phones) and the like, for determining employee health profiles (e.g., including existing or predicted health conditions/risks and health plans to guide the employee with regard to a healthy lifestyle) based on the health data, and for providing feedback to communicate the determined health profile and associated information.

In some embodiments, provided is a system to monitor an employee's health while in a work environment. The system including a communications network, a health database connected to the communications network and storing health information for one or more employees, a set of one or more health sensors configured to collect health data from the employee including at least one of: a set of one or more biometric sensors configured to sense biometric characteristics of the employee and output biometric data corresponding to the sensed biometric characteristics of the employee and a set of one or more biomechanic sensors configured to sense biomechanic characteristics of the employee and output biomechanic data corresponding to the sensed biomechanic characteristics of the employee. The set of one or more biometric sensors including at least one of a temperature sensor configured to output temperature data indicative of a body temperature of the employee, a blood condition sensor configured to output blood condition data indicative of a blood oxygenation level of the employee, a blood pressure sensor configured to output blood pressure data indicative of a blood pressure of the employee, a body fat sensor configured to output body fat data indicative of a body fat of the employee, a respiration sensor configured to output respiration data indicative of a respiration rate of the employee, a neural sensor configured to output neural data indicative of brain activity of the employee, a force sensor configured to output force data indicative of a body weight of the employee, a position sensor configured to output position data indicative of a body position of the employee, and a camera sensor configured to output image data indicative of a biometric characteristic of the employee. The set of one or more biomechanic sensors including at least one of a neural sensor configured to output neural data indicative of brain activity of the employee, a camera sensor configured to output image data indicative of a biomechanic characteristics of the employee, a force sensor configured to output force data indicative of a force exerted by the employee, and a position sensor configured to output position data indicative of a body position of the employee. The system including a mobile communications device connected to the communications network and being configured to collect the health data from the set of one or more health sensors and output health data corresponding to the health data collected from the set of one or more health sensors. The mobile communications device including at least one of the one or more health sensors integrated therein to sense at least one biometric or biomechanic characteristic for the employee. The system including a health server connected to the communications network and being configured to receive, via the communications network, health data output by the mobile communications device, determine, based at least in part on the received health data, a health profile for the employee including at least one of health characteristics, health conditions, health risks and health plans for the employee determined based at least in part on the received health data, update the health information stored in the health database to reflect the health profile for the employee, and serve, to the mobile communications device for display to the user via a graphical display of the mobile communications device, health report content including at least one of the health characteristics, the health conditions, the health risks and the health plans of the health profile for the employee.

In some embodiments, the at least one of the set of one or more health sensors integrated within the mobile communication device includes a sensor pad including one or more conductive contacts configured to sense at least one biometric or biomechanic characteristic of the employee via physical contact between skin of the employee and the one or more conductive contacts.

In certain embodiments, the at least one of the set of one or more health sensors integrated within the mobile communication device includes a body fat sensor including a sensor pad having two conductive contacts physically integrated within a body of the mobile communication device and configured to be grasped by the employee's right and left hands during use. The mobile communications device being configured to take a resistance measurement across the two conductive contacts while the two conductive contacts are grasped by the employee's right and left hands such that the resistance measurement is indicative of a body fat of the employee across the employee's right and left hands. The health data collected by the mobile communications device including body fat data indicative of the resistance measurement.

In some embodiments, the at least one of the set of one or more health sensors integrated within the mobile communication device includes a body temperature sensor including a sensor pad having a conductive contact configured to contact the employee's hand during use. The mobile communications device being configured to take a temperature measurement from the conductive contact while the conductive contact is grasped by the employee's hand such that the temperature measurement is indicative of a body temperature of the employee. The health data collected by the mobile communications device including temperature data indicative of the temperature measurement.

In certain embodiments, the at least one of the set of one or more health sensors integrated within the mobile communication device includes a sensor screen configured to sense at least one biometric or biomechanic characteristic of the employee via physical contact between skin of the employee and the sensor screen.

In some embodiments, the sensor screen includes a touch screen configured collect at least one of a finger print and a hand print of the employee while the screen is contacted by the user's finger or hand. The employee's identify being verified (e.g., by the server) based at least in part on the at least one of a finger print and hand print collected via the touch screen of the mobile communication device.

In certain embodiments, the at least one of the set of one or more health sensors integrated within the mobile communication device includes a temperature sensor including a thermal imaging camera configured to acquire thermal image data indicative of the body temperature of the employee. The health data collected by the mobile communications device including temperature data corresponding to the thermal image data indicative of the body temperature of the employee.

In some embodiments, the at least one of the set of one or more health sensors integrated within the mobile communication device includes a temperature sensor including an infrared (IR) sensor configured to acquire IR data indicative of the body temperature of the employee. The health data collected by the mobile communications device including temperature data corresponding to the IR data indicative of the body temperature of the employee.

In certain embodiments, the at least one of the set of one or more health sensors integrated within the mobile communication device includes a position sensor including a camera configured to acquire image data indicative of the body position of the employee. The health data collected by the mobile communications device including position data corresponding to the image data indicative of the body position of the employee.

In some embodiments, one or more of the health sensors includes at least one or more remote sensors in communication with the mobile communication device. The at least one or more remote sensors including of at least one of a temperature sensor configured to output temperature data indicative of a body temperature of the employee, a blood condition sensor configured to output blood condition data indicative of a blood oxygenation level of the employee, a blood pressure sensor configured to output blood pressure data indicative of a blood pressure of the employee, a body fat sensor configured to output body fat data indicative of a body fat of the employee, a respiration sensor configured to output respiration data indicative of a respiration rate of the employee, a neural sensor configured to output neural data indicative of brain activity of the employee, a force sensor configured to output force data indicative of a body weight of the employee or force exerted by the employee, a position sensor configured to output position data indicative of a body position of the employee, and a camera sensor configured to output image data indicative of at least one of a biometric or biomechanic characteristic of the employee. The at least one or more remote sensors being configured to transmit, to the mobile communications device, the respec-tive temperature data, blood pressure data, body fat data, respiration data, neural data, force data, position data, and image data.

In certain embodiments, the at least one or more remote sensors being configured to transmit, to the mobile communications device, the respective temperature data, blood pressure data, body fat data, respiration data, neural data, force data, position data, and image data output via a wireless connection between the at least one or more remote sensors and the mobile communications device.

In some embodiments, the health profile includes at least one of a body temperature, a body weight, a body fat, a heart rate, a blood pressure, a blood oxygenation level, a respiration rate, brain activity, a body position, eye movement, and physical exertion for the employee determined based at least in part on the received health data.

In certain embodiments, the health profile includes at least one of a risk of obesity, a risk of injury, a risk of diabetes, a risk of infection, a risk of inflammation, a risk of circulation problems, a risk of cardio vascular disease, a risk of cardio vascular accidents, a risk of illness, a risk of asthma, a risk of allergies, a risk of bronchitis, a risk of musculoskeletal syndrome, a risk of carpal tunnel syndrome, a risk of epicondylitis, a risk of rotator cuff injury, a risk of eye disease, and a risk of physical fatigue determined based at least in part on the received health data.

In some embodiments, the mobile communications device includes at least one of a cellular phone, a personal digital assistant (PDA), and tablet computer.

In certain embodiments, the health profile for the employee includes one or more predicted health issues, and serving the health report content includes serving content indicative of the one more predicted health issues such that the employee is alerted to the one or more predicted health issues and is afforded an opportunity to address the one or more predicted health issues prior to the one or more predicted health issues escalating into an actual health issue.

In some embodiments, provided is a system for monitoring the health of an employee. The system including a set of one or more health sensors configured to be provided on or near the employee while the employee is engaged in their work duties and being configured to output health data corresponding to characteristics sensed by the sensor. The one or more health sensors including at least one or more biometric sensors configured to sense biometric characteristics of the employee and biomechanic sensors configured to sense biomechanic characteristics of the employee. The system including a mobile communications device including at least one of the one or more health sensors integrated therein to sense at least one biometric or biomechanic characteristic for the employee and being configured to collect the health data from the set of one or more health sensors. The health data collected being used to determine a health profile for the employee including at least one of health characteristics, health conditions, health risks and health plans for the employee determined based at least in part on the health data collected The mobile communications device also being configured to display, via a graphical user interface of the mobile communications device, a health report including at least one of the health characteristics, the health conditions, the health risks and the health plans of the health profile for the employee determined based at least in part on the health data collected.

In certain embodiments, one or more of the set of one or more health sensors is located in at least one of a safety helmet, work gloves, work footwear, or work clothing worn by the employee while the employee is engaged in their work duties.

In some embodiments, one or more of the health sensors includes one or more remote sensors in communication with the mobile communication device. The one or more remote sensors including of at least one of a temperature sensor configured to output temperature data indicative of a body temperature of the employee, a blood condition sensor configured to output blood condition data indicative of a blood oxygenation level of the employee, a blood pressure sensor configured to output blood pressure data indicative of a blood pressure of the employee, a body fat sensor configured to output body fat data indicative of body fat of the employee, a respiration sensor configured to output respiration data indicative of a respiration rate of the employee, a neural sensor configured to output neural data indicative of brain activity of the employee, a force sensor configured to output force data indicative of a body weight of the employee or force exerted by the employee, a position sensor configured to output position data indicative of a body position of the employee, and a camera sensor configured to output image data indicative of at least one of a biometric or biomechanic characteristic of the employee The at least one or more remote sensors being configured to transmit, to the mobile communications device, the respective temperature data, blood pressure data, body fat data, respiration data, neural data, force data, position data, and image data output.

In some embodiments, the at least one of the one or more health sensors integrated with the mobile communications device includes at least one of a sensor pad, a sensor screen, a thermal camera and an infrared (IR) sensor.

In certain embodiments, the health profile for the employee includes one or more predicted health issues, and the displayed health report includes content indicative of the one more predicted health issues such that the employee is alerted to the one or more predicted health issues and is afforded an opportunity to address the one or more predicted health issues prior to the one or more predicted health issues escalating into an actual health issue.

In certain embodiments, provided is a non-transitory computer readable storage medium including program instructions for monitoring an employee's health while in a work environment. The computer program instructions being executable by a computer processor to cause the steps of receiving, via a communications network, health data output by a mobile communications device. The mobile communications device being connected to the communications network, being configured to collect the health data from a set of one or more health sensors and output health data corresponding to the health data collected from the set of one or more health sensors, and including at least one of the one or more health sensors integrated therein to sense at least one biometric or biomechanic characteristic for the employee. The set of one or more health sensors including at least one of a set of one or more biometric sensors configured to sense biometric characteristics of the employee and output biometric data corresponding to the sensed biometric characteristics of the employee and a set of one or more biomechanic sensors configured to sense biomechanic characteristics of the employee and output biomechanic data corresponding to the sensed biomechanic characteristics of the employee. The set of one or more biometric sensors including at least one of a temperature sensor configured to output temperature data indicative of a body temperature of the employee, a blood condition sensor configured to output blood condition data indicative of a blood oxygenation level of the employee, a blood pressure sensor configured to output blood pressure data indicative of a blood pressure of the employee, a body fat sensor configured to output body fat data indicative of a body fat of the employee, a respiration sensor configured to output respiration data indicative of a respiration rate of the employee, a neural sensor configured to output neural data indicative of brain activity of the employee, a force sensor configured to output force data indicative of a body weight of the employee, a position sensor configured to output position data indicative of a body position of the employee, and a camera sensor configured to output image data indicative of a biometric characteristic of the employee. The set of one or more biomechanic sensors including at least one of a neural sensor configured to output neural data indicative of brain activity of the employee, a camera sensor configured to output image data indicative of a biomechanic characteristics of the employee, a force sensor configured to output force data indicative of a force exerted by the employee, and a position sensor configured to output position data indicative of a body position of the employee. The steps also including determining, based at least in part on the received health data, a health profile for the employee including at least one of health characteristics, health conditions, health risks and health plans for the employee determined based at least in part on the received health data, updating health information stored in a health database to reflect the health profile for the employee, and serving, to the mobile communications device for display to the user via a graphical display of the mobile communications device, health report content including at least one of the health characteristics, the health conditions, the health risks and the health plans of the health profile for the employee.

In some embodiments, provided is a computer implemented method for monitoring the health of an employee. The method including collecting health data from a set of one or more health sensors provided on or near the employee while the employee is engaged in their work duties and being configured to output health data corresponding to characteristics sensed by the health sensors. The one or more health sensors including at least one or more biometric sensors configured to sense biometric characteristics of the employee and biomechanic sensors configured to sense biomechanic characteristics of the employee. At least one of the one or more health sensors being integrated within a mobile communications device. The health data collected being used to determine a health profile for the employee including at least one of health characteristics, health conditions, health risks and health plans for the employee determined based at least in part on the health data collected. The method including displaying, via a graphical user interface of the mobile communications device, a health report including at least one of the health characteristics, the health conditions, the health risks and the health plans of the health profile for the employee determined based at least in part on the health data collected.

In certain embodiments, provided is a computer implemented method for monitoring the health of an employee. The method including collecting, via one or more mobile communications devices, health data from a set of one or more health sensors provided on or near the employee while the employee is engaged in their work duties. The one or more health sensors configured to output health data corresponding to characteristics sensed by the health sensors. The one or more health sensors including at least one or more biometric sensors configured to sense biometric characteristics of the employee and biomechanic sensors configured to sense biomechanic characteristics of the employee. The method including determining a health profile for the employee using the health data collected. The health profile including at least one of health characteristics, health conditions, health risks and health plans for the employee determined based at least in part on the health data collected. The method also including and providing for display via a graphical user interface of via at least one of the one or more mobile communications devices, a health report including at least one of the health characteristics, the health conditions, the health risks and the health plans of the health profile for the employee determined based at least in part on the health data collected.

Accordingly, as described herein below, embodiments of the system, computer program instructions and associated computer-implemented methods allow for monitoring of the employee's health using mobile devices.

BRIEF DESCRIPTION OF THE DRAWINGS

So that the manner in which the features and advantages of the invention, as well as others, which will become apparent, may be understood in more detail, a more particular description of the invention briefly summarized above may be had by reference to the embodiments thereof, which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

Figure 1:
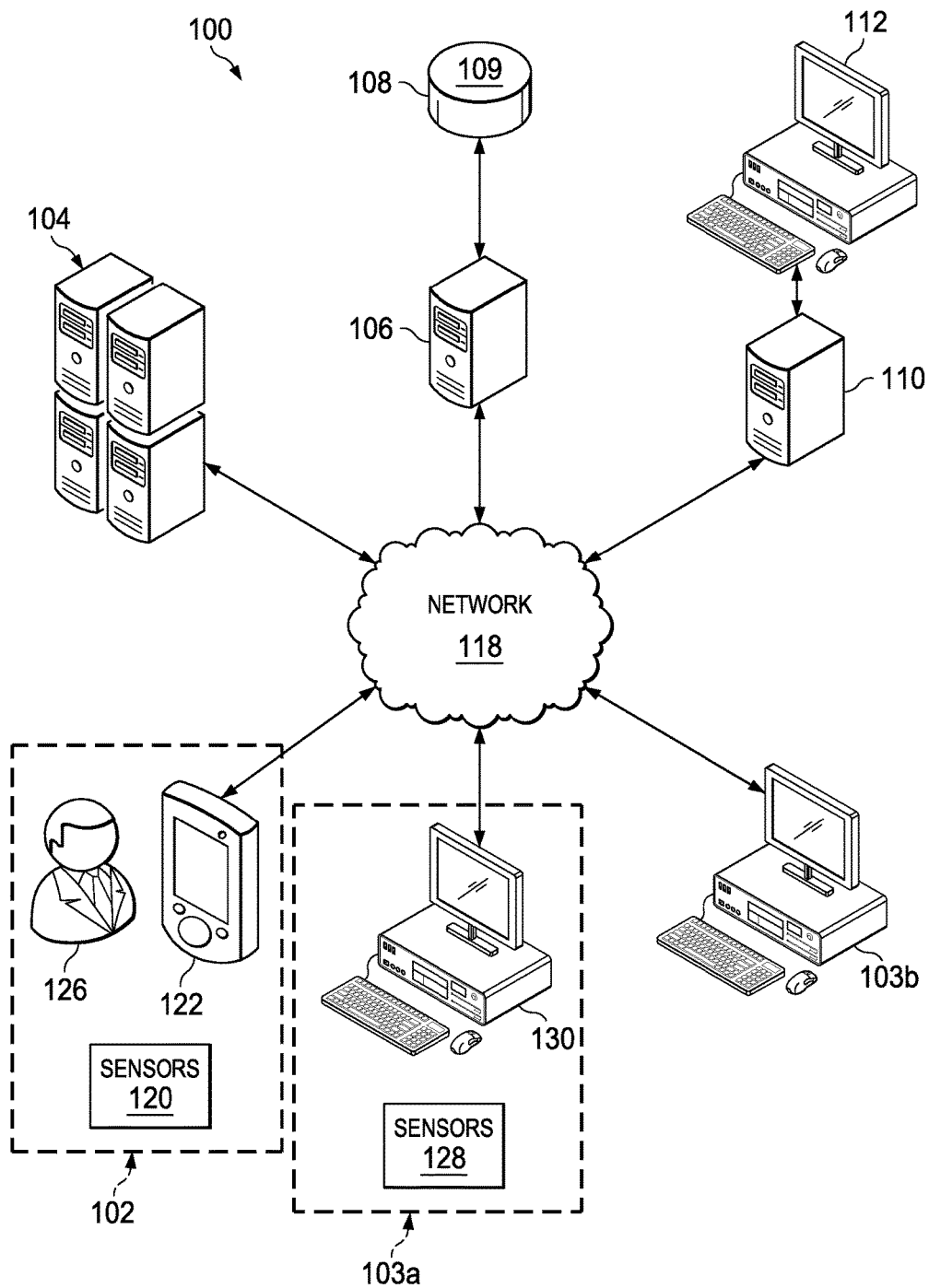
FIG. 1 is a block diagram that illustrates an employee heath monitoring system in accordance with one or more embodiments of the present invention.

The present invention will now be described more fully hereinafter with reference to the accompanying drawings in which exemplary embodiments of the invention are shown. This invention may, however, be embodied in many different forms and should not be construed as limited to the illustrated embodiments set forth herein; rather, these exemplary embodiments are provided so that this disclosure will be thorough and complete, and will fully convey the scope of the invention to those skilled in the art.

In some embodiments, provided is a mobile employee health monitoring system that provides for monitoring of an employee's health, that provides feedback to the employee and other interested parties (e.g., an employer) regarding the current status of the employee's health, that provides the employee with information to guide the employee in a healthy lifestyle, and that provides the employee with reinforcing information to encourage the employee to continue to engage in the healthy lifestyle. Such a mobile health monitoring system may enable monitoring of the employee's health in their office, at a remote worksite and while traveling there between.

In certain embodiments, monitoring of the employee's health includes monitoring the employee while they are engaged in their day-to-day work activities within their work environment. In some embodiments, various monitoring devices (e.g., health sensors) are provided to collect health data that can be used to assess various biometric and biomechanic characteristics (e.g., characteristics, conditions and risks) of the employee, such as the employee's body weight, body temperature, body fat percentage, heart rate, blood pressure, blood glucose level, blood oxygenation level, body position/posture, eye fatigue, neural activity, emotions, thoughts, facial movements/expressions, motor skills, physical exertion, and the like.

In certain embodiments, the monitoring devices are provided on or about the employee (e.g., in their clothing) or integrated within a mobile device carried by the employee (e.g., sensors integrated within a cellular phone, personal digital assistant ("PDA"), tablet computer, or the like) such that the employee's health can be monitored in various locations without requiring the employee to visit a test facility to take part in a health test/exam. In certain embodiments, the mobile device is used to collect measurements from the various sensors. In some embodiments, for example, the employee may have multiple sensors disposed about their body (e.g., temperature sensor, blood pressure sensor, heart rate sensor, etc.) and the employee's cellular phone may collect measurements from the sensors (e.g., via Bluetooth wireless communication). In certain embodiments, the mobile device may process the collect measurements locally and/or forward corresponding health data to a remote server. In some embodiments, for example, the employee's cellular phone may forward the collected health data to a health server (e.g., via a cellular communications network) for processing. In certain embodiments, the health data may be processed to assess the employee's health. In some embodiments, for example, the health data may be used to generate a health profile/report for the employee.

In some embodiments, the health data collected and/or the health characteristics/conditions identified can be used to predict health issues and/or identify corresponding health risks for the employee, such as risks for obesity, injury, diabetes, infection, circulation problems, cardiovascular disease, cardiovascular accidents (e.g., stroke or heart attack), back injury, eye disease, depression, fatigue, and/or the like. In certain embodiments, health risks are determined via predictive analytics that use employee's current and/or historical health characteristics/conditions. For example, where the recent health data for an employee indicates a trend of increasing body weight for an employee, it may be predicted that the employee is at risk for becoming obese within a given time period. In some embodiments, an alert may be provided to the employee to make them aware of the predictions/risks. For example, the employee may be presented with a listing of risks that correspond to predicted health issues. Such predictions and corresponding alerts may enable the employee to proactively improve their health before the associated risks escalate to a critical level. For example, as a result of a prediction and alert that communicates to the employee that they are at risk for becoming obese, the employee may have the motivation needed to change their eating and exercise habits to avoid actually becoming obese. Thus, the system may provide an environment for proactively predicting and responding to health risks before they escalate into actual health conditions.

In some embodiments, the health data, characteristics, conditions and/or risks are used to generate one or more health plans for the employee. In certain embodiments, the health plans include preventative health plans that provide guidance to reduce health risks and/or promote a healthy lifestyle. In some embodiments, the health plans provide a suggested nutrition plan and/or a suggested exercise regime. In certain embodiments, the employee health monitoring system provides coaching (e.g., suggestions) to help the employee follow through with the health plan. In some embodiments, the health data, characteristics, conditions and/or plans may be logged over time to generate a health profile for the employee.

In some embodiments, the employee health monitoring system provides for automated health testing based on a predetermined schedule. In certain embodiments, for example, automated health test may be executed continuously (e.g., constantly from 8 am to 5 pm) or at regular intervals (e.g., hourly from 8 am to 5 pm). Such embodiments may enable the employee's health to be monitored passively, with little to no effort by the employee. In some embodiments, the employee health monitoring system provides for manually initiated health testing. In certain embodiments, for example, an employee may select to initiate a health test. Such embodiments may enable employees to take a more active role in the monitoring of their health.

In some embodiments, the results of the health tests are provided to the employee for review. In certain embodiments, for example, the health monitoring system provides a health report including the employee's health profile information (e.g., the health data collected, the health characteristics/conditions, and/or the health risks for the employee). In some embodiments, the health report is accessible by the employee via their mobile device (e.g., via a health status widget, an interactive dashboard, and/or the like) such that the employee can view the results at their convenience throughout the workday. Such embodiments may enable the employee to receive real-time feedback regarding their health and immediately make corresponding adjustments throughout the workday. In some embodiments, the results of the health tests are provided to an employer or other interested parties (e.g., a physician) for review. Such embodiments may enable the employer to monitor the health of some or all of their employees such that they can readily identify health concerns/trends and take action to alleviate those concerns/trends to improve the health environment for the employees.

In some embodiments, the health monitoring system monitors the health profile information to identify whether the employee is experiencing a health crisis (e.g., a stroke or heart attack) and, in the instance the employee is experiencing a health crisis, generates corresponding alerts. In certain embodiments, for example, upon determining that the employee is having a heart attack based on the results of a health test, the health monitoring system may forward an alert to emergency response personnel (e.g., police, fire, emergency medical technicians ("EMT's") or the like). Such embodiments may help to ensure that the employee receives prompt medical treatment in the event of a medical emergency at the workplace.

Embodiments of the health monitoring system may provide a work environment that promotes employee involvement in monitoring their health via a non-intrusive health testing environment that enables the employee's health to be monitored from the convenience of their workstation. Moreover, embodiments of the health monitoring system may provide feedback that informs the employee of their current health, that predicts/identifies health issues/risks and goals based on the employee's health and provides guidance to reduce the employee's health risk and attain the identified health goals.

FIG. 1 is a block diagram that illustrates an employee heath monitoring system ("system") 100 in accordance with one more embodiments of the present invention. As depicted, system 100 may include one or more mobile employee health monitoring systems ("mobile health monitoring system") 102, workstations 103 (e.g., one or more employee workstations 103a and employer workstations 103b), a health server ("server") 104, a file server 106 coupled to a datastore 108, and a web server 110 connected to one or more remote workstations 112. In some embodiments, the mobile employee health monitoring system 102 may include one or more health sensors 120 and one or more employee mobile devices ("mobile devices") 122. In some embodiments, the workstations 103a, 103b and 112 may include a networked computer or similar network access terminal. In some embodiments, the entities of the system 100 may be communicatively coupled via a network 118. The datastore 108 may store health information 109 (e.g., personal profile information, health profile information, and/or the like) for one or more employees 126.

In some embodiments, the network 118 may include an element or system that facilitates communications between entities of system 100. For example, the network 118 may include an electronic communications network, such as the Internet, a local area network ("LAN"), a wide area ("WAN"), a wireless local area network ("WLAN"), a cellular communications network, and/or the like. In some embodiments, network 118 may include a single network or combination of networks. For example, employee mobile devices 122, workstations 103, server 104, file server 106, and/or web server 110, may be networked using a private/LAN, with remote workstations 112 (e.g., employee home computers, emergency personnel computer devices, of the like) connected to web server 104 via a WAN. In some embodiments, the employee mobile device 122 may be connected to network 118 via another network node. For example, the mobile device 122 may include a remote device connected to the network 118 via the web server 110.

In some embodiments, the mobile device 122 includes a mobile computing device. For example, the mobile device 122 may include a mobile computer, such as a laptop computer, a tablet computer, a personal digital assistant ("PDA"), a cellular phone, or the like. In some embodiments, the mobile device includes a mobile communications device capable of communicating information via the network 118. For example, the mobile device 122 may be capable of connecting to and/or communicating via a LAN, a WLAN, a cellular network, and/or the like.

As described in more detail below, mobile device 122 may include a device employed to collect employee health data for use in monitoring an employee's health. In some embodiments, the mobile device 122 may collect measurements from one or more health sensors ("sensors") 120. The mobile device 122 may forward health data corresponding to the sensed measurements to health server 104 for use in monitoring the employee's health. For example, the server 104 may generate a health profile for employee 126 (e.g., health characteristics, conditions, risks, plans, and/or the like for the employee) using the health data collected via the sensors 120 and the mobile device 122 of the mobile health monitoring system 102. In some embodiments, the mobile device 122 may be employed to display information relating to the health profile for the employee. For example, the mobile device 122 may display a heath report including some or all of the health profile information for the employee such that employee may receive feedback relating to their health. Such a mobile health monitoring system 102 may provide for monitoring the health of the employee while they work in or travel between various work environments. For example, such a mobile health monitoring system 102 may enable the collection of health data while the employee is working in the field (e.g., on worksite such as an oil and gas production platform, a manufacturing plant, a refinery, a construction site, and/or the like), when they are situated in a fixed work environment (e.g., an employee's office employee's office, cubicle, assigned station on an assembly/manufacturing line, or the like), and/or when they are traveling (e.g. traveling between worksites, driving a delivery truck, and/or the like).

Although some embodiments are described with regard to a health profile based on health data collected from the mobile health monitoring system 102, other embodiments may include a health profile based on health data collected from any variety of sources as will be understood by those skilled in the art. For example, where the employee 126 has an employee workstation 103a in a in a fixed work environment (e.g., an employee's office employee's office, cubicle, assigned station on an assembly/manufacturing line, or the like) including an employee computer 130 and/or health sensors 128 for collecting health data from the employee while they are at or near the workstation 103a) and/or other mobile devices 122 (e.g., a cellular phone, a tablet computer, a laptop computer, a PDA and/or the like), the server 104 may employ the health data collected via the employee workstation 103a, the other mobile devices, and/or the mobile health monitoring system 102, and/or the like for use in generating the health profile for the employee. Thus, for example, the health data collected via the health sensors 128 of the workstation 103a may be used to monitor the employee's health while the employee is located at the workstation 103a, and the health data collected via the health sensors 120 of the mobile health monitoring system 102 and/or other mobile devices 122; may be used to monitor the employee's health while the employee is not located at the workstation 103a (e.g., traveling or working offsite).

In some embodiments, the health data may include measurements that can be used to assess various biometric aspects of the employee's health, such as one or more of body temperature, body weight, body fat, heart rate, respiratory rate, blood pressure, blood oxygen saturation ("blood oxygenation"), blood glucose level, neural/brain activity, and/or the like. In some embodiments, the health data may include measurements that can be used to assess various biomechanic aspects of the employee's health, such as one or more of body position, posture, muscle tension, eye fatigue, facial expression, motor skills, and/or the like. Sensors that are used to acquire measurements for use in assessing various biometric aspects of the employee's health may be referred to as "biometric sensors". Sensors that are used to acquire measurements for use in assessing various biomechanic aspects of the employee's health may be referred to as "biomechanic sensors". Sensors that provide are used to acquire measurements for use in assessing both biometric and biomechanic aspects of the employee's health may be referred to as "biometric" and/or "biomechanic" sensors.

As discussed in more detail below, in some embodiments, the mobile device 122 may provide for collecting health data from the various sensors 120 and/or forwarding corresponding health data to the server 104 for use in monitoring an employee's health. For example, in response to determining that employee's health data needs to be collected (e.g., based on a request from the server 104, based on a request from the employee, a predetermined test schedule, or the like), the mobile device 122 may monitor the sensors 120 to collect health data (e.g., collect measurements) from the sensors 120, and may forward corresponding health data to the server 104 for use in monitoring the health of the employee. Although certain embodiments are described herein with regard to the mobile device 122 collecting the health data measurements and forwarding corresponding health data to server 104, in other embodiments, some or all of the health data may be provided directly to the server 104 (i.e., without having to pass the data through the mobile device 122). For example, sensors 120 may be communicatively coupled to the network 118 (e.g., via a WLAN) such that they can transmit heath data directly to the server 104 via the network 118.

Figure 2:
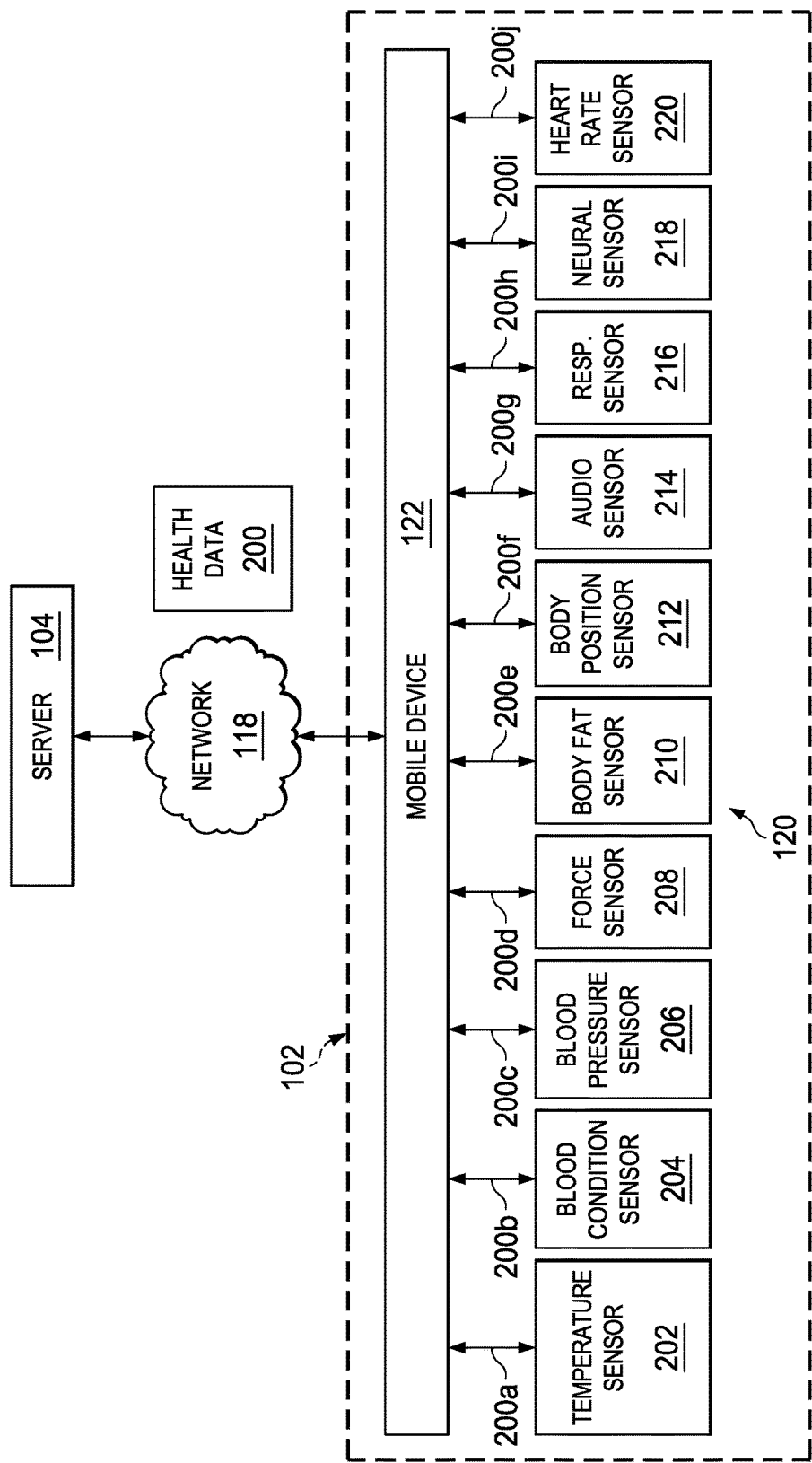
FIG. 2 is a block diagram that illustrates a mobile health monitoring system connected to a server via a network in accordance with one or more embodiments of the present invention.

FIG. 2 is a block diagram that illustrates a mobile health monitoring system 102 connected to the server 104 via the network 118 in accordance with one or more embodiments of the present invention. In some embodiments the mobile health monitoring system 102 includes the employee's mobile device 122 communicatively coupled to one or more of the sensors 120 for collecting employee health data 200. For example, the employee's mobile device 102 may be communicatively coupled to one or more temperature sensors (e.g., thermocouples, IR sensors, etc.) 202, one or more blood condition sensors (e.g., pulse oximeters) 204, one or more blood pressure sensors (e.g., a blood pressure cuff) 206, one or more force sensors (e.g., force transducers) 208, one or more body fat sensors (e.g., conductive contacts) 210, one or more body position sensors (e.g., three-dimensional ("3 D") image/video camera) 212, one or more audio sensors (e.g., microphone) 214, one or more respiration sensors 216, one or more neural sensors 218, one or more heart rate sensors 220 (e.g., a heart rate monitor) and/or the like for collecting corresponding health data 200 (e.g., health measurements) therefrom. In some embodiments, the health data 200 may include temperature data 200a, blood condition data 200b, blood pressure data 200c, force data 200d, body fat data 200e, body position data 200f, audio data 200g, respiration data 200h, neural data 200i and/or heart rate data 200j, collected from the corresponding sensors 120. The health data 200 may be provided to the server 104 for use in monitoring the employee's health.

In some embodiments, the mobile device 122 may be communicatively coupled to the sensors 120 via a wired connection. For example, some or all of the sensors 120 may include a communication cable extending between each of the respective sensors 120 and the mobile device 122. In some embodiments, the mobile device 122 may be communicatively coupled to the sensors 120 via a wireless connection. For example, some or all of the sensors 120 may communicate with the mobile device 122 via a wireless connection (e.g., a Bluetooth connection, a WLAN of network 118, and/or the like). In some embodiments, heath data 200 (e.g., 200a-200j) may be transmitted from the sensors 120 to the mobile device 122 via the wired or wireless connection. In some embodiments, the health data 200 may be transferred between devices of system 100 via a non-transitory storage medium such as a universal serial bus ("USB") memory stick (e.g., a flash drive). For example, the health data 200 acquired from the sensors 120 may be downloaded from the sensors 120 and/or the mobile device 122 to a USB memory stick and may be uploaded from the USB memory stick to another device of system 100, such as the mobile device 122, the employee computer 126, the employer workstation 103b, the remote workstation 112, and/or the sever 104.

Figure 3:
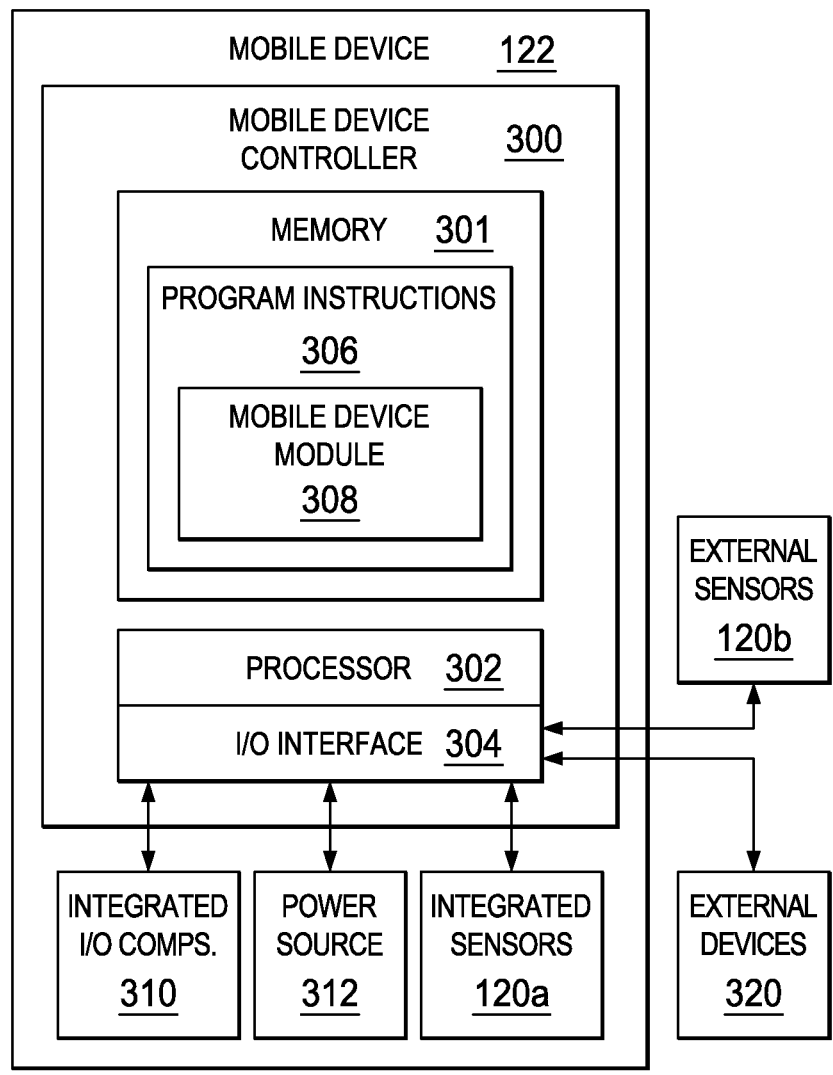
FIG. 3 is a block diagram that illustrates components of a mobile device in accordance with one or more embodiments of the present invention.

FIG. 3 is a block diagram that illustrates components of the mobile device 122 in accordance with one or more embodiments of the present invention. In some embodiments, the mobile device 122 includes a mobile device controller 300 for controlling the operational aspects of the mobile device 122. For example, the mobile device controller 300 may provide for allocating power to integrated devices, collecting health data 200 from the various sensors 120 and/or transmitting the collected health data 200 to the server 104. In some embodiments, the mobile device controller includes a memory 301, a processor 302 and an input/output (I/O) interface 304.

The memory 301 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 301 may include a non-transitory computer readable storage medium having program instructions 306 stored thereon that are executable by a computer processor (e.g., the processor 304) to cause the functional operations (e.g., methods/routines/processes) described herein with regard to the mobile device 122. The program instructions 306 may include a mobile device module 308 including program instructions that are executable by the processor 302 to provide some or all of the functionality described herein with regard to the mobile device 122.

The processor 302 may be any suitable processor capable of executing/performing program instructions. The processor 302 may include a central processing unit (CPU) that carries out program instructions (e.g., of the mobile device module 308) to perform arithmetical, logical, and input/output operations of the mobile device 122, including those described herein.

The I/O interface 304 may provide an interface for connection of one or more I/O devices to the mobile device 122. I/O devices may include integrated I/O components (e.g., buttons, microphone, speaker, graphical display (e.g., a touch screen), cameras, and/or the like) 310, a power source (e.g., battery) 312, integrated sensors 120a, external devices (e.g., server 104) 320, and/or the like. External devices 320 may be connected to I/O interface 304 via a wired or wireless connection. For example, the external devices 320 (e.g., the server 104) may be connected to the I/O interface via wireless connection to the network 118. In some embodiments, the integrated sensors 120a include sensors 120 that are physically integrated with the mobile device 122. For example, as described in more detail below, the integrated sensors 120a may include conductive contacts integrated into the exterior of the mobile device 122 such that a measurement (e.g., temperature measurement, a resistance measurement indicative of body fat, and/or the like) can be acquired via the conductive contacts while the user is grasping the exterior of the mobile device 122. In some embodiments, the external sensors 120a include the sensors 120 that are remote from the mobile device 122. For example, external sensors 120a may include temperature sensors 212, blood pressure sensors 206, or the like that are worn by the employee to take measurements at various locations on the employee's body.

The mobile device 122 may be employed to collect health data 200 from the various sensors 120 (e.g., integrated sensors 120a and/or external sensors 120b) and/or forward corresponding health data 200 to the server 104 for use in monitoring the employee's health. For example, in response to determining that health data 200 (e.g., temperature data 200a, blood condition data 200b, blood pressure data 200c, position data 200d, body fat data 200e, 3D position data 200f, audio data 200g, respiration data 200h, neural data 200i and/or heart rate data 200j) needs to be collected, the mobile device 122 may employ, or otherwise monitor, one or more of the particular sensors 120 capable of sensing/measuring the needed health data 200 such that the needed health data 200 is transmitted from the various sensors 120 to the mobile device 122, the mobile device 122 may collect/store the needed health data 200 (e.g., store/queue the acquired health data 200 in memory 301), and/or the mobile device 122 may forward the health data 200 to server 104 for use in monitoring the employee's health.

In some embodiments, the mobile device 122 may process the raw/acquired health data to generate the corresponding processed health data. For example, where the mobile device 122 receives raw health data (e.g., temperature data 200a including a voltage indicative of a sensed temperature), the mobile device 122 may process the raw health data to generate a corresponding value (e.g., using a look-up table, equation or the like to identify a temperature value corresponding to the voltage) that may be included in the health data 200 transmitted to the server 104. Accordingly, in some embodiments, the health data 200 may include the raw/acquired health data (e.g., a voltage value) and/or the processed health data corresponding thereto (e.g., the temperature value corresponding to the voltage value). Similar processing may be provided for the other types of health data.

In some embodiments, the mobile device 122 may forward the health data 200 as the corresponding health data is received. For example, the mobile device 122 may receive health data 200 from sensors and immediately forward the health data 200 with little to no delay such that a continuous stream of health data 200 is provided to the server 104 for use in monitoring the employee's health. In some embodiments, the mobile device 122 may store (e.g., queue or buffer) the health data 200 for transmission at a later time. For example, where a test routine requires that the mobile device 122 transmit a batch of health data 200 at the end of a test cycle, transmit a batch of health data 200 on a regular interval (e.g., every ten minutes), or the like, the health data 200 received may be stored in memory 301 of the mobile device 122 and may be queued-up or buffered in memory for transmission as a batch of health data 200 to server 104 at the end of the test cycle, at the regular interval, or the like.

In some embodiments, a temperature sensor 202 may include thermocouples, IR sensors, or the like. During use, the temperature sensor 202 may transmit health data 200 indicative of a temperature sensed by the temperature sensor 202 (e.g., a temperature measurement). For example, where a temperature sensor 202 is positioned to acquire the employee's body temperature at a given location (e.g., at their hand, wrist, head, chest or the like), the mobile device 122 may receive, from the temperature sensor 202, the temperature data 200a indicative of the temperature (e.g., 37° C. (98.6° F.)) at the given location.

In some embodiments, a blood condition sensor 204 may include pulse oximeters, blood glucose testing devices, and/or the like. The blood condition sensor 204 may include, for example, the OctiveTech™ 300IH Pulse Oximeter manufactured by Nellcor™ or the BCI™ 3301 Hand Held Pulse Oximeter manufactured by Smiths Medical™. During use, the mobile device 122 may receive health data 200 indicative of blood characteristics sensed by the blood condition sensor 204. For example, where a pulse oximeter is positioned about the employee's fingertip, the mobile device 122 may receive, from the pule oximeter, blood condition data 200b indicative of various aspects of the employee's blood, such as the employee's blood oxygenation level at the employee's fingertip (e.g., 95% oxygenation).

In some embodiments, a blood pressure sensor 206 may include blood pressure cuffs and/or the like. The blood pressure sensor 206 may include, for example, the UA-789PC Extra Large Cuff sold by LifeSource™ and the CMS-08A Professional Upper Arm Blood Pressure Monitor manufactured by CMS™. During use, the mobile device 122 may receive health data 200 indicative of the employee's blood pressure sensed by the blood pressure sensor 206. For example, where a blood pressure cuff is positioned about the employee's wrist/arm, the mobile device 122, may receive, from the blood pressure cuff, blood pressure data 200c indicative of the employee's blood pressure (e.g., 90/60 mmHg) sensed at the employee's wrist/arm.

In some embodiments, a force sensor 208 may include force transducers, such as strain gauges, load cells and/or the like. During use, the mobile device 122 may receive health data 200 indicative of the force sensed by the force sensor 208. For example, where load cells are positioned in the employee's footwear (e.g., in the employee's right and left work boots) and the employee is standing, the mobile device 122 may receive, from the load cells, force data 200d indicative of the forces exerted by the employee's feet. Such force data 200d may be used to calculate a weight of the employee (e.g., 56.5 kg (124.6 lbs.). As a further example, where load cells are positioned in the employee's hand wear (e.g., in the employee's right and left work gloves) and the employee is lifting an object, the mobile device 122 may receive, from the load cell, force data 200d indicative of the forces exerted by the employee's hands. Such force data 200d may be used to determine the weight of an object being lifted and/or the physical exertion by the employee.

In some embodiments, a body fat sensor 210 may include conductive contacts that can be used to sense resistivity in the employee's body tissue and/or the like. During use, the mobile device 122 may receive health data 200 indicative of the employee's body fat sensed by the body fat sensor 210. For example, where conductive contacts are integrated within the right and left sides of the mobile device 122 and the employee grasp the right and left sides of the mobile device with their right and left hands, respectively, such that their hands contact the conductive contacts, the mobile device 122 may receive, from the conductive contacts, body fat data 200e including a resistance measurement across the conductive contacts that is indicative of the body fat of the employee.

In some embodiments, a body position sensor 212 may include a camera (e.g., a two-dimensional still/video camera, a three-dimensional ("3D") still/video camera and/or the like that can be used to sense the employee's body position. During use, the mobile device 122 may receive health data 200 indicative of the physical position of the employee as sensed by the body position sensor 212. For example, where a body position sensor 212 includes a 3D video camera positioned such that the employee's body is within its field of view, the mobile device 122 may receive, from the 3D camera, body position data 200f (e.g., a three-dimensional video image) indicative of the position (e.g., head, arm, hand, torso, leg, and feet position and/or posture) of the employee. In some embodiments, the image/video data may be used to track the eye movement of the employee. For example, where the employee's head is in the field of view of the video camera, the body position data 200f may include images that can be used to track the eye position of the employee, the employee's eye blink rate, the employee's pupil dilatation and/or the like. In some embodiments, a 3D camera may include a device such as the Kinect™ manufactured by Microsoft. Such a 3D camera may include a software development kit that provides for employing the camera as a biomechanical sensor for determining various biometric aspects of the employee, including body position. Though a specific 3D video camera device is described herein, other such cameras may be manufactured that can be adapted for use in the instant system as will be understood by those skilled in the art. For example, any camera may be employed that is capable of capturing 3D body images such that movements may be "sensed" and corresponding data extrapolated for use in monitoring the health of the employee (e.g., via a posture analysis, eye fatigue analysis, etc.).

In some embodiments, a body position sensor 212 may include one or more positioning devices that can be used to locate a relative or absolute position of the employee. For example, where a positioning device is provided in the employee's boots, work gloves, helmet, elbow pads, knee pads, and/or belt, the body position data 200f may include signals and/or coordinates indicative of the location of each of the positioning devices such that a location of the employee's hands, feet, head, elbows, knees, and/or waist can be determined. Such location information may be used to determine the employee's body position, including an analysis of their posture. In some embodiments, the position sensor 212 may include a combination of different types of positions sensors (e.g., a 3D camera, positioning devices, and/or the like) that can be used in combination to determine the employee's body position.

In some embodiments, an audio sensor 214 may include a microphone or the like for acquiring audio data (e.g., words spoken by the employee). During use, the mobile device 122 may receive health data 200 indicative of the audio data sensed by the audio sensor 214. For example, where the audio sensor 214 includes a microphone, the mobile device 122 may receive, from the audio sensor 214, audio data 200g (e.g., an audio feed) indicative of words spoken by the employee.

In some embodiments, respiration sensor 216 may include a device for sensing the employee's respiration rate (e.g., number of breaths taken within a set amount of time, typically sixty seconds. During use, the mobile device 122 may receive health data 200 indicative of the respiration rate ("RR") of the employee sensed by the respiration sensor 216. For example, the mobile device 122 may receive, from the respiration sensor 216, respiration data 200h indicative of number of breaths taken by the employee over sixty seconds (e.g., 15 breaths per minute).

In some embodiments, neural sensor 218 may include a device (e.g., an electrode) for sensing brain activity (e.g., neural activity) of the employee. In some embodiments, the neural sensors 218 may employ electroencephalography ("EEG") to measure neuro-signal voltage fluctuations resulting from ionic current flows within the neurons of the brain. EEG may refer to recording of the brain's spontaneous electrical activity over a short period of time (e.g., twenty-forty minutes) from a plurality of neural sensors 218 disposed on the employee's scalp. For example, a plurality of neural sensor 218 (e.g., sixteen neural sensors/channels) may be disposed about the employee's scalp to detect neuro-signals (e.g., including alpha, beta, gamma, and delta waves) that can be used to determine the employee's brain state, including their emotional state (e.g., happy, sad, excited, etc.), thoughts (e.g., cognitive thoughts, subconscious thoughts, intent, etc.), facial movements (e.g., facial expressions), motor functions and/or the like. In some embodiments, neural sensors 218 include dry electrodes that can be used to sense neuro signals. Such dry electrodes may require minimal or no skin preparation for disposing the contact on the employee's scalp. During use, the mobile device 122 may receive health data 200 indicative of the employee's neural activity sensed by the plurality of neural sensors 218. For example, the mobile device 122 may receive, from the neural sensors 218, neural data 200i indicative of the sensed neuro-signals.

In some embodiments, a heart rate sensor 220 may include a heart rate monitor. During use, the mobile device 122 may receive health data 200 indicative of the employee's heart rate sensed by the heart rate sensor 220. For example, where a heart rate monitor is positioned about the employee's torso, the mobile device 122 may receive, from the heart rate monitor, heart rate data 200j indicative of the employee's hear rate (e.g., 80 beats per minute("BPM")).

In some embodiments, some or all of the sensors 120 may be located at or near the employee (e.g., worn by the employee) 126 and/or physically integrated with the mobile device 122. For example, various ones of the sensors 120 may be provided in the employee's apparel, such as their clothing (e.g., shirt and pants, gloves, etc.), footwear (e.g., work boots), head wear (e.g., a safety helmet), and eyewear (e.g., safety glasses) and/or various ones of the sensors 120 may be located in the mobile device 122.

Figure 4:
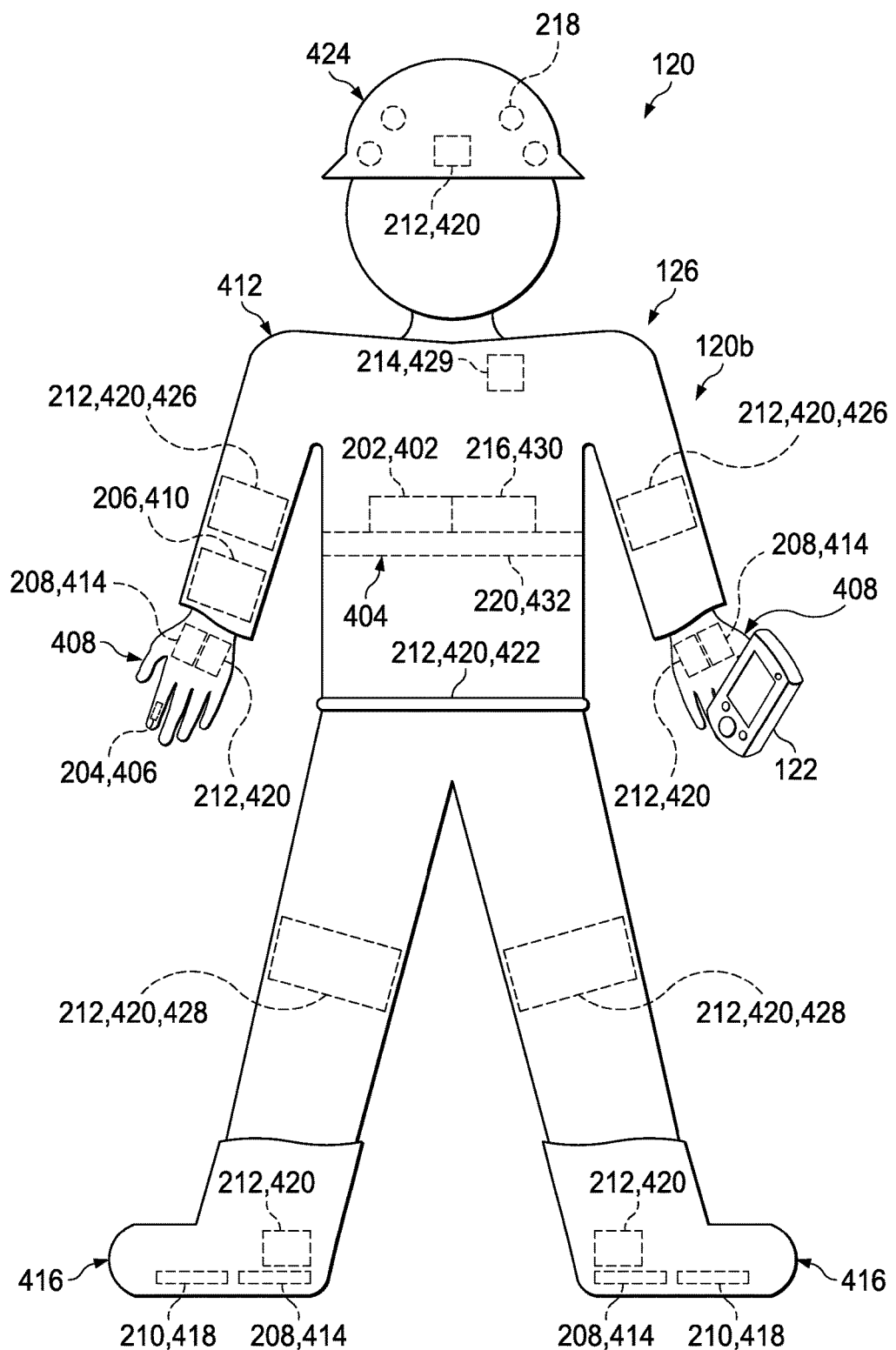
FIG. 4 illustrates an employee wearing various sensors of the mobile health monitoring system in accordance with one or more embodiment of the present invention.

FIG. 4 is a diagram that illustrates the employee 126 wearing various sensors 120 (e.g., external sensors 120b) of the mobile health monitoring system 102 in accordance with one or more embodiment of the present invention. In some embodiments, a temperature sensor 202 is disposed at the employee's chest. For example, the temperature sensor 202 may include a thermometer/thermocouple 402 secured around the employee's torso via a strap 404. Other embodiments may include any number of temperature sensors provided in any number of suitable locations such as the employee's hand, wrist, arms, back, head, feet and/or the like.

In some embodiments, a blood condition sensor 204 is disposed at the employee's finger. For example, the blood condition sensor 204 may include a pulse oximeter 406 integrated with a finger portion of work gloves 408 worn by the employee. Other embodiments may include any number of blood condition sensors provided in any number of suitable locations such as the employee's earlobe, toe and/or the like.

In some embodiments, a blood pressure sensor 206 is disposed at the employee's arm/wrist. For example, the blood pressure sensor 206 may include a blood pressure cuff 410 secured about the employee's wrist. In some embodiments, the blood pressure cuff 410 may be integrated into a sleeve 412 of the employee's shirt. Other embodiments may include any number of blood pressure sensors provided in any number of suitable locations such as the employee's upper-arm and/or the like.

In some embodiments, force sensors 208 are disposed at the employee's hands and/or feet. For example, the force sensors 208 may include force transducers 414 integrated within the palm portion of the work gloves 408 worn by the employee. Such force transducers 214 may enable a determination of a force exerted by the employee's hands (e.g., while lifting an object). As a further example, the force sensors 208 may include force transducers 414 integrated within the sole portion of work boots 416 worn by the employee. Such force transducers 414 may enable a determination of a force exerted on the employee's foot which can, for example, be used to determine the employee's weight. Other embodiments may include any number of force sensors provided in any number of suitable locations such as the employee's back, buttocks area and/or the like.

In some embodiments, body fat sensors 210 are disposed at the employee's feet. For example, the body fat sensors 210 may include conductive contacts 418 integrated within the sole portion of the work boots 416 worn by the employee. The conductive contacts may contact the sole of the employee's feet. Such a body fat sensors 210 may enable a determination of a resistance across the employee's feet that is indicative of their body fat percentage. Other embodiments may include any number of body fat sensors provided in any number of suitable locations such as the employee's hands, chest, back, buttocks area and/or the like.

In some embodiments, body position sensors 212 are disposed at the employee's hands, feet, head, waist, and/or the like. For example, the body position sensors 212 may include positioning devices 420 integrated within the palm portion of the work gloves 408, integrated within the work boots 416, a belt 422, a safety helmet 424, elbow pads 426, and/or knee pads 428 worn by the employee. Such positioning devices 420 may enable a determination of the absolute or relative positions of the employee's hands, feet, waist, head, knees and elbows. Other embodiments may include any number of locations sensors provided in any number of suitable locations such as the employee's torso/chest, back, shoulders, chin, buttocks area and/or the like.

In some embodiments, an audio sensor 214 is provided near the employee's mouth. For example, the audio sensor 214 may include a microphone/speaker 429 secured at or near of the employee's shirt collar. Other embodiments may include any number of audio sensor sensors provided in any number of suitable locations.

In some embodiments, a respiration sensor 216 is disposed at the employee's chest. For example, the respiration sensor 216 may include a respiratory motion sensor 430 secured around the employee's torso via the strap 404. Other embodiments may include any number of respiration sensor sensors provided in any number of suitable locations.

In some embodiments, one or more neural sensors 218 are disposed about the employee's head/scalp. In some embodiments, the helmet 424 includes a plurality of neural sensors 218 (e.g., sixteen neural sensors 218) integrated therein (e.g., coupled to an interior of the helmet such that the contact the employee's head while the employee is wearing the helmet 424). The helmet 424 may provide for positioning of the neural sensors 218 in discrete neural sensor locations about the employee's head while the helmet 424 is being worn by the employee. Other embodiments may include any number of neural sensor sensors provided in any number of suitable locations.

In some embodiments, a heart rate sensor 220 is disposed about the employee's chest. For example, the heart rate sensor 220 may include a heart rate monitor 432 secured around the employee's torso/chest via the strap 404 and including two conductive contacts for sensing the employee's heart rate. Other embodiments may include any number of heart rate sensors provided in any number of suitable locations.

Figure 5:
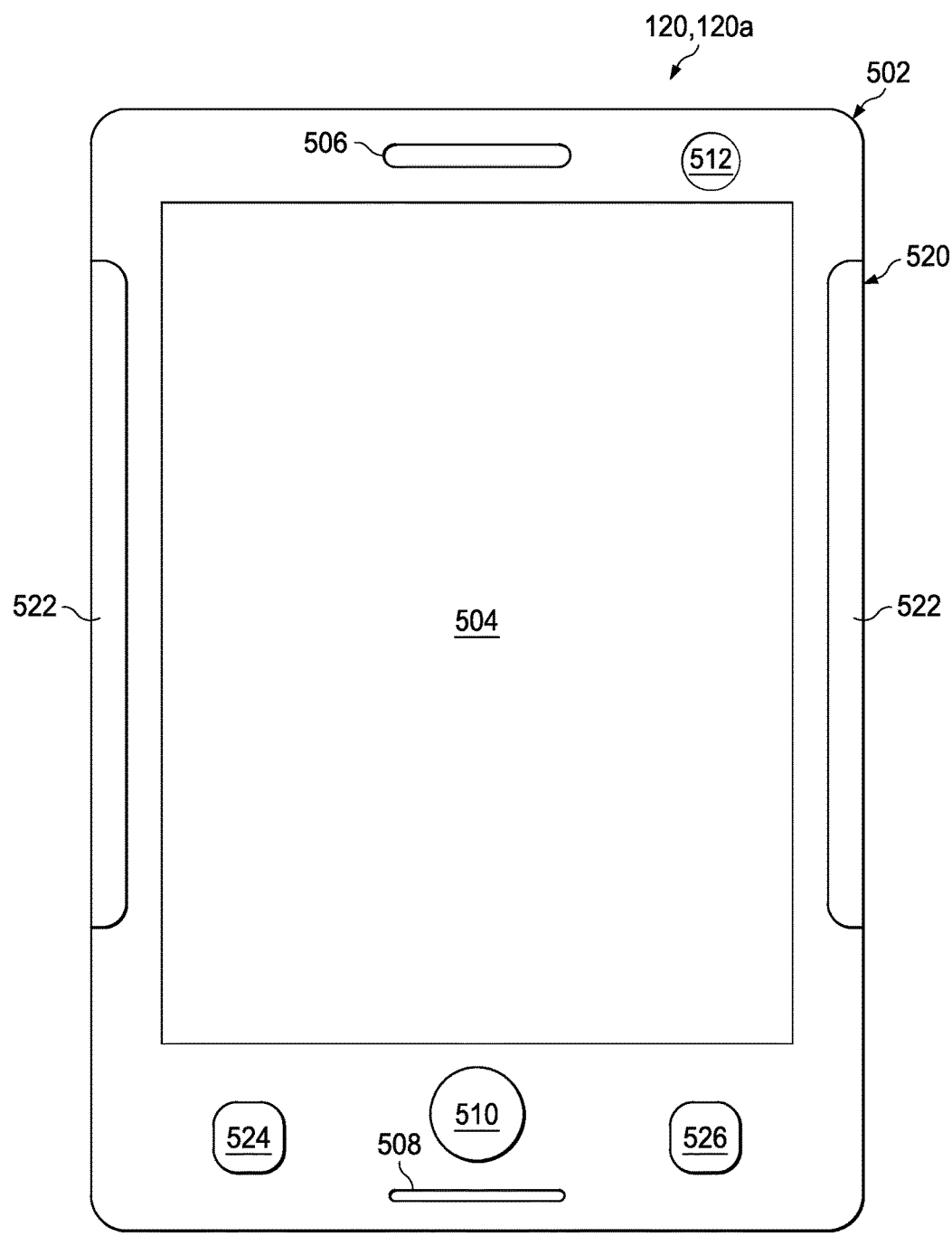
FIG. 5 illustrates a mobile device including a plurality of sensors integrated therein in accordance with one or more embodiments of the present invention.

FIG. 5 is a diagram that illustrates the mobile device 122 including a plurality of sensors 120 integrated therein (e.g., integrated sensors 120a) in accordance with one or more embodiments of the present invention. In some embodiments, the mobile device 122 includes a body 502, a display screen 504 (e.g., a touch screen), a speaker 506, a microphone 508, a selection button 510, and a camera 512.

In some embodiments, the mobile device 122 includes integrated sensors pads 520. The sensor pads 520 may include two conductive contacts 522 (e.g., two metallic pads) disposed on opposite edges of the body 502 of the mobile device 122 such that the user's left hand/palm may contact a first of the conductive pads 522 while grasping the right edge of the mobile device 122 and/or the user's the user's right hand/palm may contact a second of the conductive pads 522 while grasping the left edge of the mobile device 122. Other embodiments may include any number of sensor pads provided in any number of suitable locations such as the front and/or rear of the mobile device 122. In some embodiments, the sensor pads 520 may be employed as a temperature sensor 202 such that the mobile device 122 includes a temperature sensor 202 integrated therewith. For example, when the employee grasps at least one of the conductive contacts 522 with their hand, the temperature of the employee's hand may be sensed and corresponding temperature data 2020a may be provided to the mobile device controller 300. In some embodiments, the sensor pads 520 may be employed as a body fat sensor 210 such that the mobile device 122 includes a body fat sensor 210 integrated therewith. For example, when the employee grasps the right and left conductive pads 522 with their left and right hands, respectively, a resistance measurement may be taken across the employee's hands that is indicative of the body fat percentage of the employee and corresponding body fat data 200e may be provided to the mobile device controller 300.

In some embodiments, the screen 504 of the mobile device 122 includes a sensor screen capable of sensing various biometric and/or biomechanic characteristics of the employee. In some embodiments, the screen 504 may be able to collect biometric information, such as finger and/or hand print information that can be used for verifying the identity of the employee. For example, upon the employee placing their fingertip and/or hand on the screen 504, the screen may acquire an image of the employee's finger print and/or hand print and corresponding biometric health data indicative of the employee's finger print and/or hand print may be provided to the mobile device controller 300.

In some embodiments, the mobile device 122 may include an integrated IR sensor 524 for sensing temperature. During use, the employee may place a portion of their body on or near the IR sensor 524 and/or aim the IR sensor 524 toward the portion of their body such that the IR sensor 524 senses a temperature of the corresponding portion of the employee's body and provides corresponding temperature data 200a to the mobile device controller 300.

In some embodiments, the mobile device 122 may include an integrated pulse oximeter 526 (e.g. a reflectance type pulse oximeter). During use, the employee may place their fingertip on the pulse oximeter 526 such that the pulse oximeter senses the employee's blood oxygenation or similar characteristics and provides corresponding blood condition data 200b to the mobile device controller 300.

In some embodiments, the integrated camera 512 of the mobile device 122 may include a two-dimensional still/video camera, a three-dimensional ("3D") still/video camera and/or the like that is employed as a position sensor such that the mobile device 122 includes a position sensor 212 integrated therewith. For example, the camera 512 may be used to acquire images of the employee and provide corresponding body position data 200f (e.g., a three-dimensional video image) indicative of the position (e.g., head, arm, hand, torso, leg, and feet position and/or posture) of the employee to the mobile device controller 300.

In some embodiments, the integrated microphone 508 of the mobile device 122 may be employed as an audio sensor 214. For example, the microphone 508 may be used to acquire an audio feed of words spoken by the employee and provide corresponding audio data 200g to the mobile device controller 300.

Figure 6:
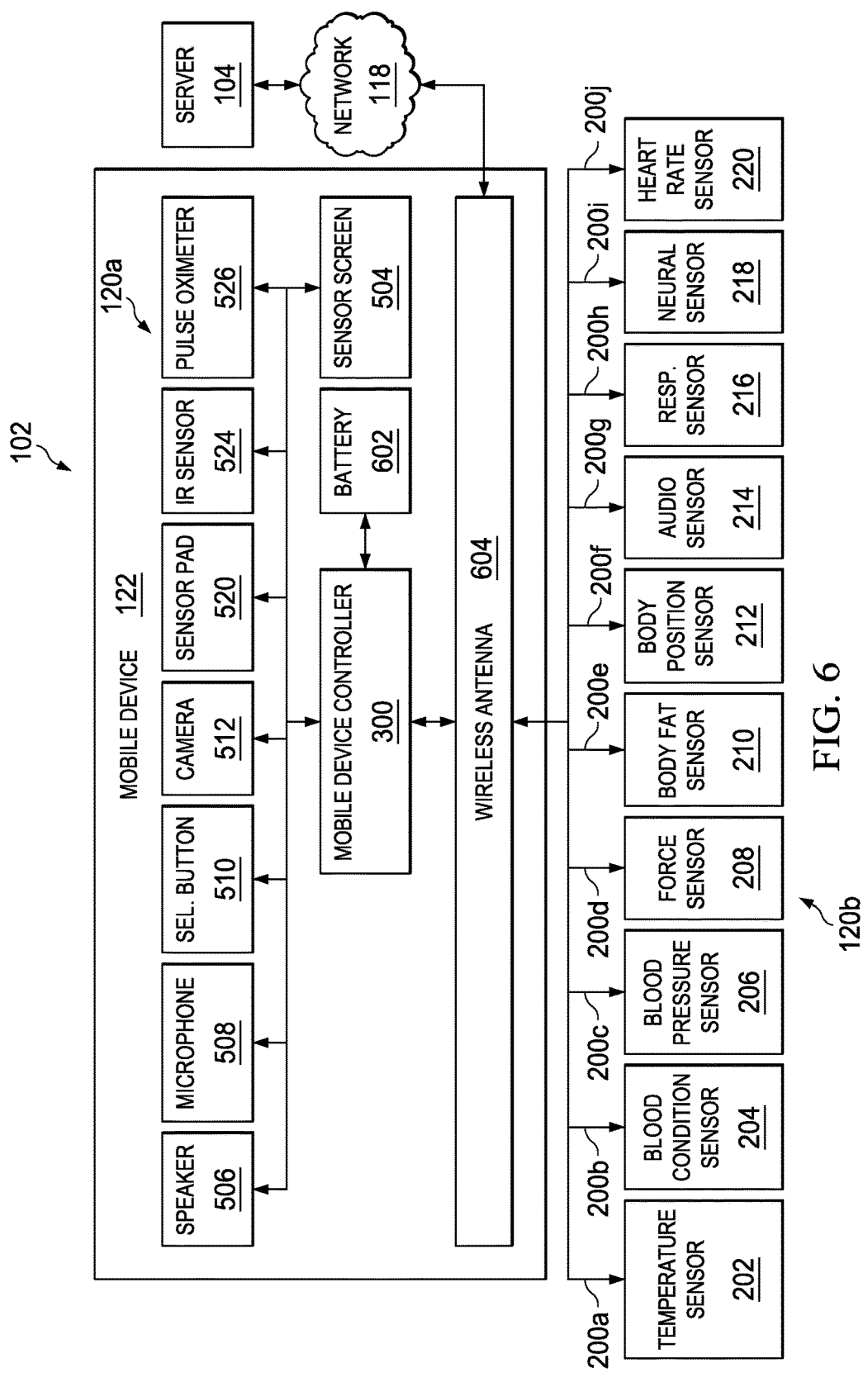
FIG. 6 is a block diagram that illustrates an exemplary mobile health monitoring system in accordance with one or more embodiments of the present invention.

FIG. 6 is a block diagram that illustrates an exemplary mobile health monitoring system 102 in accordance with one or more embodiments of the present invention. The mobile health monitoring system 102 includes the mobile device 122 having the mobile device controller 300 coupled to the display screen (e.g., a sensor screen) 504, the speaker 506, the microphone 508, the selection button 510, the camera 512, the sensors pad 520, the IR sensor 524, pulse oximeter 526, a battery 602, a wireless antenna 604. In some embodiments, the mobile device controller 300 may employ one or more of the integrated sensors 120a (e.g., the display screen 504, the microphone 508, the camera 512, the sensors pads 520, the IR sensor 524, and/or the pulse oximeter 526) and/or one or more of the external sensors 120b (e.g., one or more temperature sensors 202, one or more blood condition sensors 204, one or more blood pressure sensors 206, one or more force sensors 208, one or more body fat sensors 210, one or more body position sensors 212, one or more audio sensors 214, one or more respiration sensors 216, one or more neural sensors 218, and/or one or more heart rate sensors 220) to collect corresponding health data 200 (e.g., temperature data 200a, blood condition data 200b, blood pressure data 200c, force data 200d, body fat data 200e, body position data 200f, audio data 200g, respiration data 200h, neural data 200i and/or heart rate data 200j). For example, the mobile device controller 300 may activate the IR sensor 524 and/or temperature sensor 402 to take a temperature measurement, activate the pulse oximeters 526 and/or 406 to take a blood oxygenation measurement, or the like. To take a body fat measurement, the mobile device controller 300 may induce a current (I) across two conductive contacts 522 of the sensor pad 520 and take a measurement of voltage (V) across the two conductive contacts 522 to determine a resistance (R) across the contacts 522 that is indicative of the body fat for the employee. In some embodiments, the battery 602 may provide power to operate the controller 300 and/or provide the power required to take a measurement from the integrated sensors 120a and/or the external sensors 120b.

In some embodiments, the wireless antenna 604 may include a Bluetooth transceiver, a network transceiver (e.g., WLAN transceiver, cellular transceiver, and/or the like), and/or similar wireless transceiver to enable wireless communication between the mobile device controller 300 and the network 118, between the mobile device controller 300 and the external sensors 120b, and/or the like. For example, as will be understood by those skilled in the art, where external sensors 120b and the wireless antenna 604 include Bluetooth transceivers, the sensors 120b may communicate measurements to the mobile device controller 300 via the wireless antenna 604 using Bluetooth wireless communication protocol. As a further example, where the wireless antenna includes a cellular/WLAN transceiver, the mobile device controller 300 may be able to communicate with the server 104 via the wireless antenna 604 and the cellular/WLAN network 118.

Figure 7:
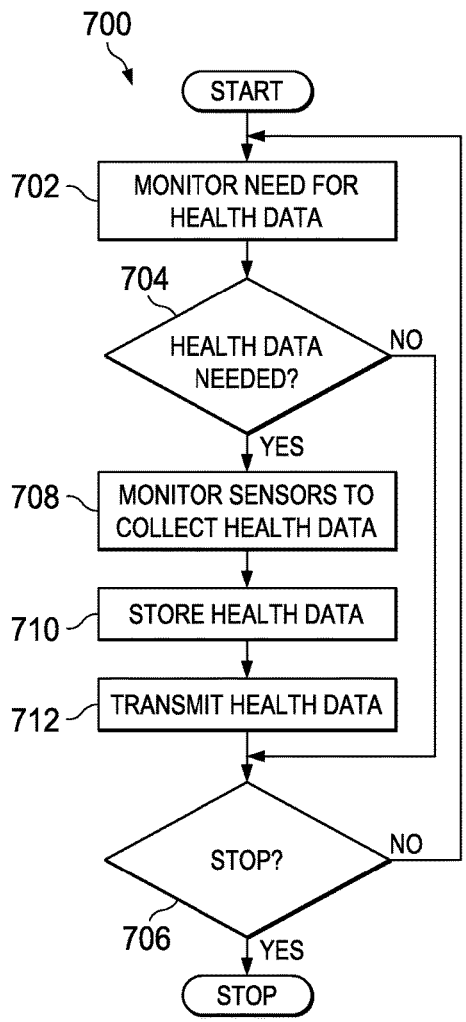
FIG. 7 is a flowchart that illustrates a method of collecting health data in accordance with one or more embodiments of the present invention.

FIG. 7 is a flowchart that illustrates a method 700 of collecting health data 200 (temperature data 200a, blood condition data 200b, blood pressure data 200c, force data 200d, body fat data 200e, body position data 200f, audio data 200g, respiration data 200h, neural data 200i and/or heart rate data 200j) in accordance with one or more embodiments of the present invention. Method 700 may be executed by the mobile device module 308 to provide for collecting health data 200 by the mobile device 122. For example, the mobile device 122 may execute a portion of the mobile device module 308 to execute a routine for collecting data upon the employee successfully logging into the employee health monitoring application.

Method 700 may include monitoring the need for health data 200, as depicted at block 702. In some embodiments, monitoring the need for health data may include determining whether or not there is a need to collect health data 200 from one or more of the sensors 120. In some embodiments, the need for health data 200 may be identified based on a request from another component of system 100. For example, the mobile device 122 may determine that there is a need to collect health data 200 in response to a request for health data (e.g., a request to initiate a health test and/or a query for the health data 200) received from the server 104 and/or the employee 401 (e.g., via a user request to start a health test).

In some embodiments, the need for health data 200 may be identified based on a corresponding health monitoring test schedule/routine. For example, where a health test schedule requires collection of health data 200 at 12:00 pm, it may be determined that health data 200 is needed if the current time is 12:00 pm. As another example, where a health test schedule requires the continuous collection of a batch of health data 200 from 8:00 am-6:00 pm, it may be determined that health data 200 is needed if the current time is in the range of 8:00 am-6:00 pm. As yet another example, where a health test schedule requires the repeated collection of health data 200 at an hourly interval from 8:00 am-6:00 pm, it may be determined that health data 200 is needed if the current time is 8:00 am, 9:00 am, and so forth. It will be appreciated that these test schedules are exemplary, and other embodiments may include any suitable test schedule.

Where it is determined that health data 200 is not needed, at block 704, method 700 may include proceeding to determining whether or not the test routine should be stopped, as depicted at block 706. In some embodiments, it may be determined that the routine should stop based on an instruction to stop from another device of system 100. For example, the mobile device 122 may determine that it should stop execution of the health monitoring test routine in response to an instruction from the server 104 and/or the employee 401 to stop the health test routine (e.g., an employee request to terminate the health test submitted via an interactive health monitoring dashboard as discussed in more detail below). Where it is determined that the execution of the health monitoring test routine should be stopped, the health test routine may be stopped.

Where it is determined that health data 200 is needed, at block 704, method 700 may include proceeding to monitoring of the sensors 120 to collect the health data 200, as depicted at block 708. In some embodiments, monitoring the sensors 120 to collect the health data 200 includes monitoring the particular sensors 120 that provide the particular health data 200 needed. For example, where the heath data 200 needed includes the employee's body temperature, monitoring the sensors 120 to collect the health data 200 may include, the mobile device 122 monitoring one or more of the temperature sensors 202 (e.g., the thermometer/thermocouple 402, the sensor pads 520, the IR sensor 524 and/or the like) to collect corresponding temperature measurements (e.g., temperature data 200a). Similar techniques may be employed for collecting other forms of health data 200 from the various sensors 120 (e.g., integrated sensors 120a and/or external sensors 120b) of the system 100. For example, the mobile device 122 may collect temperature data 200a, blood condition data 200b, blood pressure data 200c, force data 200d, body fat data 200e, body position data 200f, audio data 200g, respiration data 200h, neural data 200i and/or heart rate data 200j, from the corresponding one or more temperature sensors 202, one or more blood condition sensors 204, one or more blood pressure sensors 206, one or more force sensors 208, one or more body fat sensors 210, one or more body position sensors 212, one or more audio sensors 214, one or more respiration sensors 216, one or more neural sensors 218, and/or one or more heart rate sensors 220 of the mobile health monitoring system 102, in a similar manner.

Method 700 may include storing the health data 200, as depicted at block 710. In some embodiments, storing the health data 200 may include storing the collected health data 200 in local or remote memory. For example, the mobile device 122 may store the collected health data 200 in local memory 301. In some embodiments, storing the heath data 200 may include buffering/queuing the health data 200 for transmission at a later time.

Method 700 may include transmitting the health data 200, as depicted at block 712. In some embodiments, transmitting the health data 200 may include transmitting the health data 200 to another component/entity of system 100. For example, the mobile device 122 may transmit the health data 200 (e.g., the health data 200 stored in memory 301) to server 104 for use in monitoring the health of the employee 401. In some embodiments, the health data 200 may be transmitted from the mobile device 122 to the server 104 via network 118.

In some embodiments, the transmission of the health data 200 may be regulated based on a corresponding schedule for sending/transmitting the health data. For example, where a health test routine requires collection of health data at 12:00 pm, the health data 200 may be collected and transmitted at or about 12:00 pm. As further example, where a health test routine requires the continuous collection and transmission of health data from 8:00 am-6:00 pm, the health data 200 may be collected and transmitted from 8:00 am-6:00 pm such that a substantially continuous stream of health data 200 is transmitted (e.g., from the sensors 120 to the mobile device 122 and/or from the mobile device 122 to the server 104) for use in monitoring the employee's health. As a further example, where a health test schedule requires the continuous collection of health data from 8:00 am-6:00 pm and the transmission of the health data in batches at hourly intervals, the health data 200 may be collected and stored from 8:00 am-6:00 pm with batches of the health data 200 for each preceding hour transmitted at or about 9:00 am, 10:00 am and so forth.

In some embodiments, after transmitting the health data collected, method 700 may progress to block 706 to determine whether or not the acquisition of health data should continue. Accordingly, the mobile device 122 may collect the health data 200 from the various sensors 120 as required for use in monitoring the health of employees.

It will be appreciated that the method 700 is an exemplary embodiment of methods that may be employed in accordance with techniques described herein. The method 700 may be may be modified to facilitate variations of its implementations and uses. The method 700 may be implemented in software, hardware, or a combination thereof. Some or all of the method 700 may be implemented by one or more of the modules/applications described herein, such as mobile device module 308. The order of the method 700 may be changed, and various elements may be added, reordered, combined, omitted, modified, etc.

The server 104 (see FIG. 1) may include a network entity that serves requests by other network entities as will be understood by those skilled in the art. For example, the sever 104 may serve request by client entities, such as the mobile device 122, the employee computer 130, the employer workstation 103b, and/or the like via the network 118. The server 104 may host a content site, such as a website, a file transfer protocol (FTP) site, an Internet search website or other source of network content. In some embodiments, the server 104 may host one or more applications, such an employee health monitoring application. Some or all of the employee health monitoring application may be executed locally on the server 104 and/or remotely by various other network entities, such as the mobile device 122, the employee computer 130, the employer workstation 103b, remote workstation 112, and/or the like. For example, the server 104 may cause the execution of remote applications/processes (e.g., an application executing the method 700) on the mobile device 122 to collect the health data 200 from the employee, execute a local application (e.g., a health monitoring application) to conduct processing of the collected health data 200 for use in monitoring the employee's health and serving health content (e.g., a health report) for display on the mobile device 122, the employee computer 130, the employer workstation 103b, remote workstation 112, and/or the like.

The file server 106 may be employed by the system to manage employee health information 109 as will be understood by those skilled in the art. For example, the file server 106 may manage access to the database 108 by the other network entities, including the server 104. The file server 106 may execute a database management system, e.g. a set of software programs that controls the organization, storage, management, and retrieval of data in the database(s) 108, such as health information 109. The database 108 may include an employee information database. For example, the database 108 may store the employee health information 109 and/or an employee access information (e.g., user credential data and permissions data) that can be used to verifying user's right to access various features of the system 100 and/or the health information 109. The file server 106 and/or the database 109 may include network attached storage ("NAS"), storage area networks ("SAN"), or direct access storage ("DAS"), or any combination thereof. In some embodiments, a database server can be used to store the database(s) 108 instead of or in addition to file server 106.

The mobile device 122, the employee computer 130, the employer workstation 103b, and/or the remote workstation 112 may include personal computers (PC) as is known in the art. The computers may run UNIX, Linux, Windows®, or some other operating system compatible with the networked systems discussed herein. In some embodiments, the mobile device 122, the employee computer 130, the employer workstation 103b, and/or the remote workstation 112 may include remote terminals that enable a user to interact with various processes being controlled by the server 104. For example, the operations described herein with regard to the mobile device 122 and/or the employee computer 130 may be executed by server 104, and the mobile device 122, the employee computer 130, the employer workstation 103b, and/or the remote workstation 112 may include network terminals that provide for user interaction with the operations provided by the server 104. Moreover, the mobile device 122, the employee computer 130, the employer workstation 103b, and/or the remote workstation 112 may provide access to computer program instructions stored on the server 104. For example, a health monitoring application running on server 104 may be accessible via the mobile device 122, the employee computer 130, the employer workstation 103b, and/or the remote workstation 112 such that the employee may provide access credentials to login to their account, the server 104 may verify their credentials/permissions, and the employee may be able to enter/edit their health information 109 via employee computer 130. Health information provided via the mobile device 122, the employee computer 126, the employer workstation 103b, and/or the remote workstation 112 can be forwarded via server 104 to file server 106 for use in updating the employee's health information 109 stored in database 108. In some embodiments, the mobile device 122, the employee computer 126, the employer workstation 103b, and/or the remote workstation 112 can interface with different servers (e.g., web or network servers 104, 106 or 110) for accessing health information 109 via communications network 120.

Employer workstation 103b may provide an employer (e.g., the employee's manager, the employee's human resources manager, or the like) access to employee health information 109 for one or more employees. For example, the employer may be provided regular reports and/or alerts regarding the health of some or all of their employees, may proactively initiate review of employee health information 109 for some or all of their employees, and/or initiate health test for some or all of their employees via the employer workstations 103*b*. In some embodiments, the employer may access such features via an interactive dashboard displayed to the employer. Thus, for example, an employer may determine whether a health condition is affecting a given employee, determine whether or not an employee is following their health plan, determine whether some or all employees of a group (e.g., at a certain facility) are experiencing similar symptoms indicative of a group wide health concern (e.g., a high percentage of employees at a given facility have developed asthma, chronic obstructive pulmonary disease ("COPD"), or other chronic condition) via an interactive health dashboard.

Figure 8:
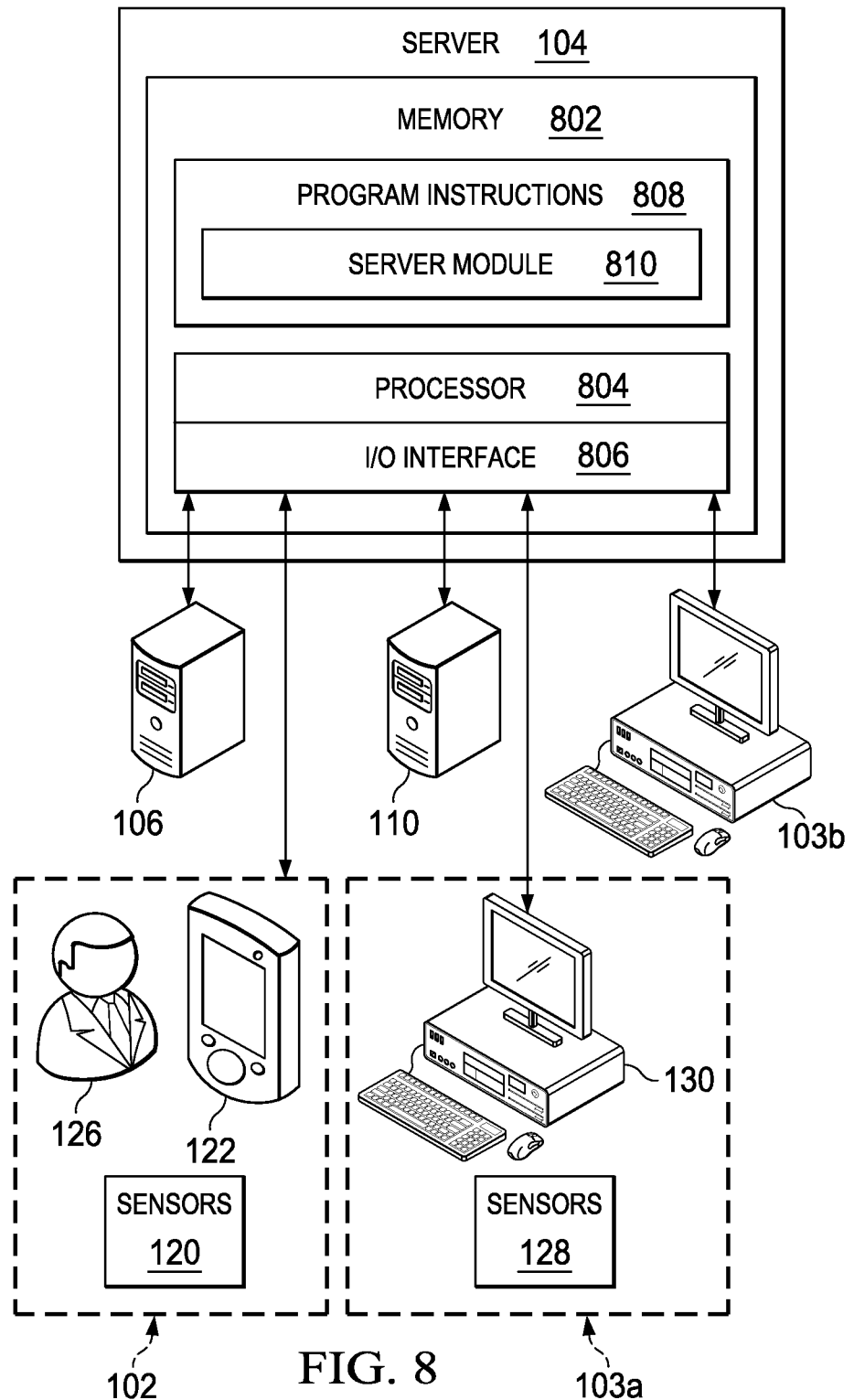
FIG. 8 is a block diagram illustrating components of a server in accordance with one or more embodiments of the present invention.

FIG. 8 is a block diagram illustrating components of the server 104 in accordance with one or more embodiments of the present invention. In some embodiments, the server 104 includes a memory 802, a processor 804 and an input/output (I/O) interface 806.

The memory 802 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 802 may include a non-transitory computer readable storage medium having program instructions 808 stored thereon that are executable by a computer processor (e.g., the processor 804) to cause the functional operations described herein with regard to the server 104. The program instructions 808 may include a server module 810 including program instructions that are executable by the processor 810 to provide some or all of the functionality described herein with regard to the server 104.

The processor 804 may be any suitable processor capable of executing/performing program instructions. The processor 804 may include a central processing unit (CPU) that carries out program instructions (e.g., of the server module 810) to perform arithmetical, logical, input/output and other operations of the server 104. The processor 804 can be any commercially available processor, or plurality of processors, adapted for use in the computer server 104, such as Intel® Xeon® multicore processors manufactured by Intel Corporation, Intel® micro-architecture Nehalem manufactured by Intel Corporation, AMD Opteron™ multicore processors manufactured by AMD Corporation, or the like. As one skilled in the art will appreciate, the processor 804 may also include components that allow the computer server 104 to be connected to peripherals (e.g., a display and keyboard that would allow direct access to the processor and the memory 802, and/or application executing via the server 104).

The I/O interface 806 may provide an interface for connection of one or more I/O devices to server 104. The I/O devices may include other network devices, such as the file server 106, the web server 110, the mobile device 122, the employee computer 130, the employer workstation 103*b*, the sensors 120, and/or the like. The I/O devices may be communicatively coupled to the I/O interface 806 via a wired or wireless connection.

Figure 9:
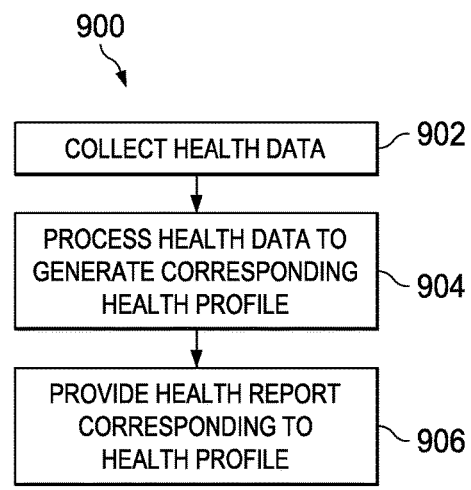
FIG. 9 is a flowchart that illustrates a method of monitoring the employee's health in accordance with one or more embodiments of the present invention.

In some embodiments, the server 104 uses the health data 200 collected by the sensors 120 to monitor the employee's health. FIG. 9 is a flowchart that illustrates a method 900 of monitoring the employee's health in accordance with one or more embodiments of the present invention.

Method 900 may include collecting health data 200, as depicted at block 902. In some embodiments, collecting health data may include collecting health data 200 from other entities of system 100. For example, the server 104 may collect health data 200 (e.g., temperature data 200*a*, blood condition data 200*b*, blood pressure data 200*c*, force data 200*d*, body fat data 200*e*, body position data 200*f*, audio data 200*g*, respiration data 200*h*, neural data 200*i* and/or heart rate data 200*j*) for the employee via the various sensors 120 of the mobile health monitoring system 102 (See FIG. 10 including a block diagram illustrating dataflow within the system 100 in accordance with one or more embodiments of the present invention). In some embodiments, the server 104 may also collect some or all of the health data for the employee via other sources, such as the sensors 128 of the employee workstation 103*a*.

In some embodiments, monitoring the health sensors to collect the health data 200 includes executing a single measurement by some or all of the sensors 120 of the mobile health monitoring system 102. For example, some or all of the sensors 120 of the mobile health monitoring system 102 may be employed to record a single measurement in sequence (e.g., one after the other) or in parallel (e.g., at the same time) and transmit corresponding health data 200 to the mobile device 122. As described herein, the mobile device 122 may collect the measurements from each of the sensors 120 of the mobile health monitoring system 102 and transmit corresponding health data 200 to the server 104 for use in monitoring the employee's health.

In some embodiments, monitoring the health sensors to collect the health data 200 includes executing multiple measurements by some or all of the sensors 120. For example, some or all of the sensors 120 of the mobile health monitoring system 102 may be employed to record a set of measurements (e.g., one per minute) over a given period of time (e.g., 5 minutes, 1 hour, 8 hours, or the like) and transmit corresponding health data 200 to the mobile device 122. As described herein, the mobile device 122 may collect the measurements from each of the sensors 120 of the mobile health monitoring system 102 and transmit corresponding health data 200 to server 104 for use in monitoring the employee's health.

In some embodiments, the health data 200 is collected via health test that are initiated by the server 104. For example, the server 104 may execute a health monitoring routine that requires the health data 200 to be collected according to a given test schedule/routine (e.g., health data to be sensed/collected from 8 am-6 pm, health data to be sensed/collected hourly from 8 am to 6 pm, and/or the like), the server 104 may determine health data 200 is required based on the schedule, and, in response to determining that health data 200 is required, the server 104 may query the mobile device 122 and/or the sensors 120 for health data 200 according to the schedule. For example, where a test schedule/routine requires collection of health data from 8 am to 6 pm, the server 104 may send, to the mobile device 122 at 8 am, a first request to initiate collection and forwarding of health data 200 to the server 104, and send, to the mobile device 122 at 6 pm, a second request to terminate collection and forwarding of the health data 200 to server 104. In such an embodiment, the mobile device 122 may continually acquire and forward health data 200 to server 104, from 8 am to 6 pm. The server 104 may transmit similar requests in accordance with any suitable test schedule/routine. For example, where a test schedule/routine requires collection of health data hourly from 8 am to 6 pm, the server 104 may send, to the mobile device 122 at each of 8 am, 9 am, 10 am, and so forth, a request to collect and forward health data 200 to server 104. In such an embodiment, the mobile device 122 may collect and forward a set of health data 200 to server 104 each hour from 8 am to 6 pm (e.g. at 8 am, 9 am, 10 am, and so forth).

In some embodiments, the server 104 initiates a health test based on an external request/event, such as a request generated by a user. For example, where an employee or an employer is interacting with an interactive health dashboard for a given employee (as discussed in more detail below) and the user requests to run a health test, the server 104 may determine that health data is required based on the request, and, in response to determining that health data is required, the server 104 may query the mobile device 122 for the health data. In such an embodiment, the mobile device 122 may collect and forward a set of health data 200 to server 104 at or near the time of the user's request to conduct a health test. Thus, the server 104 may initiate health test automatically (e.g., based on a test schedule/routine) and/or in response to external request (e.g., a user initiated request from an employee, an employer, or other user).

In some embodiments, the health data 200 for one or more employees may be logged over time. For example, health data 200 may be collected for each employee of a group of employees, and the health information 109 for each of the employees may be updated to reflect the health data collected. Thus, a log of health data for each of the employees may be generated. In some embodiment, the log of health data for a given employee may be used to generate a profile for the employee. For example, the logged health data 200 may be used to generate health profiles and/or reports that are based on current/recent health data 200 (e.g., health data 200 collected within a minute, hour, day, week, month, or the like) and/or historical health data 200 (e.g., health data 200 collected more than a minute, hour, day, week, moth, year, or the like prior). In some embodiments, the health information 109 for the employee includes a record/log of the employee's health information. For example, the employee health information 109 may include, for each employee, employee personal profile data (e.g., name, age, etc.), historical/current employee health profile data (e.g., health data, characteristics, conditions, plans) and/or employee activity data (e.g., a log of exercises, food consumed, etc.), and so forth.

Method 900 may include processing the collected health data to generate one or more corresponding health profiles 1000 (See FIG. 10), as depicted at block 904. In some embodiments, the health profile 1000 is generated by the server 104 based on the processing of the collected health data 200. The health profile 1000 may include health characteristics 1002, health conditions 1004, health risks 1006, and/or health plans 1008 for the employee.

In some embodiments, the health characteristics 1002 may include a first level of health profile data that is derived from the collected health data 200. For example, server 104 may process the collected health data 200 (e.g., biometric health data and/or biometric health data) to identify various biometric health characteristics 1002a and/or biomechanic health characteristics 1002b for the employee. Biometric health characteristics 1002a may include, for example, the employee's sensed body temperature 1010, body weight 1011, body fat 1012, heart rate 1013, blood pressure 1014, blood condition (e.g., blood oxygenation, blood glucose level, etc.) 1015, respiration rate 1016, neural/brain activity 1017, and/or the like. Biomechanic health characteristics 1002b may include, for example, the employee's sensed body position 1020 (e.g., the employee's physical positioning and/or movement of the employee's head, torso, arms, hands, legs, feet, and/or the like), eye movement (e.g., focal point, blink rate, pupil dilation of the eye, and/or the like) 1021, neural/brain activity 1017, physical exertion 1022, and/or the like.

In some embodiments, the health characteristics 1002 may be provided directly via the health data 200. For example, the heart rate data 200i may include a determined value for heart rate (e.g., 80 beats per minute ("BPM"). A similar value may be provided for some or all of the other health characteristics 1002. In some embodiments, the health characteristics 1002 may be extrapolated/calculated from the health data 200. For example, the health data 200 may include a set of measurement indicative of heart beats over a period of time (e.g., a log of blood pressure data 200c indicative of twenty heart beats over fifteen seconds) and the server 104 may process the set of measurement to determine the corresponding hear rate value (e.g., a heart rate of 80 BPM). A similar determination may be made for some or all of the other health characteristics 1002. For example, the health data 200 may be received and/or processed in a similar manner to determine values for some or all the other health characteristics 1002 (e.g., based on received values, data sets, and/or the like).

In some embodiments, the body weight 1011 is based on the force data 200d collected via one or more of the force sensors 208. For example, the force data 200d indicative of the forces sensed by the force transducers 414 may be used to determine the employee's weight. For example, where the right and left force transducers 414 each sense a force of about 23 kg (62 lbs.) the forces may be added together to determine a body weight for the employee of about 56.5 kg (124.6 lbs.).

In some embodiments, the body fat 1012 is based on body fat data 200e collected via one or more of the body fat sensors 210. For example, the body fat 1012 may be determined using bioelectrical impedance analysis (BIA) of the impedance/resistance sensed by the body fat sensor 210. Ideally, male employees will have a body fat measurement of about 8-17% and female employees will have a measurement between about 10-21%. The body fat 1012 may include a body fat percentage which is determined as the total weight of the person's fat divided by the person's weight.

In some embodiments, the heart rate 1013 is based on heart rate data 200j collected via one or more of the heart rate sensors 220. For example, the heart rate 1013 may be determined using the number of heart beats sensed over a given period of time, typically sixty seconds. In some embodiments, the heart rate 1013 is based on blood pressure data 200c collected via one or more of the blood pressure sensors 206. For example, the heart rate 1013 may be determined using the rate of pulsations of blood pressure which may correspond to the heart rate.

In some embodiments, the blood pressure 1014 is based on blood pressure data 200c collected via one or more of the blood pressure sensors 206. The blood pressure 1014 may be determined from the blood pressure data 200c which is indicative of pressure pulsations due to blood flow. For example, the blood pressure 1014 may be determined based on a maximum blood pressure detected (e.g., the "systolic" blood pressure) and the minimum blood pressure detected (e.g., the "diastolic" blood pressure) via a blood pressure cuff. The blood pressure 1014 may be recorded as the systolic blood pressure over the diastolic blood pressure (e.g., 90/60 mmHg).

In some embodiments, the blood condition 1015 is based on blood condition data 200b collected via one or more of the blood condition sensors 204. For example, the blood oxygenation, blood glucose level, and/or the like may be determined from blood condition data 200b provided by a pulse oximeter or similar blood conditions sensor.

In some embodiments, the respiratory rate 1016 is based on respiration data 200h collected via one or more of the respiration sensors 216. For example, the respiration rate may be determined based on a number of employee breaths sensed by the respiration sensor 216 over a given period of time. For example, where the respiration data 200h indicates that the employee has taken four breaths in fifteen seconds, the employees respiration rate 1016 may be determined as sixteen breaths per minute ($V_f$).

In some embodiments, the brain activity 1017 is based on neural data 200i collected via one or more of the neural sensors 218. In some embodiments, the brain activity 1017 includes a log of neuro-signals (e.g., including alpha, beta, gamma, and delta waves) that are indicative of the employee's brain state, including the employee's emotional state, thoughts (e.g., cognitive thoughts, subconscious thoughts, and intent), facial movements (e.g., facial expressions), motor functions and/or the like. The brain activity 1017 may include or otherwise be extrapolated from the neural data 200i. The brain activity 1017 may be both of biometric and biomechanic characteristics based at least on its use in determining various biometric and biomechanic health profile data (e.g., various biometric and biomechanic conditions and identified/predicted health issues/risks).

In some embodiments, the body position 1020 is based on body position data 200f collected via one or more of the body position sensors 212. For example, the body position data 200f collected from the camera 512 and/or the positioning devices may be used to determine the relative and/or absolute position of the employee's head, torso, arms, elbows, hands, legs, knees, feet, waist and/or the like. In some embodiments, the employee's body position 1020 is determined using the body position data 200f. In some embodiments, the employee's body position is determined based on the forces sensed by various ones of the force sensors 208. For example, it may be determined that the employee is standing when a force approximately equal to the employee's body weight is sensed by the force transducers 414.

In some embodiments, the physical exertion 1022 is based on the force data 200d collected via one or more of the force sensors 208. For example, the force data 200d indicative of the forces sensed by the force transducers 414 integrated into the employee's gloves and/or boots may be used to determine a physical exertion by the employee to lift/move an object.

In some embodiments, one or more of the health characteristics 1002 may be used to determine one or more of the health conditions 1004. The health conditions 1004 may include a second level of health profile data that is derived from the one or more of the health characteristics 1002 and/or the collected health data 200. For example, the server 104 may process the health characteristics 1002 and/or the collected health data 200 to extrapolate various biometric health conditions 1004a and/or biomechanic health conditions 1004b for the employee. Biometric health conditions 1004a may include, for example, a body mass index ("BMI") 1030, a body composition 1031, a fitness level 1032, a resting heart rate ("RHR") 1033, a maximum heart rate ("MHR") 1034, a target heart rate ("THR") 1035, emotions 1036, thoughts 1037, and/or the like for the employee. Biomechanic health conditions 1004b may include, for example, posture ("posture analysis") 1040, muscle tension 1041, a stress level 1042, a physical injury 1043, an eye fatigue level 1044, facial movements 1045, motor functions (e.g., gestures) 1046, and/or the like for the employee.

In some embodiments a health condition 1004 may be determined based on one or more health characteristics 1002 and/or other data (e.g., the employee's personal profile). For example, BMI 1030 and/or body composition 1031 may be extrapolated from body weight 1011 and body fat 1012. Fitness level 1032 may be based on weight 1011, heart rate 1013, and/or blood pressure 1014. Resting heart rate 1033, maximum heart rate 1034, and/or target heart rate 1035 may be based on the heart rate 1013 and/or the employee's age. Emotions 1036 and/or thoughts 1037 may be based on the employee's brain activity 1017. Posture 1040 and muscle tension 1041 may be based on the observed body position 1020 of the employee (e.g., physical positioning and movement of the head, torso, arms, hands, legs, feet, and/or the like) and/or the physical exertion 1022. Stress level 1041 may be based on the observed body position 1020, eye movement 1021 and/or brain activity 1017 for the employee. Physical injury 1043 may be based on the observed body position 1020, eye movement 1021, brain activity 1017 and/or physical exertion 1022 for the employee. Eye fatigue 1044 may be based on the observed eye movement 1021 of the employee. Facial movements 1045 and/or motor functions 1046 may be determined based on the brain activity 1017.

The BMI 1030 may be the individual's body mass (m) divided by the square of their height (h). In some embodiments, BMI 1030 is determined using the following equation:

$$\text{BMI} = m \cdot 703/h^2 \quad (1)$$

Where "m" is the employee's mass (in kg. or lbs.) and "h" is the employee's height (in meters or inches). From this equation, the server 104 can determine whether the employee is of average weight (e.g., having a BMI in the range of about 18.5-25), overweight (e.g., having a BMI in the range of about 25-30), or obese (e.g., having a BMI over about 30).

The body composition 1031 may indicate a percentage of bone, fat and/or muscle in the employee's body. In some embodiments, the body composition is determined based at least on the body fat percentage and the body weight 1011.

In some embodiments, the fitness level 1032 is indicative of the employee's body's ability to withstand a physical workload and/or recover in a timely manner. The fitness level 1032 may be based on the employee's heart rate. For example, an employee may be determined to have a good fitness level if their resting heart rate 1034 is under about 100 BPM.

In some embodiments, the respiratory rate 1016 is indicative of the number of breaths taken within a set amount of time (e.g., 60 seconds). In some embodiments, the resting heart rate (RHR) 1033 is the measured heart rate (HR) 1013 taken at a period of low activity by the employee (e.g., while seated in the chair 404 and not engaging in any strenuous work activities). The maximum heart rate (MHR) 1034 may be determined using the following equation:

$$\text{MHR} = 205.8 - (0.685 \times \text{age}) \quad (2)$$

Where "age" is the age of the employee in years. The target heart rate (THR) 1035 may be calculated using the following formula, the "Karvonen method":

$$THR=((MHR \times RHR) \times \% \text{ intensity})+RHR \quad (3)$$

Where intensity is a percentage, typically about 65%-85%. The target heart rate 1035, resting heart rate 1033 and maximum heart rate 1034 may be provided to the employee to aid the employee in safe exercise regimens, the formulation of a health plan, and the determination of whether the employee has met its health plan goals for the day, e.g., whether the employee has reached their target heart rate 1035 by the distance and length of time the employee has indicated to the program it has exercised. Also, if the employee's resting heart rate 1033 is above 100 beats per minute, for example, the system may provide the employee with an alert/warning regarding the risks for cardiovascular disease, stroke, or obesity via the health dashboard 1012, the health report 1010 and/or the like.

In some embodiments, the employee's emotions 1036, thoughts 1037, facial movements 1045 and/or motor functions 1046 may be based on the sensed neuro signals (e.g., brain activity 1017). For example, a plurality of predetermined brain wave patterns may be associated with corresponding emotions, thoughts, facial movements and/or motor functions. During processing of the brain activity 1017, the sensed/observed neuro signals may be compared to the plurality of predetermined neural signal patterns to identify a match there between. Upon matching the observed neuro signals to one or more of the predetermined neural signal patterns, it may be determined that the employee is engaged in emotions (e.g., happy, sad, excited, depressed, etc.) 1036, thoughts (e.g., intent to take an action, etc.) 1037, facial movements (e.g., facial gestures such as smiling) 1045 and/or motor functions (e.g., a sequence of movements) 1046 that correspond to the matching predetermined neural signal pattern. In some embodiments, as described herein, an animated avatar may be used to mimic the employee's current emotional state and/or facial gesture. For example, when it is determined that the employee is happy and/or smiling, a displayed avatar can be animated to smile, providing the employee or other persons reviewing the employee's health (e.g., the employer) with an indication of the employee's current emotional state and/or facial expression. In some embodiments, the ability to determine the employee's thoughts may be employed to assist the employee with completing their work duties. For example, where the system 100 is able to determine that the employee intends to open a word processing application on the mobile device 122, the system 100 may launch the word processing application on the mobile device 122 based on the determined intent to act, without any physical interaction by the employee.

In some embodiments, a determination of the employee's posture (e.g., be proper ergonomic position) 1040 may be based on body position 1020. For example, the employee may be determined to have good posture that where one or more of the employee's hands, wrists, and forearms are straight, in-line and roughly parallel to the floor; the employee's head is level, or bent slightly forward, forward facing, and balanced, and generally in-line with the torso; the employee's shoulders are relaxed and its upper arms hang normally at the side of the body; the employee's elbows stay in close to the body and are bent at angles between about 90 and 120 degrees; the employee's feet are fully supported by the floor or a footrest (if the employee's desk height is not adjustable); the employee's back is fully supported when sitting vertical or leaning back slightly; the employee's thighs and hips are generally parallel to the floor; and/or the employee's knees are about the same height as the hips with the feet slightly forward. The posture 1040 may include a determination of the proper alignment of the head, torso, arms, and feet when the employee is standing/sitting and the employee's deviation from the proper alignment based on the observed body position 1020. In some embodiments, the actual body position of the employee, relative to the ideal body position may be determined and the posture 1040 may indicate, a percentage deviation of the actual body position to the ideal body position and/or may include suggestions for improving the employee's posture (e.g., sit up in chair with lower back firmly contacting chair lumbar support, straighten your back while standing, etc.).

In some embodiments, level of muscle tension 1041 may be determined based on the employee's body position 1020, including, for example the employee's arm position and shoulder height (e.g., whether the employee's shoulders are raised and the arm is bent in a sub-optimum way), the employee's respiratory rate 1016, and, if multiple health tests have been taken, the length of time the employee' has engaged in physical exertion 1022. For example, it may be determined that the employee is experiencing a high level of muscle tension where the employee's arm is repetitively extended to lift objects. Using these measurements, the system can determine an estimate of the employee's muscle tension 1041 using known techniques.

In some embodiments, a level of eye fatigue 1044 may be determined based on the employee's eye movement 1021. For example, it may be determined that the employee is experiencing a higher level of eye fatigue 1044 where their blink rate has slowed to less than fifteen blinks per minute and/or the employee has been staring at substantially the same position (e.g., the display screen of the mobile device 122) for an extended period (e.g., over twenty minutes).

Although the illustrated embodiment includes exemplary sets of health characteristics 1002 and corresponding health conditions 1004 extrapolated therefrom, it will be appreciated that embodiments may include one or more of the listed health conditions 1004 being provided as health characteristics 1002 or vice versa. For example, where a sensor 120 provides a resting heart rate value, the resting heart rate may be provided as a health characteristic 1002 as opposed to a health condition 1004 extrapolated from the health characteristics 1002. Although the illustrated embodiment includes an exemplary listing of health characteristics/conditions, it will be appreciated that other embodiments may include assessing any variety of health characteristics/conditions that may be of interest to the employee, the employer and/or other users.

The biometric and/or biomechanic health characteristics 1002 and/or health conditions 1004 may be used to identify/predict corresponding health risks 1006. The health risks 1006 may include a third level of health profile data that is derived from one or more of the health conditions 1004, the health characteristics 1002 and/or the collected health data 200. For example, the server 104 may process the health conditions 1004, the health characteristics 1002 and/or the collected health data 200 using predictive analysis to extrapolate various biometric health risks 1006a and/or biomechanic health risks 1006b for the employee (i.e., risks for developing the associated health condition). Risk 1306 may include a prediction of a health condition that may occur. For example, where the recent health data for an employee indicates a trend of increasing body weight for an employee, it may be predicted that the employee will become obese within a given time period, and is, thus, at risk for obesity. Biometric health risks 1006a may include, for example, risk of obesity 1050, risk of injury 1051, risk of diabetes 1052, risk of infection 1053, risk of inflammation 1054, risk of circulation problems 1055, risk of cardiovascular disease 1056, risk of a cardiovascular accidents (e.g., stroke) 1057, risk of illness (e.g., the flu) 1058, risk of developing asthma 1059, risk of developing allergies 1060, risk of developing bronchitis 1061, risk of experiencing depression 1062, and/or the like. Biomechanic health risks 1006b may include, for example, risk of back injury 1063 (e.g., upper/lower back pain), risk of neck injury 1064, risk of musculoskeletal syndrome ("MSD") 1065, risk of carpal tunnel syndrome ("CTS") 1066, risk of epicondylitis (i.e., tennis/golfer's elbow) 1067, risk of a rotator cuff injury 1068, risk of eye disease 1069, risk of physical fatigue, and/or the like. The prediction of health issues and the identification of associated health risks may provide a proactive environment for predicting and responding to health risks before they escalate into actual health conditions.

In some embodiments a health risk may be determined based on one or more heath conditions 1004, health characteristics 1002 and/or other data (e.g., the employee's personal profile). For example, risks of obesity 1050, injury 1051, diabetes 1052, and cardiovascular disease may be based on BMI 1030 and/or body comp 1031. Risk of infection 1053, inflammation 1054, and circulation problems 1055 may be based on body temperature 1010. Risk for cardio vascular disease 1056, cardiovascular accidents 1057, and obesity 1050 may be based on fitness level 1032, blood pressure 1014, and heart rate 1013. Risk for illness 1058, asthma 1059, allergies 1060 and bronchitis 1051 may be based on respiratory rate 1016. Risk of depression 1062 may be based on the employee's emotions 1036 and thoughts 1037. Risk of risk of back injury 1063, neck injury 1064, musculoskeletal syndrome (MSD) 1065, carpal tunnel syndrome (CTS) 1066, epicondylitis 1067, rotator cuff injury 1068, and/or physical fatigue 1070 may be based on the employee's body position 1020, physical exertion 1022, posture 1040, muscle tension 1041, injury 1043, motor functions 1046, and/or the like.

In some embodiments, an employee that is obese (e.g., having a BMI over about 30) may be determined to have a high risk of diabetes 1052 (e.g., 7.37 time greater than normal), a high risk of cardiovascular disease 1056 (e.g., 2.5 time greater than normal), a high risk of cardiovascular disease 1056 (e.g., 2.5 time greater than normal), a high risk of circulation problems 1055 (e.g., 6.38 times greater than normal risk for high blood pressure), a high risk of asthma 1059 (e.g., 2.72 time greater than normal), a high risk of asthma 1059 (e.g., 2.72 time greater than normal) and other conditions, such as 1.88 times greater than normal risk for high cholesterol, 4.41 times greater than normal risk for arthritis, and so forth.

In some embodiments, it may be determined that the employee is at risk of having or already has the flu or other illness if the employee has one or more of a body temperature 1010 over 38° C. (101° F.), a respiratory rate 1033 greater than 20 respirations per minute, and a heart rate 1013 greater than 100 BPM.

In some embodiments, it may be determined that the employee is at risk for inflammation where, for example, the employee's blood pressure 1014 is elevated, the employee's heart rate 1013 is irregular and/or the body temperature 1010 is elevated above normal (e.g., above 37° C. (98.6° F.)).

In some embodiments, it may be determined that the employee is at risk for circulation problems where, for example, the employee has a low body temperature 1010 (e.g., less than 96 degrees Fahrenheit measured at the extremities) or a high respiratory rate 1033) (e.g., greater than 20 respirations per minute).

In some embodiments, it may be determined that an employee is at risk for depression where, for example, the employee's emotions 1036 and/or thoughts 1037 demonstrate a negative pattern. For example, the employee may be determined to be at risk for depression where they have been determined to have an emotion of "unhappy" for greater than 50% of an observed period of at least one week.

In some embodiments, it may be determined that an employee is at risk for physical fatigue where, for example, the employee's motor functions 1046 are below their normal level. For example, the employee may be determined to be at risk for physical fatigue where their motor function 1046 is less than 75% of its normal level for greater than one hour.

In some embodiments, it may be determined that the employee is at risk of a back injury, neck injury, rotator cuff injury, and/or physical fatigue may be based on the employee's high level of physical exertion (e.g., lifting above a predetermined threshold of 25 kg (55 lbs.)) using poor posture/body position (e.g., bending at the back as opposed to the knees).

In some embodiments, some or all of the health characteristics 1002, health conditions 1004, and/or health risks 1006 may be determined/identified using known techniques for extrapolating data. Although the illustrated embodiment includes an exemplary listing of health risks, it will be appreciated that other embodiments may include assessing any variety of health risks that may be of interest to the employee, the employer and/or other users.

In some embodiments, one or more health plans 1008 may be generated based on the health data 200, the health characteristics 1002, the health conditions 1004 and/or the health risks 1006. Accordingly, the health plans 1008 may be based on biometric and/or biomechanic health information collected for the employee. A health plan 1008 may provide a listing of health goals (e.g., lose ten pounds, reduce calorie intake to two-thousand calories per day, etc.), suggested actions for the employee to take to reach the health goals (e.g., an exercise plan, a diet regime, suggestions such as taking breaks from using the computer, breaks from physical activity, etc.) and/or the like. In some embodiments, the health plans 1008 include a preventative health plan to help maintain and improve the employee's health over time. In some embodiments, the health plans 1008 include an interactive health plan that can be modified by the employee and/or the employer, and/or that can be used to track the employee's progress relative to the plan goals, and/or the like.

In some embodiments, the health plans 1008 may be determined using a discrete health test, or formulated from a plurality of health tests (e.g., current and historical health information and/or health profile data) to determine the plan based upon a health test trend (e.g., the employee's blood pressure is rising, the employee has gained weight, the employee's BMI is higher, the employee is underweight, the employee's resting heart rate is low or high based upon activity level, etc.). In some embodiments, the health plan is generated by calculating the employee's ideal health characteristics/conditions based on the current health characteristics/conditions/risks. In some embodiments, the difference between the current and ideal health characteristics/conditions/risks is used to identify or generate a corresponding health plan 1008.

Figure 11:
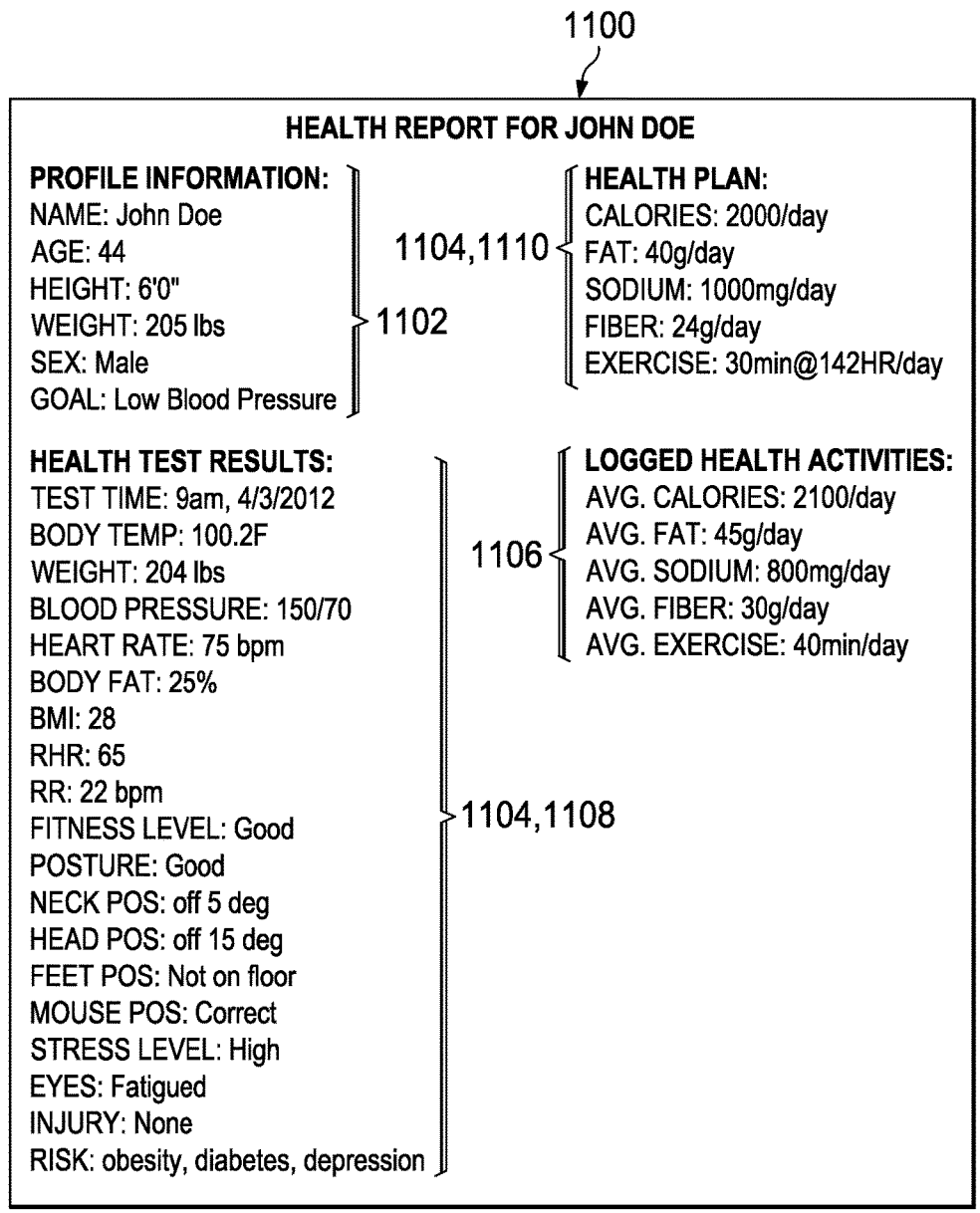
FIG. 11 illustrates an exemplary health report in accordance with one or more embodiments of the present invention.

FIG. 11 illustrates an exemplary health report 1100 in accordance with one or more embodiments of the present invention. Such a health report 1100 may be generated based on health profile 1000 and/or other health information, such as personal profile data for the employee. For example, in the illustrated embodiment, the health report 1100 includes personal profile information 1102 and health profile information 1104 and logged health activities 1106. The health profile information 1104 including health test result data 1108 (e.g., corresponding to health characteristics 1002, health conditions 1004, and health risk 1006 of the health profile 1000) and health plan data 1110 (e.g., corresponding to the health plan 1008 of the health profile 1000). The logged health activities 1106 may correspond to activity entries by the employee, as discussed in more detail below.

Method 900 may include providing a health report corresponding to the health profile, as depicted at block 906. Providing a health report corresponding to the health profile may include providing some or all of the employee's health information (e.g., personal information and/or health profile information 1000) for display to the employee, the employer, a medical practitioner, an emergency responder, and/or the like. In some embodiments, the health profile data is provided via a health report document. For example, the server 104 may serve to the mobile device 122, the employee computer 130 and/or the employer workstation 103b for display to the user, a heath report document that is the same or similar to that of the health report 1100 of FIG. 10.

In some embodiments, the health profile 1000 may be communicated via an interactive interface. For example, the server 104 may serve, to the mobile device 122, the employee computer 130 and/or the employer workstation 103b, an interactive health dashboard 1012 for communicating/displaying some or all of the health profile 1000 to the employee (e.g., via the mobile device 122 and/or employee computer 130) and/or the employer (e.g., via the employer's workstation 103b). In some embodiments, the interactive health dashboard 1012 may enable a user (e.g., the employee or employer) to selectively view/edit health information 109 for the employee (e.g., including the personal profile, the health profile, activity data, and/or the like for the employee). For example, an employee may login to the health dashboard 1012 via an application (e.g., a web browser or other network access application) of the mobile device 122 and/or the computer 130, and interact with the dashboard 1012 to update their personal profile data (e.g., name, age, etc.), review their health profile, edit their health plan, enter health activity information (e.g., food they have eaten, exercises they have competed, etc.), initiate health test and so forth.

Providing the health reports (including health characteristics 1002 and conditions 1004) may help to "inform" the employee regarding their health status. Providing the health reports (including health risks 1006) may help to "protect" the employee by alerting them to health issues that may need to be addressed. Providing the health report (including the health plans 1008) may help to "reinforce" the employee by providing a course of action that suggests actions that the employee should take to reduce their risk of developing health problems.

In some embodiments, health information is provided for review via an employee health monitoring application. Such an application may provide an interface for presenting health information to a user (e.g., the employee and/or employer) and/or enable the user to interact with the employee health information. For example, the user may be able to update personal profile data (e.g., name, age, etc.) for the employee, review the health profile data for the employee, edit the health plan for the employee, enter health activity information (e.g., food the employee has eaten, exercises completed by the employee, etc.), initiate health tests and so forth via the health monitoring application.

In some embodiments, login to the employee health monitoring application is based on user login credentials, such as a login ID, password and/or other unique identifier, such as a fingerprint or handprint. For example, to login to the employee health monitoring application and access the interactive health dashboard 1012 the user may have to provide a login ID, their password and/or provide their finger or hand print. Such an embodiment may provide secured access to the employee health information and/or restrict user's access to features of the interactive health dashboard 1012, such as initiating health tests. In some embodiments, the finger print or hand print is provided via the mobile device 122. For example, upon selecting to launch the employee health monitoring application the user may be prompted for their user ID, password, and a finger/hand print to confirm their identify. The user may supply their user ID and password via a text field and may supply their finger/hand print by placing their hand on the sensor screen 504 of the mobile device 122. The sensor screen 504 may acquire the biometric user data, including the finger/hand print. Upon the user ID, password and finger/hand print being verified (e.g., by user device 122 and/or server 104), the employee health monitoring application may be launched. For example, upon the user successfully logging in to the employee health monitoring application, an interactive health dashboard 1012 may be displayed, and/or a health status widget may be displayed on a home screen of the mobile device 122 (as discussed in more detail below). In some embodiments, an interactive health dashboard 1012 may enable the employer to selectively view health information (e.g., including the personal profile, the health profile, activity data, and/or the like) for some or all of their employees.

Figure 12:
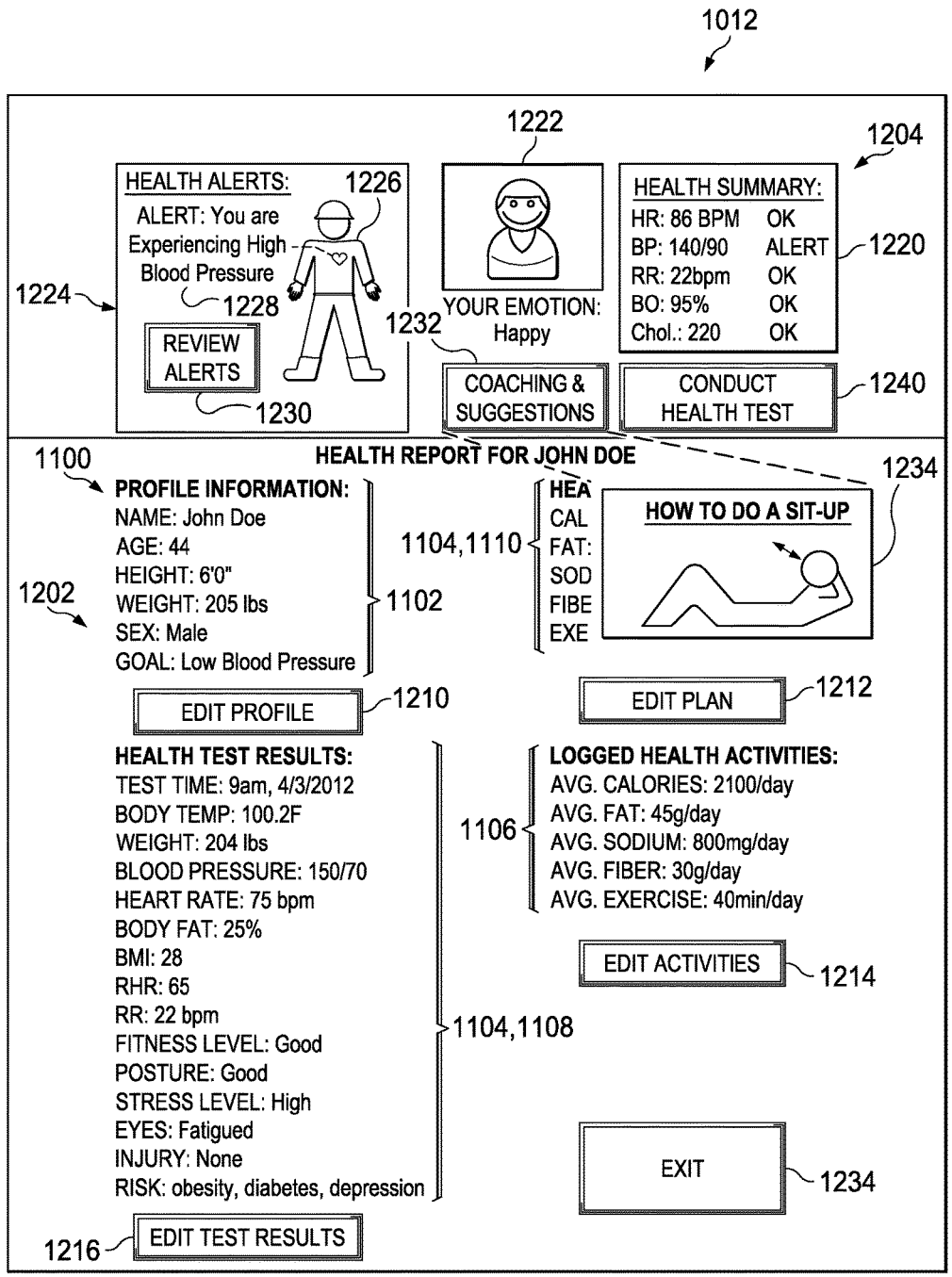
FIG. 12 is a screen-shot of an exemplary interactive health dashboard in accordance with one or more embodiments of the present invention.

FIG. 12 is a screen-shot of an exemplary interactive health dashboard 1012 of an employee health monitoring application in accordance with one or more embodiments of the present invention. In some embodiments, the interactive health dashboard ("dashboard") 1020 is served by the server 104 to a client device for display to the user. For example, the content of the dashboard 1012 may be served to the mobile device 122 for display to the employee via a graphical display (e.g., the display screen 504) of the mobile device 122, served to the employee computer 130 for display to the employee via a graphical display (e.g., monitor) of the employee computer 130, and/or served to the employer workstation 103b for display to the employer via a graphical display (e.g., monitor) of the employer workstation 103b.

In some embodiments, the dashboard 1012 includes some or all of the health information for the employee. For example, the dashboard may include a first display portion including an interactive health report 1202 and/or a second display portion including a health status widget 1204.

Figure 10:
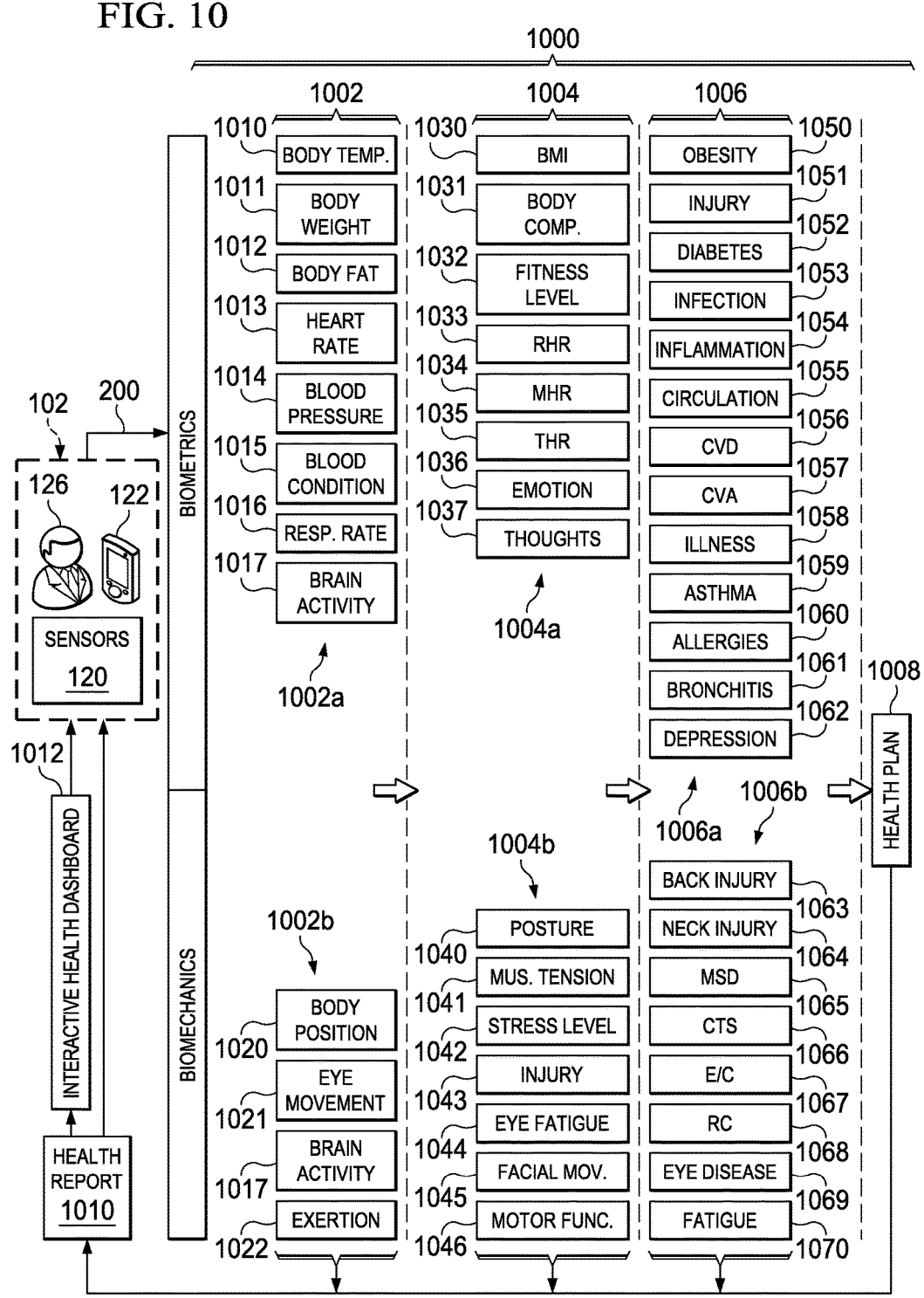
FIG. 10 is a block diagram that illustrates dataflow within the system in accordance with one or more embodiments of the present invention.

The interactive health report 1202 may include health information that is the same or similar to the health information contained in the heath report 1010 and 1100 (See FIGS. 10 and 11). For example, the interactive health report 1202 may include personal profile information 1102, health profile information 1104 and logged health activities 1106 for the employee. The health profile information 1104 may include health test result data 1108 (e.g., corresponding to health characteristics 1002, health conditions 1004, and health risks 1006 of the health profile 1000) and health plan data 1110 (e.g., corresponding to the health plan 1008 of the health profile 1000). Alerting the employee to predicted health issues and/or associated health risks may enable the employee to proactively respond to predicted health issues and/or associated health risks before they escalate into actual health conditions. The logged health activities 1106 corresponding to activity entries by the employee, as discussed in more detail below.

In some embodiments, the user can interact with the displayed health report 1100. For example, the user may be able to edit the personal profile information 1102, the health profile information 1104 and/or the logged health activities 1106 for the employee via selection of the corresponding "EDIT" button. For example, upon selecting the "EDIT PROFILE" button 1210 the user may be provided the opportunity to edit the personal profile data for the employee. Upon selecting the "EDIT PLAN" button 1212 the user may be provided the opportunity to edit the health plan for the employee. Upon selecting the "EDIT ACTIVITIES" button 1214 the user may be provided the opportunity to edit the activities for the employee. For example, an interface may be provided to enable the user to record activities that have taken part in (e.g., enter exercises that have participated in) and/or nutrition information including food they have consumed (e.g., enter a record of meals they have consumed). Upon selecting the "EDIT TEST RESULTS" button 1216 the user may be provided the opportunity to edit the test results the employee. For example, where the test results (e.g., the health data, the characteristics, conditions, risks and/or the like) appear to be incorrect, the user may be able to manually edit the test results.

In some embodiments, the health status widget 1204 includes a summary of the employee's health status. For example, the health status widget 1204 may include a health summary 1220. In some embodiments, the health summary 1220 may provide for the display of some or all of the current health data, characteristics, conditions and/or risks for the employee. For example, as depicted, the health summary 1220 may include a listing of various health characteristics/conditions accompanied by a status of "OK" of "Alert" being indicative of the characteristic, conditions and/or risks being acceptable or needing attention, respectively. Thus, the health summary 1220 may provide a listing of current health characteristics/conditions/risks for the employee and corresponding alerts for health characteristics/conditions/risks that may require attention.

In some embodiments, the health status widget 1204 includes graphical indication of the employee's current emotion and/or facial expression. For example, the health status widget 1204 may include an emotional health avatar 1222. In some embodiments, the emotional health avatar 1222 may include a graphical depiction of the employee's current emotional state, facial expression, gestures, and/or the like. For example, in response to determining that the employee is smiling and/or happy (e.g., via the determined emotion 1036 and/or the determined facial movement 1045), the avatar 1222 may be dynamically updated (e.g., animated) to include a graphic illustration of a smile (as depicted in FIG. 12) to mimic the current emotion and/or facial expression of the employee. Thus, the emotional health avatar 1222 may reflect the employee's current emotional state, current facial expressions, gestures, and/or the like.

In some embodiments, the health status widget 1204 may provide an indication of current health conditions that justify an alert and/or may need to be addressed by the employee. For example, the health status widget 1204 may include a health alert section 1224. The health alert section 1224 may include a health status avatar 1226 that provides a graphical depiction of health alerts. Such a graphical alert may provide an easy to understand alert that directs the user's attention to the areas of concern.

The health status avatar 1226 may include a graphical depiction of the employee's current health. In some embodiments, the health status avatar 1226 includes a graphical depiction of a human body including an icon/graphic that highlights areas of the employee's body that appear to require attention. For example, in the illustrated embodiment, the health status avatar 1226 includes a heart icon/graphic displayed in response to determining that the employee has high blood pressure. In some embodiments, the graphic alert is accompanied by a corresponding textual alert message 1228. For example, in the illustrated embodiment, the health status avatar 1226 is accompanied by the textual alert message 1228 that states, "You are experiencing high blood pressure". Similar graphic alerts may be provided for other characteristics, conditions, risks and/or the like. For example, in response to a determination that the employee's eyes are fatigued, the health alert section 1224 may include an icon at the eyes of the avatar 1226 accompanied by an alert message 1228 stating, "Your eyes are fatigued".

In some embodiments, the health alert section 1224 may enable the user to access information about the health alerts. For example, upon selecting the "REVIEW ALERTS" button 1230, detailed alert information may be displayed. The detailed alert information may include details regarding the health data, characteristics, conditions and/or risk that triggered the alert (e.g., you have a blood pressure of 150/70 mmHg), suggestions for remedying the health issue (e.g., To reduce your blood pressure try to engage in at least 30 minutes of exercise each day).

In some embodiments, the interactive health dashboard may provide coaching to the user. For example, upon selecting the "COACHING/SUGGESTIONS" button 1232, a coaching avatar 1234 may be displayed to communicate suggestions and other information that may help the employee to improve their health. In some embodiments, the coaching avatar 1234 may include an animated character that talks to the employee to help communicate coaching and suggestions. For example, the coaching avatar 1234 may give the user suggestions, such as "Your blood pressure is high, try walking twenty minutes per day to reduce your blood pressure".

As a further example, the coaching avatar 1234 may give the user coaching about the suggested actions. For example, where the health plan includes performing sit-up exercises, the coaching avatar 1234 may tell the user audibly, "This is how to do a sit-up properly" followed by the avatar 1234 being animated to provide a visual demonstration of how to do a sit-up. Such coaching may help to reduce the employee's level of anxiety about engaging in the suggested activities of the health plan by providing guidance to walk the employee through the steps for meeting their health plan goals.

In some embodiments, the information provided by the health status widget 1204 may be based on the most recent health profile data for the employee. For example, where the employee undergoes a health test once per hour, the health status widget 1204 may be updated once per hour to display information corresponding to the most recent health test data 200 and health profile 1000. As a further example, where the employee undergoes continuous health testing (e.g., once per second, once per minute, etc.), the health status widget 1204 may be updated continuously (e.g., once per second, once per minute, etc.) to display information corresponding to the most recent health test. Such an embodiment may provide the employee with real-time feedback regarding their current health status/profile.

Figure 13:
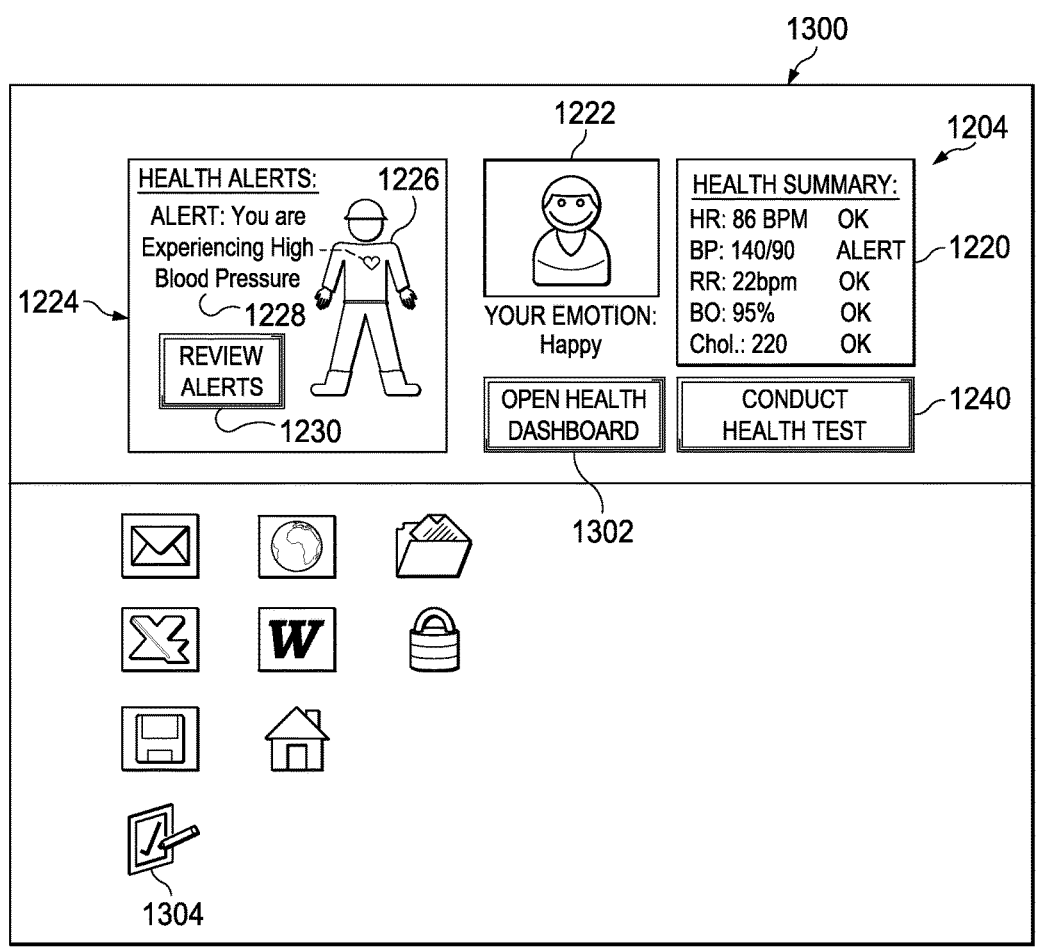
FIG. 13 is a screen-shot of an exemplary home screen including a health status widget in accordance with one or more embodiments of the present invention.

In some embodiments, the health status widget 1204 may be displayed in a home screen (e.g., desktop) of the user's device. For example, the home screen of the employee's mobile device 122 and/or the computer 130 may include the health status widget 1204. FIG. 13 is a screen-shot of an exemplary home screen 1300 including the health status widget 1204 in accordance with one or more embodiments of the present invention. In some embodiments, the health status widget 1204 displayed on the home screen 1300 includes an option to navigate to the interactive health dashboard 1012. For example, upon selecting the "Open Health Dashboard" button 1302, the interactive health dashboard 1012 may be displayed as depicted in FIG. 12. In some embodiments, the home screen 1300 includes an option to navigate to the interactive health dashboard 1012. For example, upon selecting the icon 1404, the health monitoring application may be launched, the user may login to the health monitoring application and, upon the user successfully logging in to the health monitoring application, the health status widget 1204 and/or the interactive health dashboard 1012 may be displayed as depicted in FIG. 12. The employee health status widget 1204 may be displayed on the home screen in response to the user successfully logging into the health monitoring application. The health status widget 1204 may be displayed on the user's home screen such that they can view at least some of their health information and/or corresponding health alerts while working with other applications (e.g., word processing applications, spreadsheet applications, etc.) on their mobile device 122, computer 130, workstation 103b and/or the like. In some embodiments, the interactive health report 1202 is closed and the home screen 1300, including the health status widget 1204, is displayed in response to the user selecting the "EXIT" button 1234.

In some embodiments, the health status widget 1204 may enable the user to initiate a health test of the employee. For example, upon selecting the "CONDUCT HEALTH TEST" button 1240 a health test may be conducted. Conducting a health test may include collecting current health data, processing the current health data to generate a current health profile (e.g., including health characteristics, conditions, risks and/or plans based at least in part on the updated health data), generate an updated health report based at least in part on the updated health profile, and update the display the health status widget 1204 and/or the interactive health dashboard 1012 (e.g., the interactive health report 1202 and/or the health status widget 1204) to reflect the updated health report.

Figure 14:
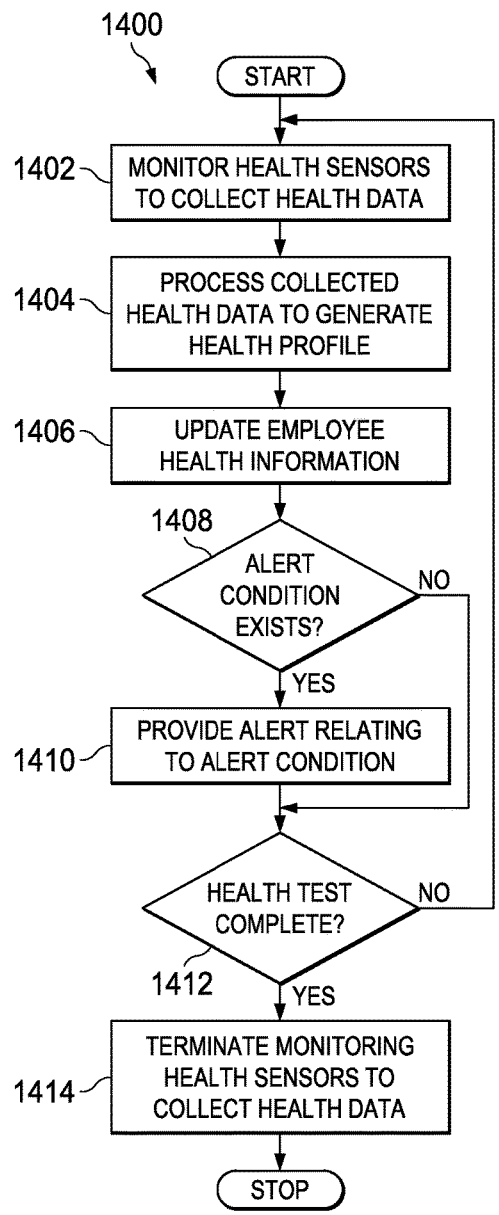
FIG. 14 is a flowchart that illustrates a method for conducting a health test in accordance with one or more embodiment of the present invention.

FIG. 14 is a flowchart that illustrates a method 1400 for conducting a health test in accordance with one or more embodiment of the present invention. Method 1400 may include monitoring health sensors to collect health data, as depicted at block 1402. In some embodiments, monitoring health sensors to collect health data includes monitoring the health sensors 120 (e.g., one or more temperature sensors 202, one or more blood condition sensors 204, one or more blood pressure sensors 206, one or more force sensors 208, one or more body fat sensors 210, one or more body position sensors 212, one or more audio sensors 214, one or more respiration sensors 216, one or more neural sensors 218, and/or one or more heart rate sensors 220) to collect corresponding health data (e.g., temperature data 200a, blood condition data 200b, blood pressure data 200c, force data 200d, body fat data 200e, body position data 200f, audio data 200g, respiration data 200h, neural data 200i and/or heart rate data 200j). In some embodiments, the health sensors 120 acquire measurement, the mobile device 122 collects health data 200 corresponding the measurements from the sensors 120, and the mobile device 122 transmits, to the server 104 via network 118, health data 200 corresponding to the collected health data 200 collected from the sensors.

In some embodiments, the method 1400 may include processing the collected health data to generate a health profile, as depicted at block 1404. For example, the collected health data 200 may be processed by the server 104 to generate a health profile 1000, including health characteristics 1002, health conditions 1004, health risks 1006, and/or health plans 1008 based at least in part on the collected health data 200.

In some embodiments, the method 1400 may include updating employee health information, as depicted at block 1406. For example, the employee's user health information 109 stored in database 108 may be updated to include the collected health data 200 and/or the health profile 1000 based at least in part on the collected health data 200.

In some embodiments, the method 1400 may include determining whether an alert condition exists, as depicted at block 1408, and, if it is determined that an alert condition does exists, providing a corresponding alert for the alert condition, as depicted at block 1410. Such a determination may be made in the course of the health test such that an immediate alert may be provided to the necessary personnel. In some embodiments, determining whether an alert condition exists includes determining whether the health data 200 and/or the heath profile 1000 is indicative of the employee incurring a health crisis (e.g., a stroke, heart attack, etc.) and, if it determined that the employee is experiencing a health crisis, generating a corresponding alert to emergency personnel and/or the employer. For example, upon detecting that the employee is currently having a heart attack, the server 104 may generate an automated the alert to the employer (e.g., via workstation 103b) and/or an automated emergency request call to the fire department, the police department, a hospital, onsite medical response personnel located at the work facility, and/or other emergency response personnel (e.g., via network server 110 and a remote workstation 112).

In some embodiments, determining whether an alert condition exists includes determining whether the health data 200 and/or the heath profile 1000 is indicative of the employee incurring a serious health risk (e.g., high potential for one of the health risk 1006 or the like), and, if it determined that the employee is experiencing a serious health risks, generating a notification to the employer and/or medical practitioners. For example, upon detecting that the employee is at risk of developing diabetes, the server 104 may generate an automated notification the employer (e.g., via workstation 103b) and/or the employee's physician (e.g., via network server 110 and a remote workstation 112).

In some embodiments, the determination of whether an employee is experiencing an alert condition is based on comparison of the health data 200 and/or the health characteristics 1002, health conditions 1004, and/or health risks 1006 to predetermined thresholds. For example, as discussed above, it may be determined that the employee is experiencing a serious medical condition where a health characteristic 1002 or condition 1004 falls outside of a predetermined normal/threshold range (e.g., exceeds a predetermined maximum and/or minimum threshold value) such as a respiration rate 1016 outside of the normal range of 12-120 breaths per minute, blood pressure 1014 outside of the normal range of 90/60-180/120, blood oxygenation level above 90%, a posture 1238 indicative of the employee being slumped over or on the floor). In some embodiments, an abnormal characteristic or condition (i.e., outside of the normal/threshold range) may be compared to other characteristics or conditions to confirm that they are, as a whole, consistent with an emergency actually occurring before proving an alert, thereby reducing the likelihood of a false alert based on an inaccurate measurement (e.g., due to a faulty sensor 120). For example, an alert may not be provided where the heart rate exceeds an upper limit but the other related characteristics and conditions (e.g., blood pressure and blood oxygenation) remain relatively unchanged (i.e., they are not abnormally elevated or low compared to a baseline). In some embodiments, the employee may be displayed an option to override the alert prior to it being sent. Such an option may enable the employee to inhibit false alerts from being transmitted.

In some embodiments, the method 1400 may include determining whether the health test is complete, as depicted at block 1412, and stopping the test routine (e.g., terminating monitoring the health sensors) where the heath test is determined to be complete, as depicted at block 1414. In some embodiments, the health test may be determined to be complete when the required health data has been collected and processed. For example, where the health test requires only a single set of measurements from sensors 120 (e.g., a single measurement from each of sensors 120), the health test may be complete after a single iteration of monitoring, processing, updating, and checking for alert conditions. As a further example, where the health test requires a set of measurements from sensors 120 be collected over a given period of time (e.g., one minute, five minutes, one hour, eight hours), the health test may not be complete until the expiration of the given period of time. Thus, for example, iterations of health testing may continue for one minute, five minutes, one hour, eight hours, or the like.

Although some embodiments refer to the method 1400 for conducting a health test being executed in response to a user request via selection of the "CONDUCT HEALTH TEST" button 1240, it will be appreciated that such a test routine may be executed in response to any variety of requests. In some embodiments, the method 1400 may be executed automatically in accordance with a corresponding test schedule as discussed above. For example, where a health test schedule requires collection of health data 200 at 12:00 pm), the method 1400 may be automatically executed at 12:00 pm. As another example, where a health test schedule requires the continuous collection of a batch of health data 200 from 8:00 am-6:00 pm, the method 1400 may be automatically executed at 8:00 am, and may not be completed until 6:00 pm. As yet another example, where a health test schedule requires the repeated collection of health data 200 at an hourly interval from 8:00 am-6:00 pm, the method 1400 may be automatically executed at 8:00 am, 9:00 am, and so forth.

In some embodiments, an interactive health dashboard provides a user the opportunity to select to review health information for a particular employee and/or health information for a plurality of employees. For example, an employer may be provided with an interactive health dashboard that enables them to review health information for a particular employee, initiate health tests, and/or review health information for groups of employees (e.g., employees working at a particular worksite, facility, region, division, team, or the like). In some embodiments, access to such an interactive health dashboard that enables review of health information for persons other than the current user is controlled by the user's account permissions. For example, upon an employer logging in to the health monitoring application using their credentials, the server 104 may recognize the user as the employer based on the login credentials, and serve, to the employer's workstation 103*b* for display, an interactive health dashboard (e.g., a reviewer interactive health dashboard) that enables selection of various employees and/or groups of employees to review.

Figure 15:
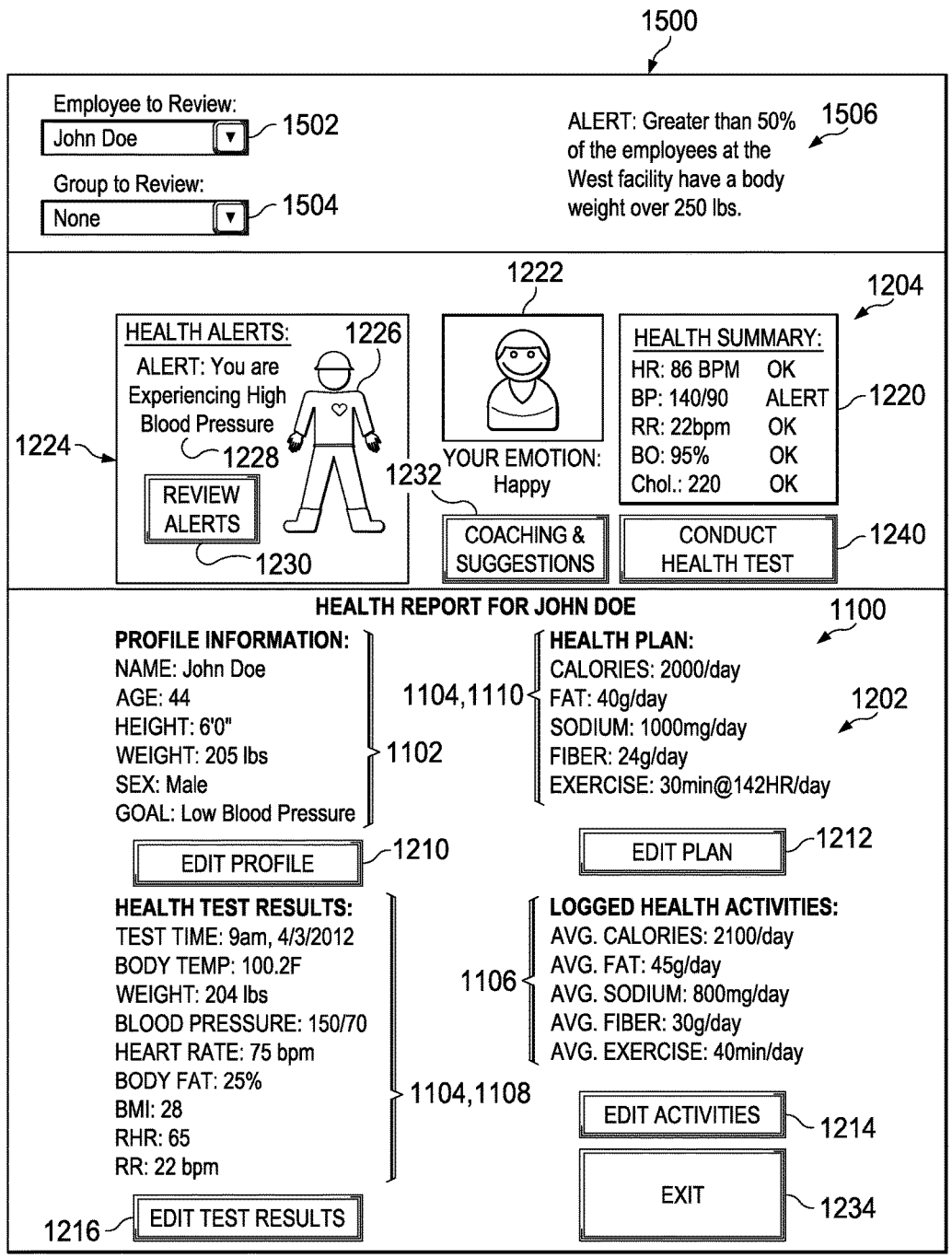
FIG. 15 illustrates an exemplary reviewer interactive health dashboard in accordance with one or more embodiments of the present invention.

FIG. 15 depicts an exemplary reviewer interactive health dashboard ("reviewer dashboard") 1500 in accordance with one or more embodiments of the present invention. In some embodiments, the user has the ability to select one or more employees for which they would like to review health information. For example, where the user is an employer having permission to review a set of employee's health information, a drop-down selection box 1502 is populated with the names of the individual employees of the set of the employees. Upon selection of an individual employee (e.g., John Doe), the reviewer dashboard 1500 may display an interactive health report and/or a health status widget that is the same or similar to the interactive health dashboard that would be displayed to the employee (i.e., the same or similar to the interactive health report 1202 and/or health status widget 1204 for the selected employee described above). Thus, for example, the reviewer may review and/or edit the selected employee's health profile, health report, and even initiate a health test for the employee. Such review may enable the employer to review their employee's health information to identify health conditions that may need to be addressed, to track employees' progress with regard to health plans, to ensure employees are engaging with the health monitoring system/application, and/or the like.

In some embodiments, a reviewer interface enables a reviewer to select a plurality of employee's (e.g., a group of employees) to review. For example, a group drop-down box 1504 may enable a reviewer to select a particular worksite, facility, region, division, team, or the like. Upon selection of a group (e.g., a particular worksite, facility, region, division, team, or the like) the reviewer dashboard may display health data/reports corresponding the selected group of employees. For example, where the user selects a particular facility, the reviewer may be presented with a report similar to that of report 1310 of FIG. 13B, for the group of employees working at the selected facility. Such a group report may include the average values of the health characteristics, conditions, risk, plans and/or the like for the group, and/or corresponding statistics that can be used to assess the health of the group (e.g., standard deviations, etc.). Such an embodiment may enable the employer to determine whether or not a particular group of employees is experiencing normal or abnormal health conditions. For example, where a report for a worksite indicates that an abnormally high percentage of the employees at the facility have symptoms of allergies, the reviewer may determine that steps need to be taken at the worksite to reduce airborne contaminants that may be causing the allergy symptoms. As a further example, where a report for a team indicates that an abnormally high percentage of the employee team members have symptoms of high stress or depression, the reviewer may determine that steps need to be taken to reduce the stress level and/or depression for the team. Thus, the review of employee health may enable the employer to take steps to improve employee health, which may, in turn, increase the employee's productivity.

In some embodiments, the system 100 may identify whether or not a group of employees appears to be experiencing similar conditions, characteristics, risks or the like, and may provide a corresponding alert to the employer. For example, where a report for a worksite indicates that an abnormally high percentage of the employees at the facility have symptoms of allergies, the system 100 may generate an alert to the employer regarding the condition.

Figure 16:
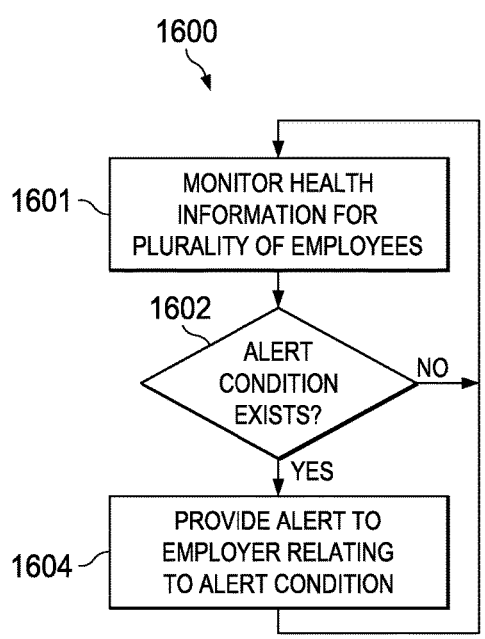
FIG. 16 is a flowchart that illustrates a method of assessing health information for a plurality of employees in accordance with one or more embodiments of the present invention.

FIG. 16 is a flowchart that illustrates a method 1600 of assessing health information for a plurality of employees to determine whether an alert condition exists in accordance with one or more embodiments of the present invention. Method 1600 may include monitoring health information for a plurality of employees, as depicted at block 1601. In some embodiments, monitoring health information for a plurality of employees (e.g., a group of employees) includes reviewing the health profile data for a discrete group of employees. For example, monitoring health information for a plurality of employees may include reviewing health profile data for all of the employees that work in a particular worksite, facility, region, division, team, or the like. In some embodiments, monitoring health information for a plurality of employees includes determining the number/percentage of the plurality of employees that are experiencing a given characteristic, condition or risk. For example, monitoring health information for a plurality of employees may include determining a percentage of the employee's that have a body weight above 113 kg (250 lbs.). In some embodiments, monitoring health information for a plurality of employees includes determining a single value for a given characteristic, condition or risk. For example, monitoring health information for a plurality of employees may include determining an average body weight for the plurality of employees. Other embodiments may include similar determinations for various other characteristics 1002, conditions 1004 and/or risks 1006.

Method 1600 may include determining whether an alert condition exists (e.g., based on the review of the health profile data for the plurality of employees), as depicted at block 1602. In some embodiments, it may be determined that an alert condition exists based on comparison of results of the monitoring to predetermined threshold values. For example, where a threshold percentage for a group of employees over 113 kg (250 lbs.) is 50%, it may be determined that an alert condition exists if greater than 50% of the group of employees has a body weight above 113 kg (250 lbs.). As a further example, where a threshold average body weight for a group of employees is 113 kg (250 lbs.), it may be determined that an alert condition exists if the average body weight for the group of employees is above 113 kg (250 lbs.). Other embodiments may include similar determinations for various other characteristics 1302, conditions 1304 and risks 1306. Alerting the employer to predicted health issues and/or associated health risks may enable the employer to proactively respond to predicted health issues and/or associated health risks before they escalate into actual health issues. For example, where an alert indicates that a high percentage of employees at a facility are at risk for becoming obese, the employer may be able to implement a dietary program and/or an exercise program for the employees at the facility to help prevent the employees from becoming obese.

In response to determining that an alert condition exists, method 1600 may proceed to providing an alert to the employer relating to the alert condition, as depicted at block 1604. In some embodiments, providing an alert to the employer relating to the alert condition may include providing the employer with an alert indicating that a plurality of the employees each have health profiles that are of concern. For example, upon logging into the health monitoring application, the employer may be provided with a homepage screen that includes an alert relating to the alert condition.

FIG. 15 illustrates the reviewer dashboard 1500 including an alert 1506 in accordance with one or more embodiments of the present technique. An alert may include an icon, text, or other information that is indicative of a plurality of employees experiencing health characteristics, conditions, or risk that may be of concern. For example, in the illustrated embodiment, the alert 1506 is provided in a widget of the reviewer dashboard 1500 and states, "Greater than 50% of the employees at the West facility have a body weight over 250 lbs." Such embodiments may provide employers with the ability to identify and remedy health issues that may be affecting a group of employees.

It will be appreciated that methods 900, 1400 and 1600 are exemplary embodiments of methods that may be employed in accordance with techniques described herein. The methods 900, 1400 and 1600 may be may be modified to facilitate variations of its implementations and uses. The methods 900, 1400 and 1600 may be implemented in software, hardware, or a combination thereof. Some or all of the methods 900, 1400 and 1600 may be implemented by one or more of the modules/applications described herein, such as server module 810. The order of the methods 900, 1400 and 1600 may be changed, and various elements may be added, reordered, combined, omitted, modified, etc.

In some embodiments, some or all of methods 900, 1400 and/or 1600 may be executed by the mobile device module 308. For example, the mobile device 122 may collect the personal profile from the employee, collect the health data 200, process the health data to generate the health profile 1000 (e.g., the health characteristics 1002, conditions 104, risks 106 and/or plans 108), generate the health report 1010, generate the interactive health dashboard 1012, and/or display the health report 1010 and/or the interactive health dashboard 1012 for display to the employee. As will be understood by those skilled in the art, such an embodiment, including local execution of some or all of the methods by the mobile device 122, may help to reduce and/or eliminate the processing load on the server 104.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

As used throughout this application, the word "may" is used in a permissive sense (i.e., meaning having the potential to), rather than the mandatory sense (i.e., meaning must). The words "include", "including", and "includes" mean including, but not limited to. As used throughout this application, the singular forms "a", "an" and "the" include plural referents unless the content clearly indicates otherwise. Thus, for example, reference to "an element" may include a combination of two or more elements. Unless specifically stated otherwise, as apparent from the discussion, it is appreciated that throughout this specification discussions utilizing terms such as "processing", "computing", "calculating", "determining" or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical electronic or magnetic quantities within memories, registers, or other information storage devices, transmission devices, or display devices of the special purpose computer or similar special purpose electronic processing/computing device.

The techniques described herein may include or otherwise be used in conjunction with techniques described in U.S. Provisional Patent Application No. 61/664,387 filed on Jun. 26, 2012 and titled "SYSTEMS, COMPUTER MEDIUM AND COMPUTER-IMPLEMENTED METHODS FOR MONITORING HEALTH OF EMPLOYEES USING MOBILE DEVICES", U.S. Provisional Patent Application No. 61/504,638 filed on Jul. 5, 2011 and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831 filed on Jun. 14, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790 filed on Jun. 14, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796 filed on Jun. 14, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800 filed on Jun. 14, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807 filed on Jun. 14, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810 filed on Jun. 14, 2012 and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818 filed on Jun. 14, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. Provisional Patent Application No. 61/659,824 filed on Jun. 14, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. Provisional Patent Application No. 61/664,399 filed on Jun. 26, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", and U.S. Provisional Patent Application No. 61/664,414 filed on Jun. 26, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES", the disclosures of which are each hereby incorporated by reference in their entireties.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

What is claimed is:

1. A system to monitor health of an employee in a work environment, the system comprising:
   a communications network;
   a health database connected to the communications network, the database storing health information for one or more employees;
   a set of one or more health sensors configured to sense health characteristics of the employee, and to output health sensor data corresponding to the health characteristics sensed by the set of one or more health sensors, the set of one or more health sensors comprising
   a pair of work gloves comprising:
      hand force sensors comprising a right hand force sensor located in a right work glove of the pair of work gloves to be worn on a right hand of the employee and a left hand force sensor located in a left work glove of the pair of work gloves to be worn on a left hand of the employee, the right hand force sensor configured to sense a force at the right hand of the employee, the left hand force sensor configured to sense a force at the left hand of the employee, and the hand force sensors configured to output hand force data indicative of the force at the right hand of the employee sensed and the force at the left hand of the employee sensed; and
      hand position sensors comprising a right hand position sensor located in the right work glove and a left hand position sensor located in the left work glove of the pair of work gloves, the right hand position sensor configured to sense a position of the right hand of the employee, the left hand position sensor configured to sense a position of the left hand of the employee, and the hand position sensors configured to output hand position data indicative of the position of the right hand of the employee sensed and the position of the left hand of the employee sensed; and
   a pair of work footwear comprising:
      foot force sensors comprising a right foot force sensor located in a right work footwear of the pair of work footwear to be worn on a right foot of the employee and a left foot force sensor located in a left footwear of the pair of work footwear to be worn on a left foot of the employee, the right foot force sensor configured to sense a force at the right foot of the employee, the left foot force sensor configured to sense a force at the left foot of the employee, and the foot force sensors configured to output foot force data indicative of the force at the right foot of the employee sensed and the force at the left foot of the employee sensed; and foot position sensors comprising a right foot position sensor located in the right work footwear and a left foot position sensor located in the left work footwear of the pair of work footwear, the right foot position sensor configured to sense a position of the right foot of the employee, the left foot position sensor configured to sense a position of the left foot of the employee, and the foot position sensors configured to output foot position data indicative of the position of the right foot of the employee sensed and the position of the left foot of the employee sensed, the health sensor data comprising:

force data indicating a force exerted by the employee, the force data comprising the hand force data and the foot force data; and position data indicating a body position of the employee, the position data comprising the hand position data and the foot position data;

a mobile communications device connected to the communications network, the mobile communications device configured to collect the health sensor data from the set of one or more health sensors and to output health data corresponding to the health sensor data collected from the set of one or more health sensors, the mobile communications device comprising at least one of the one or more health sensors integrated therein to sense at least one biometric or biomechanic characteristic for the employee; and a health server connected to the communications network, the health server configured to:

receive, from the mobile communications device via the communications network, the health data output by the mobile communications device;

determine, based on the health data received, that the employee engaged in a physical exertion defined by the force exerted by the employee and the body position of the employee;

compare the force exerted by the employee to a predefined threshold force to determine that the force exerted by the employee is above the predefined threshold force;

compare the body position of the employee to a predefined body position to determine that the body position of the employee deviates from the predefined body position;

determine a predicted physical injury based on the determination that the force exerted by the employee is above the predefined threshold force and the body position of the employee deviates from the predefined body position;

determine, based on the health data received, a health profile for the employee, the health profile comprising one or more predicted health issues and at least one of health characteristics, health conditions, health risks and health plans for the employee determined based on the health data received, wherein each of the one or more predicted health issues comprises a health issue that is determined, based on the health data, to be a potential health issue which is not being experienced by the employee at a current time, but is predicted, based on the health data, to escalate into an actual health issue which will be experienced by the employee at a future time, and wherein the one more predicted health issues comprise the predicted physical injury;

update the health information stored in the health database to reflect the health profile for the employee; and serve, to the mobile communications device for display to the employee via a graphical display of the mobile communications device, health report content comprising at least one of the health characteristics, the health conditions, the health risks and the health plans of the health profile for the employee, and content indicative of the one or more predicted health issues;

the mobile communications device being further configured to display the health report content, including the content indicative of the one or more predicted health issues, such that the employee is alerted to the one or more predicted health issues via the graphical employee interface of the mobile communications device used to collect the health sensor data and is afforded an opportunity to address the one or more predicted health issues prior to the one or more predicted health issues escalating into an actual health issue.

2. A system according to claim 1, wherein the at least one of the set of one or more health sensors integrated within the mobile communication device comprises a sensor pad comprising one or more conductive contacts configured to sense at least one biometric or biomechanic characteristic of the employee via physical contact between skin of the employee and the one or more conductive contacts.

3. A system according to claim 1, wherein the mobile communication device comprises a handheld mobile communications device, wherein the at least one of the set of one or more health sensors integrated within the mobile communication device comprises a body fat sensor comprising a sensor pad, wherein the sensor pad comprises two conductive contacts physically integrated within a body of the mobile communication device and configured to be grasped by the employee's right and left hands during use, wherein the mobile communications device is configured to take a resistance measurement across the two conductive contacts while the two conductive contacts are grasped by the employee's right and left hands such that the resistance measurement is indicative of a body fat of the employee across the employee's right and left hands, and wherein the health sensor data collected by the mobile communications device comprises body fat data indicative of the resistance measurement.

4. A system according to claim 1, wherein the at least one of the set of one or more health sensors integrated within the mobile communication device comprises a body temperature sensor comprising a sensor pad, wherein the sensor pad comprises a conductive contact configured to contact the employee's hand during use, wherein the mobile communications device is configured to take a temperature measurement from the conductive contact while the conductive contact is grasped by the employee's hand such that the temperature measurement is indicative of a body temperature of the employee, and wherein the health sensor data collected by the mobile communications device comprises temperature data indicative of the temperature measurement.

5. A system according to claim 1, wherein the at least one of the set of one or more health sensors integrated within the mobile communication device comprises a sensor screen configured to sense at least one biometric or biomechanic characteristic of the employee via physical contact between skin of the employee and the sensor screen.

6. A system according to claim 5, wherein the sever is configured to verify the employee's identity, wherein the sensor screen comprises a touch screen configured collect at least one of a finger print and a hand print of the employee by way of contact of the employee's finger or hand with the screen, and wherein the employee's identify is verified based on the at least one of a finger print and hand print collected via the touch screen of the mobile communication device.

7. A system according to claim 1, wherein the at least one of the set of one or more health sensors integrated within the mobile communication device comprises a temperature sensor comprising a thermal imaging camera configured to acquire thermal image data indicative of the body temperature of the employee, and wherein the health sensor data collected by the mobile communications device comprises temperature data corresponding to the thermal image data indicative of the body temperature of the employee.

8. A system according to claim 1, wherein the at least one of the set of one or more health sensors integrated within the mobile communication device comprises a temperature sensor comprising an infrared (IR) sensor configured to acquire IR data indicative of the body temperature of the employee, and wherein the health sensor data collected by the mobile communications device comprises temperature data corresponding to the IR data indicative of the body temperature of the employee.

9. A system according to claim 1, wherein the at least one of the set of one or more health sensors integrated within the mobile communication device comprises a position sensor comprising a camera configured to acquire image data indicative of the body position of the employee, and wherein the health sensor data collected by the mobile communications device comprises position data corresponding to the image data indicative of the body position of the employee.

10. A system according to claim 1, wherein the one or more health sensors comprises remote sensors in communication with the mobile communication device,
and configured to transmit, to the mobile communications device, the health sensor data.

11. A system according to claim 10, wherein the remote sensors are configured to transmit, to the mobile communications device, the health sensor data via a wireless connection between the at least one or more remote sensors and the mobile communications device.

12. A system according to claim 1, wherein the health profile comprises at least one of a body temperature, a body weight, a body fat, a heart rate, a blood pressure, a blood oxygenation level, a respiration rate, brain activity,the body position, eye movement, and the physical exertion for the employee determined based on the health data received.

13. A system according to claim 1, wherein the health profile comprises at least one of a risk of obesity, a risk of injury, a risk of diabetes, a risk of infection, a risk of inflammation, a risk of circulation problems, a risk of cardio vascular disease, a risk of cardio vascular accidents, a risk of illness, a risk of asthma, a risk of allergies, a risk of bronchitis, a risk of musculoskeletal syndrome, a risk of carpal tunnel syndrome, a risk of epicondylitis, a risk of rotator cuff injury, a risk of eye disease, and a risk of physical fatigue determined based on the health data received.

14. A system according to claim 1, wherein the mobile communications device comprises at least one of a cellular phone, a personal digital assistant (PDA), and tablet computer.

15. A system according to claim 1, wherein the mobile communication device comprises a handheld mobile phone device or handheld tablet computer device comprising at least two conductive contacts physically integrated within a body of the device, and configured to be grasped by the employee's right and left hands during use to sense at least one biometric or biomechanic characteristic of the employee via physical contact between skin of the employee and the one or more conductive contacts.

16. The system of claim 1, wherein the right hand force sensor is located in a palm of the right work glove of the pair of work gloves, the left hand force sensor is located in a palm of the left work glove of the pair of work gloves, the right foot force sensor is located in a sole of the right work footwear of the pair of work footwear, and the left foot force sensor is located in a sole of the left work footwear of the pair of work footwear.

17. A system for monitoring health of an employee, the system comprising:
a pair of work gloves comprising:
hand force sensors comprising a right hand force sensor located in a right work glove of the pair of work gloves to be worn on a right hand of the employee and a left hand force sensor located in a left work glove of the pair of work gloves to be worn on a left hand of the employee, the right hand force sensor configured to sense a force at the right hand of the employee, the left hand force sensor configured to sense a force at the left hand of the employee, and the hand force sensors configured to output hand force data indicative of the force at the right hand of the employee sensed and the force at the left hand of the employee sensed;
hand position sensors comprising a right hand position sensor located in the right work glove and a left hand position sensor located in the left work glove of the pair of work gloves, the right hand position sensor configured to sense a position of the right hand of the employee, the left hand position sensor configured to sense a position of the left hand of the employee, and the hand position sensors configured to output hand position data indicative of the position of the right hand of the employee sensed and the position of the left hand of the employee sensed;
a pair of work footwear comprising:
foot force sensors comprising a right foot force sensor located in a right work footwear of the pair of work footwear to be worn on a right foot of the employee and a left foot force sensor located in a left footwear of the pair of work footwear to be worn on a left foot of the employee, the right foot force sensor configured to sense a force at the right foot of the employee, the left foot force sensor configured to sense a force at the left foot of the employee, and the foot force sensors configured to output foot force data indicative of the force at the right foot of the employee sensed and the force at the left foot of the employee sensed;
foot position sensors comprising a right foot position sensor located in the right work footwear and a left foot position sensor located in the left work footwear of the pair of work footwear, the right foot position sensor configured to sense a position of the right foot of the employee, the left foot position sensor configured to sense a position of the left foot of the employee, and the foot position sensors configured to output foot position data indicative of the position of the right foot of the employee sensed and the position of the left foot of the employee sensed;

a set of one or more health sensors configured to be provided on or near the employee while the employee is engaged in their work duties, the set of one or more health sensors configured to sense health characteristics of the employee and to output health sensor data corresponding to the health characteristics sensed by the set of one or more health sensors, the set of one or more health sensors comprising the hand force sensors, the hand position sensors, the foot force sensors, and the foot position sensors, and the health sensor data comprising:

force data indicating a force exerted by the employee, the force data comprising the hand force data and the foot force data; and position data indicating a body position of the employee, the position data comprising the hand position data and the foot position data; and a mobile communications device comprising at least one of the one or more health sensors integrated therein to sense at least one biometric or biomechanic characteristic for the employee, the mobile communications device being configured to:

collect the health sensor data from the set of one or more health sensors, wherein the health sensor data collected is used to determine a predicted physical injury based on a determination that the force exerted by the employee is above a predefined threshold force and the body position of the employee deviates from a predefined body position, and determine a health profile for the employee, the health profile comprising one or more predicted health issues and at least one of health characteristics, health conditions, health risks and health plans for the employee determined based on the health sensor data collected, wherein each of the one or more predicted health issues comprises a health issue that is determined, based on the health sensor data collected, to be a potential health issue which is not being experienced by the employee at a current time, but is predicted, based on the health sensor data collected, to escalate into an actual health issue which will be experienced by the employee at a future time, wherein the one more predicted health issues comprise the predicted physical injury; and display, via a graphical user interface of the mobile communications device, a health report comprising at least one of the health characteristics, the health conditions, the health risks and the health plans of the health profile for the employee determined based on the health sensor data collected, the displayed health report comprising content indicative of the one or more predicted health issues such that the employee is alerted to the one or more predicted health issues via the graphical user interface of the mobile communications device used to collect the health sensor data and is afforded an opportunity to address the one or more predicted health issues prior to the one or more predicted health issues escalating into an actual health issue.

18. A system according to claim 17, wherein one or more of the set of one or more health sensors is located in at least one of a safety helmet, or work clothing configured to be worn by the employee while the employee is engaged in their work duties.

19. A system according to claim 17, wherein the one or more health sensors comprises remote sensors in communication with the mobile communication device, and configured to transmit, to the mobile communications device, the health data.

20. A system according to claim 19, wherein the one or more health sensors comprises at least one neural sensor located in a safety helmet configured to be worn by the employee while the employee is engaged in their work duties.

21. A system according to claim 17, wherein the mobile communication device comprises a handheld mobile communications device, wherein the at least one of the one or more health sensors integrated with the mobile communications device comprises at least one of a sensor pad, a sensor screen, a thermal camera and an infrared (IR) sensor.

22. A non-transitory computer readable storage medium comprising program instructions for monitoring health of an employee in a work environment, the computer program instructions being executable by a computer processor to cause the steps of:

receiving, via a communications network, health data output by a mobile communications device, the mobile communications device connected to the communications network, the mobile communications device configured to collect, from a set of one or more health sensors configured to sense health characteristics of the employee and to output health sensor data corresponding to the health characteristics sensed by the set of one or more health sensors, the health sensor data, the mobile communications device configured to output health data corresponding to the health sensor data collected from the set of one or more health sensors, the mobile communications device comprising at least one of the one or more health sensors integrated therein to sense at least one biometric or biomechanic characteristic for the employee, and the set of one or more health sensors comprising:

a pair of work gloves comprising:

hand force sensors comprising a right hand force sensor located in a right work glove of the pair of work gloves worn on a right hand of the employee and a left hand force sensor located in a left work glove of the pair of work gloves worn on a left hand of the employee, the right hand force sensor configured to sense a force at the right hand of the employee, the left hand force sensor configured to sense a force at the left hand of the employee, and the hand force sensors configured to output hand force data indicative of the force at the right hand of the employee sensed and the force at the left hand of the employee sensed; and hand position sensors comprising a right hand position sensor located in the right work glove and a left hand position sensor located in the left work glove of the pair of work gloves, the right hand position sensor configured to sense a position of the right hand of the employee, the left hand position sensor configured to sense a position of the left hand of the employee, and the hand position sensors configured to output hand position data indicative of the position of the right hand of the employee sensed and the position of the left hand of the employee sensed; and a pair of work footwear comprising:
foot force sensors comprising a right foot force sensor located in a right work footwear of the pair of work footwear worn on a right foot of the employee and a left foot force sensor located in a left footwear of the pair of work footwear worn on a left foot of the employee, the right foot force sensor configured to sense a force at the right foot of the employee, the left foot force sensor configured to sense a force at the left foot of the employee, and the foot force sensors configured to output foot force data indicative of the force at the right foot of the employee sensed and the force at the left foot of the employee sensed; and
foot position sensors comprising a right foot position sensor located in the right work footwear and a left foot position sensor located in the left work footwear of the pair of work footwear, the right foot position sensor configured to sense a position of the right foot of the employee, the left foot position sensor configured to sense a position of the left foot of the employee, and the foot position sensors configured to output foot position data indicative of the position of the right foot of the employee sensed and the position of the left foot of the employee sensed,
the health sensor data comprising:
force data indicating a force exerted by the employee, the force data comprising the hand force data and the foot force data; and
position data indicating a body position of the employee, the position data comprising the hand position data and the foot position data;
determining, based on the health data received, that the employee engaged in a physical exertion defined by the force exerted by the employee and the body position of the employee;
comparing the force exerted by the employee to a predefined threshold force to determine that the force exerted by the employee is above the predefined threshold force;
comparing the body position of the employee to a predefined body position to determine that the body position of the employee deviates from the predefined body position;
determining a predicted physical injury based on the determination that the force exerted by the employee is above the predefined threshold force and the body position of the employee deviates from the predefined body position;
determining, based on the received health data, a health profile for the employee, the health profile comprising one or more predicted health issues and at least one of health characteristics, health conditions, health risks and health plans for the employee determined based on the received health data, wherein each of the one or more predicted health issues comprises a health issue that is determined, based on the health data, to be a potential health issue which is not being experienced by the employee at a current time, but is predicted, based on the health data, to escalate into an actual health issue which will be experienced by the employee at a future time, and wherein the one more predicted health issues comprise the predicted physical injury;
updating health information stored in a health database to reflect the health profile for the employee; and serving, to the mobile communications device for display to the employee via a graphical display of the mobile communications device, health report content comprising at least one of the health characteristics, the health conditions, the health risks and the health plans of the health profile for the employee, and content indicative of the one or more predicted health issues such that the employee is alerted to the one or more predicted health issues via the graphical user interface of the mobile communications device used to collect the health sensor data and is afforded an opportunity to address the one or more predicted health issues prior to the one or more predicted health issues escalating into an actual health issue.

23. A method for monitoring health of an employee, the method comprising:
providing, on or near the employee while the employee is engaged in their work duties, a set of one or more health sensors configured to sense health characteristics of the employee, and to output health sensor data corresponding to the health characteristics sensed by the set of one or more health sensors, at least one of the one or more health sensors integrated within a mobile communications device, the set of one or more health sensors comprising:
a pair of work gloves comprising:
hand force sensors comprising a right hand force sensor located in a right work glove of the pair of work gloves worn on a right hand of the employee and a left hand force sensor located in a left work glove of the pair of work gloves worn on a left hand of the employee, the right hand force sensor configured to sense a force at the right hand of the employee, the left hand force sensor configured to sense a force at the left hand of the employee, and the hand force sensors configured to output hand force data indicative of the force at the right hand of the employee sensed and the force at the left hand of the employee sensed; and
hand position sensors comprising a right hand position sensor located in the right work glove and a left hand position sensor located in the left work glove of the pair of work gloves, the right hand position sensor configured to sense a position of the right hand of the employee, the left hand position sensor configured to sense a position of the left hand of the employee, and the hand position sensors configured to output hand position data indicative of the position of the right hand of the employee sensed and the position of the left hand of the employee sensed; and
a pair of work footwear comprising:
foot force sensors comprising a right foot force sensor located in a right work footwear of the pair of work footwear worn on a right foot of the employee and a left foot force sensor located in a left footwear of the pair of work footwear worn on a left foot of the employee, the right foot force sensor configured to sense a force at the right foot of the employee, the left foot force sensor configured to sense a force at the left foot of the employee, and the foot force sensors configured to output foot force data indicative of the force at the right foot of the employee sensed and the force at the left foot of the employee sensed; and
foot position sensors comprising a right foot position sensor located in the right work footwear and a left foot position sensor located in the left work footwear of the pair of work footwear, the right foot position sensor configured to sense a position of the right foot of the employee, the left foot position sensor configured to sense a position of the left foot of the employee, and the foot position sensors configured to output foot position data indicative of the position of the right foot of the employee sensed and the position of the left foot of the employee sensed, the health sensor data comprising:
force data indicating a force exerted by the employee, the force data comprising the hand force data and the foot force data; and
position data indicating a body position of the employee, the position data comprising the hand position data and the foot position data collecting, by the mobile communications device, the health sensor data from a set of one or more health sensors provided;

determining, based on the health sensor data collected by the mobile communications device, a health profile for the employee, the health profile comprising one or more predicted health issues and at least one of health characteristics, health conditions, health risks and health plans for the employee determined based on the health data collected, wherein each of the one or more predicted health issues comprises a health issue that is determined, based on the health data, to be a potential health issue which is not being experienced by the employee at a current time, but is predicted, based on the health data, to escalate into an actual health issue which will be experienced by the employee at a future time;

determining, based on the health sensor data collected by the mobile communications device, that the employee engaged in a physical exertion defined by the force exerted by the employee and the body position of the employee;

comparing the force exerted by the employee to a predefined threshold force to determine that the force exerted by the employee is above the predefined threshold force;

comparing the body position of the employee to a predefined body position to determine that the body position of the employee deviates from the predefined body position;

determining a predicted physical injury based on the determination that the force exerted by the employee is above the predefined threshold force and the body position of the employee deviates from the predefined body position, wherein the one more predicted health issues comprise the predicted physical injury; and displaying, via a graphical user interface of the mobile communications device, a health report comprising at least one of the health characteristics, the health conditions, the health risks and the health plans of the health profile for the employee determined based on the health sensor data collected, and content indicative of the one or more predicted health issues such that the employee is alerted to the one or more predicted health issues via the graphical user interface of the mobile communications device used to collect the health sensor data and is afforded an opportunity to address the one or more predicted health issues prior to the one or more predicted health issues escalating into an actual health issue, wherein the one more predicted health issues comprise the predicted physical injury.

24. A method for monitoring health of an employee, the method comprising:

collecting, by a mobile communication device, health data from a set of one or more health sensors provided on or near the employee while the employee is engaged in their work duties, at least one of the one or more health sensors integrated within a mobile communications device, the one or more health sensors configured to output health sensor data corresponding to characteristics sensed by the health sensors, the one or more health sensors comprising at least one or more biometric sensors configured to sense biometric characteristics of the employee and biomechanic sensors configured to sense biomechanic characteristics of the employee, the set of one or more health sensors comprising:

a pair of work gloves comprising:
hand force sensors comprising a right hand force sensor located in a right work glove of the pair of work gloves worn on a right hand of the employee and a left hand force sensor located in a left work glove of the pair of work gloves worn on a left hand of the employee, the right hand force sensor configured to sense a force at the right hand of the employee, the left hand force sensor configured to sense a force at the left hand of the employee, and the hand force sensors configured to output hand force data indicative of the force at the right hand of the employee sensed and the force at the left hand of the employee sensed; and
hand position sensors comprising a right hand position sensor located in the right work glove and a left hand position sensor located in the left work glove of the pair of work gloves, the right hand position sensor configured to sense a position of the right hand of the employee, the left hand position sensor configured to sense a position of the left hand of the employee, and the hand position sensors configured to output hand position data indicative of the position of the right hand of the employee sensed and the position of the left hand of the employee sensed; and a pair of work footwear comprising:
foot force sensors comprising a right foot force sensor located in a right work footwear of the pair of work footwear worn on a right foot of the employee and a left foot force sensor located in a left footwear of the pair of work footwear worn on a left foot of the employee, the right foot force sensor configured to sense a force at the right foot of the employee, the left foot force sensor configured to sense a force at the left foot of the employee, and the foot force sensors configured to output foot force data indicative of the force at the right foot of the employee sensed and the force at the left foot of the employee sensed; and
foot position sensors comprising a right foot position sensor located in the right work footwear and a left foot position sensor located in the left work footwear of the pair of work footwear, the right foot position sensor configured to sense a position of the right foot of the employee, the left foot position sensor configured to sense a position of the left foot of the employee, and the foot position sensors configured to output foot position data indicative of the position of the right foot of the employee sensed and the position of the left foot of the employee sensed, the health sensor data comprising:
  force data indicating a force exerted by the employee, the force data comprising the hand force data and the foot force data; and
  position data indicating a body position of the employee, the position data comprising the hand position data and the foot position data;

determining, based on the health sensor data collected by the mobile communication device, that the employee engaged in a physical exertion defined by the force exerted by the employee and the body position of the employee;

compare the force exerted by the employee to a predefined threshold force to determine that the force exerted by the employee is above the predefined threshold force;

compare the body position of the employee to a predefined body position to determine that the body position of the employee deviates from the predefined body position;

determine a predicted physical injury based on the determination that the force exerted by the employee is above the predefined threshold force and the body position of the employee deviates from the predefined body position;

determining a health profile for the employee using the health data collected, the health profile comprising one or more predicted health issues and at least one of health characteristics, health conditions, health risks and health plans for the employee determined based on the health data collected, wherein each of the one or more predicted health issues comprises a health issue that is determined, based on the health data, to be a potential health issue which is not being experienced by the employee at a current time, but is predicted, based on the health data, to escalate into an actual health issue which will be experienced by the employee at a future time, and wherein the one more predicted health issues comprise the predicted physical injury; and providing for display via a graphical user interface of the mobile communications device, a health report comprising at least one of the health characteristics, the health conditions, the health risks and the health plans of the health profile for the employee determined based on the health data collected, and content indicative of the one or more predicted health issues such that the employee is alerted to the one or more predicted health issues via the graphical user interface of the mobile communications device used to collect the health sensor data and is afforded an opportunity to address the one or more predicted health issues prior to the one or more predicted health issues escalating into an actual health issue.

\* \* \* \* \*